US011014125B2

United States Patent
Aase et al.

(10) Patent No.: US 11,014,125 B2
(45) Date of Patent: May 25, 2021

(54) HAND REMOVABLE, CLIP ON WAX GUARDS

(71) Applicant: Eargo, Inc., San Jose, CA (US)

(72) Inventors: Jonathan Sarjeant Aase, Sunnyvale, CA (US); Michael Barrett, Campbell, CA (US); Daniel Z. Shen, Palo Alto, CA (US)

(73) Assignee: Eargo, Inc., San Jose, CA (US)

( * ) Notice: Subject to any disclaimer, the term of this patent is extended or adjusted under 35 U.S.C. 154(b) by 53 days.

(21) Appl. No.: 16/153,303

(22) Filed: Oct. 5, 2018

(65) Prior Publication Data

US 2019/0110928 A1 Apr. 18, 2019

Related U.S. Application Data

(60) Provisional application No. 62/573,254, filed on Oct. 17, 2017, provisional application No. 62/621,422, (Continued)

(51) Int. Cl.
| | |
|---|---|
| *B08B 1/00* | (2006.01) |
| *H04R 25/00* | (2006.01) |
| *A61F 11/00* | (2006.01) |
| *A61F 11/08* | (2006.01) |
| *B08B 17/04* | (2006.01) |
| *H04R 1/10* | (2006.01) |

(52) U.S. Cl.
CPC ............ *B08B 1/005* (2013.01); *A61F 11/006* (2013.01); *A61F 11/08* (2013.01); *B08B 17/04* (2013.01); *H04R 25/654* (2013.01); *A61F 2011/085* (2013.01); *H04R 1/1016* (2013.01); *H04R 2225/025* (2013.01)

(58) Field of Classification Search
CPC .......... H04R 2225/025; H04R 2460/15; H04R 25/658; H04R 25/456; H04R 2460/11; H04R 25/602; H04R 25/652; H04R 2225/31; H04R 1/1016; H04R 2225/021; H04R 2225/33; H04R 2499/11; H04R 25/505; H04R 25/654; H04R 2225/023; H04R 25/60; B08B 17/04; B08B 1/005
USPC .................. 381/325–328; 181/130–137, 192
See application file for complete search history.

(56) References Cited

U.S. PATENT DOCUMENTS

| 4,972,488 A | 11/1990 | Weiss et al. |
| 4,984,277 A | 1/1991 | Bisgaard et al. |

(Continued)

FOREIGN PATENT DOCUMENTS

WO      WO9709864      3/1997

*Primary Examiner* — Alexander Krzystan
*Assistant Examiner* — Julie X Dang
(74) *Attorney, Agent, or Firm* — Law Office of Alan W Cannon

(57) ABSTRACT

Guards for a space access device are configured to be attached to, as well as removed from the space access device by hand, without the need to resort to any tools to perform the attachment or the removal. A distal guard includes at least first and second filters separated by at least one convoluted pathway, and also includes outwardly extending members projecting outwardly from a base of the distal guard. A proximal guard forms at least one convoluted pathway with a cap forming a proximal end of the space access device. A pull tab provides redundancy against failure. The pull tab may be incorporated into the distal guard.

31 Claims, 32 Drawing Sheets

Related U.S. Application Data filed on Jan. 24, 2018, provisional application No. 62/627,578, filed on Feb. 7, 2018.

(56) References Cited

U.S. PATENT DOCUMENTS

| | | | |
|---|---|---|---|
| 5,327,500 A | 7/1994 | Campbell | |
| 5,606,621 A | 2/1997 | Reiter et al. | |
| 5,654,530 A | 8/1997 | Sauer et al. | |
| 5,682,020 A | 10/1997 | Oliveira | |
| 5,920,636 A | 7/1999 | Oliveira et al. | |
| 6,009,183 A | 12/1999 | Taenzer et al. | |
| 6,048,305 A | 4/2000 | Bauman et al. | |
| 6,097,823 A | 8/2000 | Kuo | |
| 6,129,174 A | 10/2000 | Brown et al. | |
| 6,135,235 A | 10/2000 | Brimhall | |
| 6,148,821 A * | 11/2000 | Falco | H04R 1/1016 128/864 |
| 6,349,790 B1 | 2/2002 | Brimhall | |
| 6,738,488 B1 | 5/2004 | Baker | |
| 7,013,016 B2 | 3/2006 | Wolf | |
| 7,016,512 B1 | 3/2006 | Feeley et al. | |
| 7,027,608 B2 | 4/2006 | Fretz et al. | |
| 7,076,076 B2 | 7/2006 | Bauman | |
| 7,421,086 B2 | 9/2008 | Bauman et al. | |
| 7,471,800 B2 | 12/2008 | Neilson | |
| 7,551,747 B2 | 6/2009 | Huynh et al. | |
| 7,792,315 B2 | 9/2010 | Mullenborn et al. | |
| 7,940,946 B2 | 5/2011 | Caldarola | |
| 7,986,803 B1 * | 7/2011 | DeKalb | H04R 1/1066 381/328 |
| 8,019,106 B2 | 9/2011 | Gunnersen et al. | |
| 8,186,478 B1 * | 5/2012 | Grason | A61F 11/08 181/175 |
| 8,284,973 B2 | 10/2012 | Gabathuler et al. | |
| 8,295,522 B2 | 10/2012 | Vestergaard et al. | |
| 8,340,335 B1 * | 12/2012 | Shennib | H04R 25/60 381/328 |
| 8,477,978 B2 | 7/2013 | Caldarola | |
| 8,842,864 B2 | 9/2014 | Rasmussen et al. | |
| 9,456,287 B2 | 9/2016 | Lindebjerg et al. | |
| 9,648,429 B2 | 5/2017 | Higgins et al. | |
| 2002/0085728 A1 | 7/2002 | Shennib et al. | |
| 2004/0258263 A1 | 12/2004 | Saxton et al. | |
| 2005/0147267 A1 * | 7/2005 | Gudmundsen | H04R 25/609 381/328 |
| 2005/0232453 A1 | 10/2005 | Fideler | |
| 2005/0238192 A1 | 10/2005 | Ford et al. | |
| 2005/0244026 A1 | 11/2005 | Nielson | |
| 2006/0067551 A1 | 3/2006 | Cartwright et al. | |
| 2008/0049961 A1 * | 2/2008 | Brindisi | H04R 1/1041 381/380 |
| 2010/0061576 A1 * | 3/2010 | Johnson | H04R 25/654 381/322 |
| 2010/0135517 A1 * | 6/2010 | Murozaki | H04R 1/1016 381/386 |
| 2010/0322453 A1 * | 12/2010 | Matsuyama | H04R 1/2857 381/380 |
| 2011/0103605 A1 * | 5/2011 | Killion | H04R 1/1083 381/72 |
| 2011/0299712 A1 | 12/2011 | Bondo et al. | |
| 2012/0250923 A1 * | 10/2012 | Beck | H04R 25/654 381/328 |
| 2014/0334651 A1 | 11/2014 | Higgins et al. | |
| 2014/0355809 A1 * | 12/2014 | Killion | H04R 1/1016 381/380 |
| 2015/0003655 A1 * | 1/2015 | Moller | H04R 25/652 381/329 |
| 2015/0139474 A1 * | 5/2015 | Henry | H04R 1/1016 381/380 |
| 2016/0057528 A1 * | 2/2016 | Trine | H04R 25/652 381/380 |
| 2016/0066110 A1 | 3/2016 | Shennib et al. | |
| 2016/0165334 A1 | 6/2016 | Grossman | |
| 2016/0269840 A1 * | 9/2016 | Dorn | H04R 25/654 |
| 2016/0323682 A1 | 11/2016 | Michel et al. | |
| 2017/0048631 A1 * | 2/2017 | Kwon | H04R 25/652 |
| 2017/0070832 A1 * | 3/2017 | Moller | H04R 25/456 |
| 2017/0085995 A1 * | 3/2017 | Tiefenau | H04R 25/656 |
| 2017/0311098 A1 | 10/2017 | Higgins et al. | |
| 2018/0084355 A1 * | 3/2018 | Kral | H04R 1/1016 |

\* cited by examiner

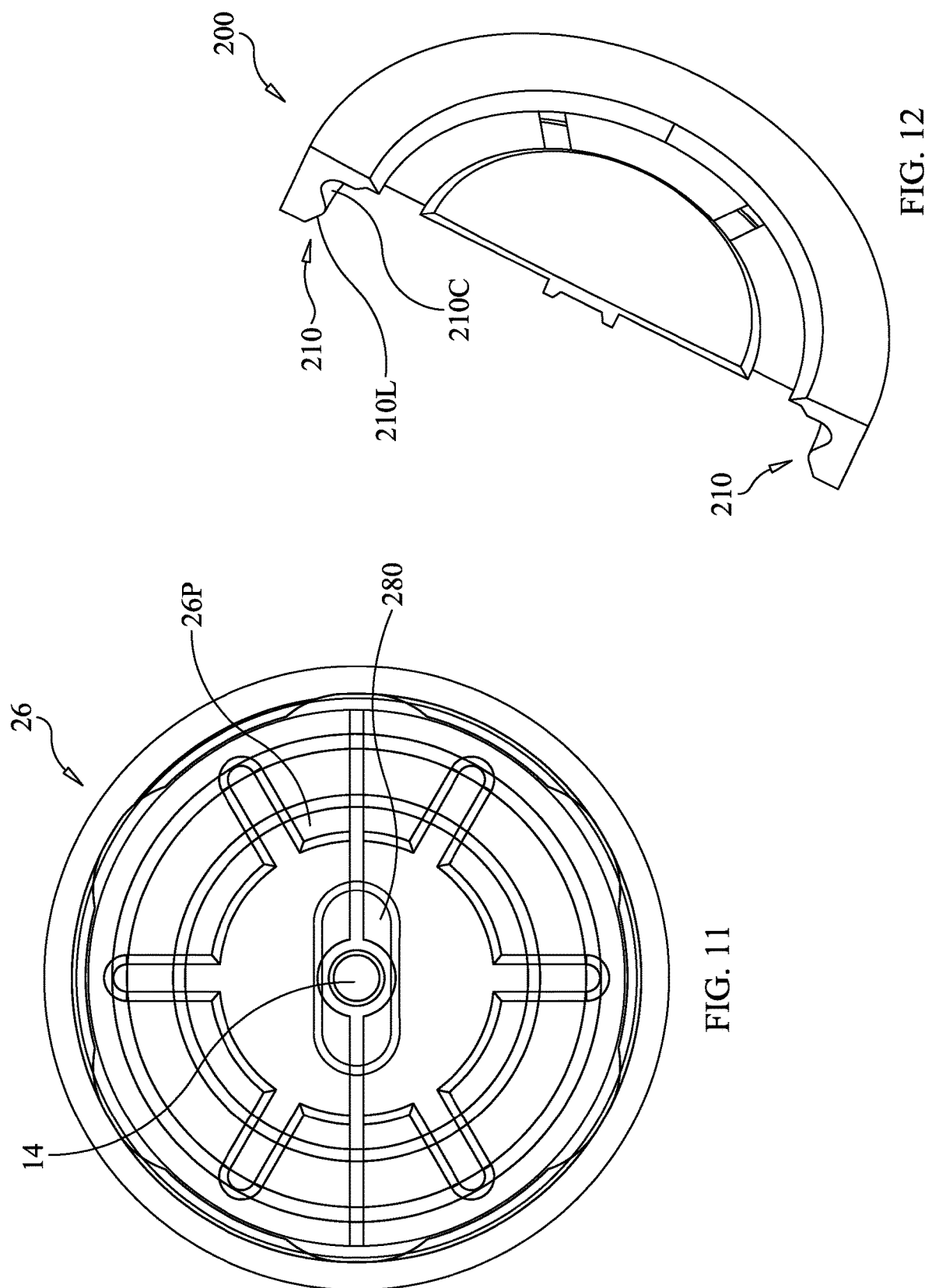

HAND REMOVABLE, CLIP ON WAX GUARDS

CROSS-REFERENCE

This application claims the benefit of U.S. Provisional Application Nos. 62/573,254, filed 17 Oct. 2017; 62/621,422, filed 24 Jan. 2018 and 62/627,578, filed 7 Feb. 2018, each of which applications is hereby incorporated herein, in its entirety, by reference thereto.

This application is being filed concurrently with application Ser. No. 16/153,353, titled "Device-Cleaning Wax Guards". Application Ser. No. 16/153,353 is hereby incorporated herein, in its entirety, by reference thereto.

FIELD OF THE INVENTION

The present invention relates to features and methods for preventing a substance from occluding acoustic openings and/or removing a substance from an acoustic opening or pathway in communication with an acoustic opening. More specifically, the present invention applies to ear wax cleaners, barriers, and/or other structures designed to manage the flow of ear wax, prevent ear wax ingress, as well as various other types of debris, to address problems associated with hearing aids, in the ear headphones and the like.

BACKGROUND OF THE INVENTION

The ear naturally secretes a substance referred to as cerumen, or more commonly referred to as "ear wax". The ear wax secreted serves a purpose of cleaning and protecting the ear canal and ear structures distal thereto, as it naturally flows in a direction toward the outer ear (Pinna). When an object such as a hearing aid or headphone (earpiece speaker) is inserted into the canal of the ear, this presents an obstruction to the natural flow of the ear wax in the ear canal. Because such an object typically includes openings or passageways necessary to permit sound to travel therethrough, these openings or passageways can become partially or completely blocked or filled with ear wax as the ear wax travels toward the outer ear. The accumulation of ear wax in the openings or passageways can lead to degradation of the sound being transmitted from the object to the middle and inner ear. Further difficulties may arise in cases where the ear wax travels through the passageways or openings to an extent where it reaches inner working components of the object, where the ear wax can do further damage, up to, and including, rendering the object nonfunctional. Wax/water may also occlude wireless power transmission to the hearing aid receiving coil.

In the case of hearing aids, the receiver, which produces the sound that is directed to the tympanic membrane, can be susceptible to progressive, gradual clogging by ear wax, resulting in progressive, gradual reduction in acoustic gain and power of the acoustic signals that are received at the tympanic membrane. When such degradation becomes severe enough, it can damage the receiver, which then requires an expensive repair or replacement of the hearing aid. The microphone end of the hearing aid is also susceptible to clogging by ear wax in the case where even the microphone end is inserted into the ear canal. Even in cases where the microphone isn't inserted completely into the ear canal, the microphone can still possibly be clogged such as when earwax on the distal end of the device gets smeared proximally to the location of the microphone, such as during handling by a user. In less severe cases, the hearing aid can be serviced to clean away the ear wax accumulation, but this may require the user going to or sending the hearing aid to a service center, which can be time consuming, expensive and inconvenient.

In many commonly available models, a filter known as an HF3 or HF4 filter (available from Amazon, CVS, and various other drug stores) is a wax guard such as a gauze, polyethylene terephthalate (PET) or stainless steel mesh insert-molded into a plastic or rubber sleeve wax guard that is used to help prevent wax from migrating into the receiver. In order to remove the HF3 or HF4 wax guard from a receptacle in the hearing aid adjacent the receiver, a tool is required to be inserted into the receptacle to access and then remove the wax guard. The act of inserting the tool into the receptacle and toward the wax guard unfortunately can drive accumulated wax further into the wax guard and potentially even force extrusion of the accumulated wax through the wax guard and out the opposite side of it, so as to drive wax into the receiver in a spaghetti-like manner. Also, because these filters are very small, (e.g., 2.2 mm diameter for HF4, 3 mm diameter for HF3) they require a certain amount of dexterity to install and remove, and may require sending a device to the manufacturer for servicing to replace such a filter. Furthermore these filters do not provide any haptic feedback as to when they have been successfully installed and accurately placed, to differentiate between instances in which they have not been properly placed or oriented and thus, have not been successfully installed.

Previous attempts at preventing or controlling ear wax buildup in the receiver of a hearing aid have included the provision of a fine mesh screen in the audio pathway between the receiver and the outside of the hearing aid. Even in instances where the mesh is very fine, such as where openings of the mesh are on the order of 50 to 60 micrometers diameter, ear wax was not prevented from traveling through these openings, due to the capillary action of the surfaces of the through holes (openings) on the ear wax.

U.S. Pat. No. 4,972,488 to Weiss et al. recognizes the problem of coarse meshes being incapable of effectively preventing ear wax from migrating across a coarse mesh screen barrier to the receiver. Weiss et al. further describes that if a barrier is made with a screen size sufficiently small to protect the receiver from wax migration, the screen holes will eventually be clogged by the wax. To address these problems, Weiss et al. provides projections that define a tortuous pathway for wax to travel. As a second line of defense, Weiss et al. may provide a screen that may act as a wax catheter for wax particles that may pass through the tortuous pathway barrier. The barrier is interconnected between the receiver and the acoustic output port. Specialized tools are required for installation and removal of the barrier. In another embodiment, a threaded plug is installed adjacent the receiver. This embodiment is removable with the use of a screwdriver-like instrument.

U.S. Pat. No. 4,984,277 Bisgaard et al. discloses a protection element for an all-in-the-ear hearing aid, in which the protection element consists of a sound conduction tube and a filter element arranged to be mounted on the sound conduction tube. There is no disclosure or suggestion that the sound conduction tube can be removed or replaced in the case that it accumulates an unacceptable amount of wax. Although the filter element can be replaced, this requires a specialized tool/dispenser to perform these functions.

U.S. Pat. No. 7,013,016 to Wolf discloses an ear wax guard that can be installed into, and removed from a sound tube connected to a receiver of a hearing aid. Because the force required to be applied to the guard is applied almost linearly throughout the entire installation procedure, there is no haptic feedback provided to allow the installer to recognize when the installation process has been completed, or whether the installation was successfully completed by a proper installation. A tool is required for removal of the guard, such as a tool that can engage a bow provided with the guard.

US Patent Application Publication No. 2017/0311098 to Higgins et al. discloses a hearing assistance device that includes an acoustic recess positioned to collect wax before it reaches the microphone of the device. Wax can be cleaned from the recess when the battery door is opened. Higgins et al. also generally mentions a self-cleaning wiper arm to remove wax and debris, but does not appear to show such an arm in any of the drawings or provide any further detail about the structure of such an arm, where it would be located, or even how it functions.

US Patent Application Publication No. 2016/0165334 to Grossman discloses an acoustic device, configured to be disposed at least partially within the ear, having a sleeve that can be removed from a hard inner shell so that the channels of the sleeve can be cleaned. Even with removal of the sleeve from the hard inner shell, it appears that the task of cleaning out the channels is less than convenient.

There is a continuing need for wax guards that can be easily managed by a user of a hearing aid device, in ear speaker, or other space access device, so that changing of such wax guards can be readily accomplished by the user.

There is a continuing need for wax guards that can be easily installed and removed by hand, without the need for any tools.

There is a continuing need to wax guards and methods of removing and installing the same that do not run the risk of exposing a protected component during the process of installing or removing such wax guards.

There is a continuing need for the provision of wax guards in a configuration that can be easily handled by a user for installation and removal.

There is a continuing need for wax guards that provide haptic feedback to the person installing, to help confirm when a wax guard has been successfully installed.

There is a continuing need for wax guard solutions that have a longer service life, compared to products currently available, so that they can be used for a relatively longer period of time prior to needing to replace them. It would be desirable to provide wax guards that can be serviced without removal or replacement, to extend the service life thereof.

There is a continuing need for wax guards that can be at least partially cleaned or cleared without the need for removal or immediate replacement.

There is a continuing need for wax guard configurations in which at least a portion of a pathway along which the wax can accumulate can be cleared without the need to remove the wax guard.

SUMMARY OF THE INVENTION

In one aspect of the present invention, guards are provided for management of the flow of ear wax, to prevent ear wax ingress, as well as various other types of debris, such as water, dust, dirt, lint, sunscreen, and/or lotion, etc. to a device that is partially or wholly inserted into an ear canal.

In one aspect of the present invention, a guard for a space access device configured to output air flow through a distal end portion thereof includes: a base comprising a longitudinal axis and an outer surface; a connector at a proximal end of the base, the connector configured to form a secure connection with a distal end of the space access device; a first filter at a distal end portion of the base; a second filter at a proximal end portion of the base, the second filter being located within an opening defined by the connector; and at least one convoluted pathway within the base, in fluid communication with the first and second filters; wherein the guard is configured to be attached to and removed from the space access device by hand, without the need for any tool.

In at least one embodiment, the connector is configured to form a snap fit with the distal end of the space access device, and to provide haptic feedback to a user installing the guard on the space access device by hand.

In at least one embodiment, the guard further includes a reservoir in fluid communication between the at least one convoluted pathway and the second filter, wherein a largest cross-sectional dimension of the reservoir is at least twice a largest cross-sectional dimension of the at least one convoluted pathway.

In at least one embodiment, the guard includes an adjustable securing mechanism disposed on at least a portion of the base, the securing mechanism being configured to contact a surface of an internal space or opening into which the securing mechanism is inserted; the adjustable securing mechanism being configured for positioning and maintaining the base at a distance from a location along the internal space or opening; wherein a least a portion of the adjustable securing mechanism being configured to transition from a first state to a securing state when inserted into the internal space or opening, the securing state comprising at least a portion of the adjustable securing mechanism being constrained to have a smaller cross-sectional diameter relative to a cross-sectional diameter in the first state; and wherein the adjustable securing mechanism comprises a plurality of members configured to contact a wall of the internal space; and wherein the guard is configured to be disconnected from the space access device by holding the space access device in one hand of a user and pulling on one or more of the members.

In at least one embodiment, the guard further includes a pull tab extending from the base, the pull tab having a length sufficient so that at least a proximal end portion of the pull tab extends out of the ear canal when the guard is operatively attached to the space access device and the space access device is installed in the ear canal in an operative position.

In at least one embodiment, the pull tab comprises at least two legs, each leg being integrally attached to the guard to provide redundant features for more reliability against failure.

In at least one embodiment, a slot is formed between two of the legs, the slot configured to facilitate airflow therethrough.

In at least one embodiment, the legs are integrally joined together at proximal end portions thereof.

In at least one embodiment, the pull tab is made of a material that is stronger in tensile strength than a material from which the members are made.

In at least one embodiment, the pull tab includes a grip enhancement feature provided on a proximal end portion thereof.

In at least one embodiment, the pull tab is molded to the connector.

In at least one embodiment, the connector is formed of a first material and the pull tab is formed of a second material, wherein the first material is stiffer than the second material.

In at least one embodiment, the pull tab is curved to conform to a space or opening into which the space access device is inserted.

In at least one embodiment, the pull tab has a double curvature; wherein a distal portion of the pull tab curves toward the base; and wherein a proximal portion of the pull tab curves away from the base.

In at least one embodiment, the proximal portion is curved and dimensioned to rest in the Intertragal Notch of the Pinna when the space access device in inserted in an ear canal.

In at least one embodiment, the plurality of members are molded from silicone and the connector comprises a plastic having a hardness greater than a hardness of the silicone.

In at least one embodiment, the guard includes a third filter located between the first and second filters and in fluid communication with the first and second filters.

In at least one embodiment, the at least one convoluted pathway is located between the first and third filters, the guard further includes at least one second convoluted pathway between the third and second filters.

In at least one embodiment, opposing angular surfaces are provided in the at least one convoluted pathway to discourage capillary action on wax in the convoluted pathway.

In at least one embodiment, a perimeter of an opening to the at least one convoluted pathway is formed by a first perimeter portion formed by a portion of a perimeter of a first of the opposing angular surfaces and a second perimeter portion formed by a portion of a perimeter of a second of the opposing angular surfaces.

In at least one embodiment, the perimeter of the opening is completely formed by the first and second perimeter portions, and wherein each of the first and second perimeter portions are continuous portions.

In another aspect of the present invention, a guard for a space access device configured to receive air flow through a proximal end portion thereof includes: a base comprising a proximal end, a distal surface and a connector extending distally from the distal surface; and openings extending through the base from the proximal end to the distal surface; wherein the guard is configured to be attached to and removed from the space access device by hand, without the need for any tool.

In at least one embodiment, the connector is configured to flex relative to a portion of the space access device, as it is being connected thereto or removed therefrom and to provide haptic feedback to a user installing the guard on the space access device by hand.

In at least one embodiment, the guard further includes at least one convoluted pathway formed in the distal surface and in fluid communication with at least one of the openings.

In at least one embodiment, the base is circular in cross-section.

In at least one embodiment, the connector comprises a lip extending radially inwardly and a channel located between the lip and the distal surface.

In at least one embodiment, the connector further comprises weakened sections that facilitate flexing.

In another aspect of the present invention, a space access device includes: a shell having a proximal end portion and a distal end portion; and a distal guard comprising: a base comprising a base proximal end portion; a base distal end portion; an outer surface; a connector at the base proximal end portion attachable to the distal end portion of the shell; a first filter in the base distal end portion; a second filter in the base proximal end portion, within a first opening defined by the connector; and at least one convoluted pathway within the base, in fluid communication with the first and second filters; wherein the distal guard is configured to be attached to and removed from the shell by hand, without the need for any tool.

In at least one embodiment, the shell includes a distal tip extending from a distal end surface of the distal end portion, the distal tip configured and dimensioned to mate with the connector.

In at least one embodiment, the connector forms a snap fit with the distal tip.

In at least one embodiment, the distal guard further comprises a plurality of outwardly extending members integrally formed with the base and outwardly extending therefrom.

In at least one embodiment, the space access device further includes a proximal guard attachable to the proximal end portion of the shell, the proximal guard comprising: a second base comprising a proximal end, a distal surface and a second connector located distally of the distal surface; and at least one second opening extending through the second base and in fluid communication with at least one second convoluted pathway configured to be in fluid communication with the proximal end portion of the space access device when the second base is attached to the proximal end portion of the shell; wherein the proximal guard is configured to be attached to and removed from the proximal end portion of the shell by hand, without the need for any tool.

In at least one embodiment, the proximal end portion of the shell comprises a cap; wherein the cap comprises a central opening that overlies a microphone port contained in the shell; and wherein a proximal surface of the cap and the distal surface of the second base are configured to form the at least one second convoluted pathway between the at least one second opening and the central opening when the proximal guard is connected to the cap.

In at least one embodiment, the cap further comprises a mating connector configured and dimensioned to mate with the second connector.

In at least one embodiment, the second connector forms a snap fit with the mating connector.

In at least one embodiment, the cap tapers down from a distal end of the cap to the mating connector thereby forming a tapered surface; wherein a gap is formed between a distal end of the second connector and the tapered surface when the second connector and the mating connector are mated, such that an edge of the distal end is exposed, wherein the edge can be readily engaged by fingers of a user to apply force thereto so as to disconnect the proximal guard from the cap without the use of any tools.

In at least one embodiment, the space access device comprises an in-the-ear hearing aid.

In at least one embodiment, the space access device comprises an earpiece speaker.

In another aspect of the present invention, a method of making a guard includes: providing a connector configured to form a secure connection with a distal end of a space access device, wherein the connector comprises a first filter located within an opening defined by the connector; integrally joining a first modular guard component to the connector, wherein the first modular guard component comprises a first base, a second filter at a distal end portion of the first base; and at least one convoluted pathway within the first base, in fluid communication with the first and second filters.

In at least one embodiment, the first base further comprises a first reservoir in fluid communication between the at least one convoluted pathway and the first filter, wherein a largest cross-sectional dimension of the first reservoir is at least twice a largest cross-sectional dimension of the at least one convoluted pathway.

In at least one embodiment, the guard is configured to be attached to and removed from the space access device by hand, without the need for any tool.

In at least one embodiment, the method further includes integrally joining a second modular guard component to the first modular guard component, wherein the second modular guard component comprises a second base, a third filter at a distal end portion of the second base; and at least one second convoluted pathway within the second base, in fluid communication with the third and second filters.

In at least one embodiment, the first modular guard component comprises a plurality of first members extending radially outwardly from the first base and the second modular guard component comprises a plurality of second members extending radially outwardly from the second base.

In at least one embodiment, upon the integrally joining the second modular guard component to the first modular guard component, the plurality of second members are oriented in gaps between the plurality of first members when viewed in a direction along a longitudinal axis of the guard.

In at least one embodiment, the first and second members are slotted to allow air flow therethrough, the first modular component further comprising a pull tab having a length greater than a length of any of the plurality of first members, the pull tab also being slotted.

In another aspect of the present invention, a method of servicing a space access device includes: securing a main body of the space access device with one hand; using a second hand to align a connector of a distal guard with a distal mating connector on the main body; and connecting the distal guard to the main body by hand, without the use of any tools.

In at least one embodiment, the connecting comprises pulling one or more outwardly projecting members of the distal guard, while pushing on or maintaining a position of the main body.

In at least one embodiment, the connecting comprises performing a snap fit.

In at least one embodiment, the method further includes replacing the distal guard, wherein the replacing comprises: removing the distal guard from the main body, by applying opposing forces to the distal guard and the main body via the second hand and the one hand, respectively, without the use of any tools; selecting a second distal guard; securing the main body of the space access device with the one hand; using the second hand to align a connector of the second distal guard with the distal mating connector on the main body; and connecting the second distal guard to the main body by hand, without the use of any tools.

In at least one embodiment, the method further includes securing a main body of the space access device one hand; using a second hand to align a connector of a proximal guard with a proximal mating connector on the main body; and connecting the proximal guard to the main body by hand, without the use of any tools.

In at least one embodiment, the method further includes replacing the proximal guard, wherein the replacing comprises: removing the proximal guard from the main body, by applying opposing forces to the proximal guard and the main body by hand, without the use of any tools; selecting a second proximal guard; securing the main body of the space access device with one hand; using the second hand to align a connector of the second proximal guard with the proximal mating connector on the main body; and connecting the second proximal guard to the main body by hand, without the use of any tools.

In another aspect of the present invention, a pull tab for a space access device includes: a connector configured to form a secure connection with a distal end of the space access device; and an elongate member attached to and extending from the connector, the elongate member having sufficient tensile strength such that the connector can be detached from the space access device, without the use of a tool, by pulling on the elongate member in a first direction, while holding the space access device stationary or pulling in an opposite direction on the space access device.

In at least one embodiment, the elongate member comprises at least two legs, each leg being integrally attached to the connector to provide redundant features for more reliability against failure.

In at least one embodiment, the elongate member has a length sufficient so that at least a proximal end portion of the elongate member extends out of the ear canal when the connector is operatively attached to the space access device and the space access device is installed in the ear canal in an operative position.

In at least one embodiment, the pull tab further includes a slot formed between two of the legs, the slot configured to facilitate airflow therethrough.

In at least one embodiment, the elongate member is molded to the connector.

In at least one embodiment, the connector is formed of a first material and the elongate member is formed of a second material, wherein the first material is stiffer than the second material.

In at least one embodiment, the elongate member is curved to conform to a space or opening into which the space access device is inserted.

In at least one embodiment, the elongate member has a double curvature; wherein a distal portion of the elongate member curves toward the connector; and wherein a proximal portion of the elongate member curves away from the connector.

In at least one embodiment, the proximal portion is curved and dimensioned to rest in the Intertragal Notch of the Pinna when the space access device is inserted in an ear canal.

In at least one embodiment, the pull tab is provided in combination with a guard comprising: a base attached to or integral with the connector, the base comprising a longitudinal axis and an outer surface; an adjustable securing mechanism disposed on at least a portion of the base, the securing mechanism being configured to contact a surface of an internal space or opening into which the securing mechanism is inserted; the adjustable securing mechanism being configured for positioning and maintaining the base at a distance from a location along the internal space or opening; wherein a least a portion of the adjustable securing mechanism being configured to transition from a first state to a securing state when inserted into the internal space or opening, the securing state comprising at least a portion of the adjustable securing mechanism being constrained to have a smaller cross-sectional diameter relative to a cross-sectional diameter in the first state; and wherein the adjustable securing mechanism comprises a plurality of outwardly extending members configured to contact a wall of the internal space.

In at least one embodiment, a length of the elongate member is greater than a length of any of the outwardly extending members.

In at least one embodiment, the guard is configured to be disconnected from the space access device by holding the space access device in one hand of a user and pulling on at least one of the elongate member and the outwardly extending members.

In at least one embodiment, the combination further includes: a first filter at a distal end of the base; a second filter at the proximal end of the base, the second filter being located within an opening defined by the connector; and at least one convoluted pathway within the base, in fluid communication with the first and second filters; wherein the guard is configured to be attached to and removed from the space access device by hand, without the need for any tool.

In at least one embodiment, the elongate member is made of a material that is stronger in tensile strength than a material from which the outwardly extending members are made.

In at least one embodiment, the elongate member and the outwardly extending members are slotted to facilitate air flow therethrough.

In at least one embodiment, lengths of slots of the slotted elongate member and the outwardly extending members are equal.

These and other features of the invention will become apparent to those persons skilled in the art upon reading the details of the devices, systems and methods as more fully described below.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

FIG. 11 is a proximal end view of the cap shown in FIG. 2.

FIG. 12 is a sectional view of the guard shown in FIGS. 9-10.

DETAILED DESCRIPTION OF THE INVENTION

Figure 1:
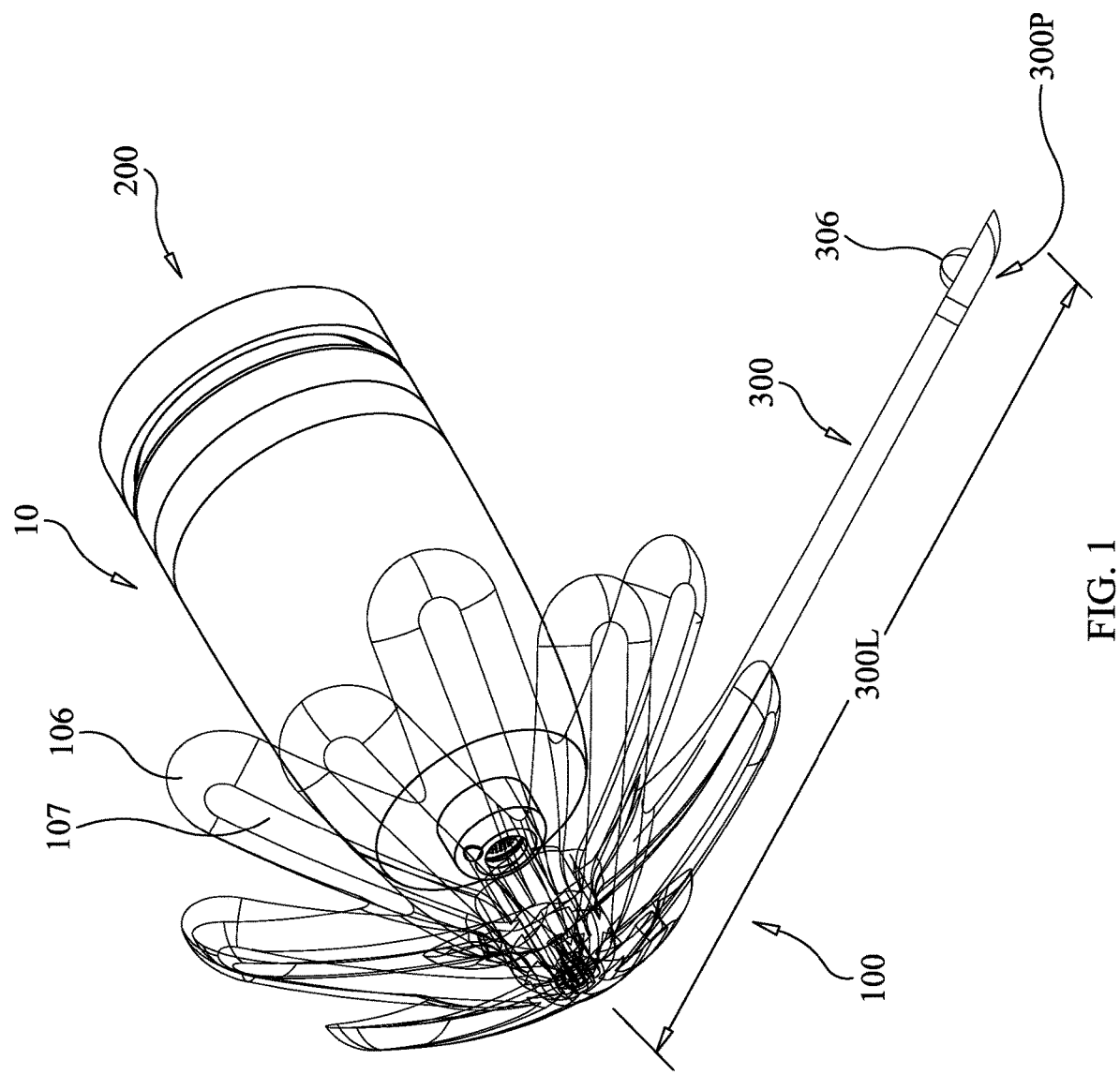
FIG. 1 is a perspective view of a space access device that includes wax management guards, according to an embodiment of the present invention.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a blade" includes a plurality of such blades and reference to "the convoluted pathway guard" includes reference to one or more convoluted pathways and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

The term "space access device", as used herein, means a device that is designed and adapted to be inserted into or around a space or opening that is commonly in the presence of a viscous/potentially occluding substance, including but not limited to anatomical or biological and non-biological devices that are designed and adapted to be inserted into a space or opening, such as an ear canal, nasal conduit, esophagus, airway, gastro-intestinal tract, blood vessel, pipe, or conduit.

The term "outwardly projecting member" or "outwardly extending member", as used herein, means and includes any projection extending from a base member, including, without limitation, fins, fibers, bristles, blades, petals, protrusions, ridges, vanes, grooves, bubbles, balloons, hooks, looped structure, disks and/or tubes.

The terms "headphone" and "headset" are used interchangeably herein and mean and include a listening device that is adapted to receive transmitted sound via wireless or wired communication means. As is well known in the art, conventional headphones and headsets typically include one or more speakers and/or sound production components, which can be in the form of one or two earpieces (often referred to as "ear plugs" or "ear buds").

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates, avians, domestic household or farm animals, such as cats, dogs, sheep, goats, cattle, horses and pigs; laboratory animals, such as mice, rats and guinea pigs; reptiles, zoo and wild animals, and the like. One or more of the components described herein may be coated with or otherwise provided with one or more pharmacological agents.

The terms "pharmacological agent", "active agent", "drug" and "active agent formulation" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The term "wiper" refers to a structure that is operable to move a wax deposit from one location to another and can refer to a blade that has clearance with respect to the surface on which the wax deposit is being moved, a blade that has no clearance with respect to the surface, multiple blades of either type, a block, one or more beams, or other structure that effectively functions to move the wax deposit.

The following disclosure is provided to further explain in an enabling fashion the best modes of performing one or more embodiments of the present invention. The disclosure is further offered to enhance an understanding of and appreciation for the inventive principles and advantages thereof, rather than to limit in any manner the invention. The invention is defined solely by the appended claims including any amendments made during the pendency of this application and all equivalents of those claims as issued.

As will readily be appreciated by one having ordinary skill in the art, the present invention substantially reduces or eliminates the disadvantages and drawbacks associated with conventional wax management systems for in the ear devices.

In overview, one aspect of the present invention is directed to wax management devices that can be readily employed with devices and systems that are configured to be inserted in one or more biological spaces or openings, such as an ear canal.

Referring now to the drawings, FIG. 1 is a perspective view of a space access device 10 that includes wax management guards 100 and 200 that can be installed as well as removed, by hand, by a user of the device 10, without the need to resort to any tools. Of course, the fact that the guards 100 and 200 can be installed and removed without the need to use any tools does not prevent the use of one or more tools for performing these tasks, if preferred. In the embodiment of FIG. 1, the space access device 10 is an in the ear hearing aid device, but the present invention is not limited to hearing aid devices, as other space access devices may be configured with one or both of guards 100, 200 according to other embodiments of the present invention. For example, an in the ear headset speaker (sometimes referred to as an "ear bud") can be configured with guard 100. Other non-limiting examples of space access devices that can employ one or both guards 200 include otoscopes (ENT (ear, nose and throat) scopes), stethoscopes, all types of headphones (not just earbuds—over the ear style, in-ear monitors, etc.), security headsets, BLUETOOTH® audio headsets, other types of wearable devices with speakers and/or microphones that could get clogged, such as smart watches, phones, etc.

Figure 2:
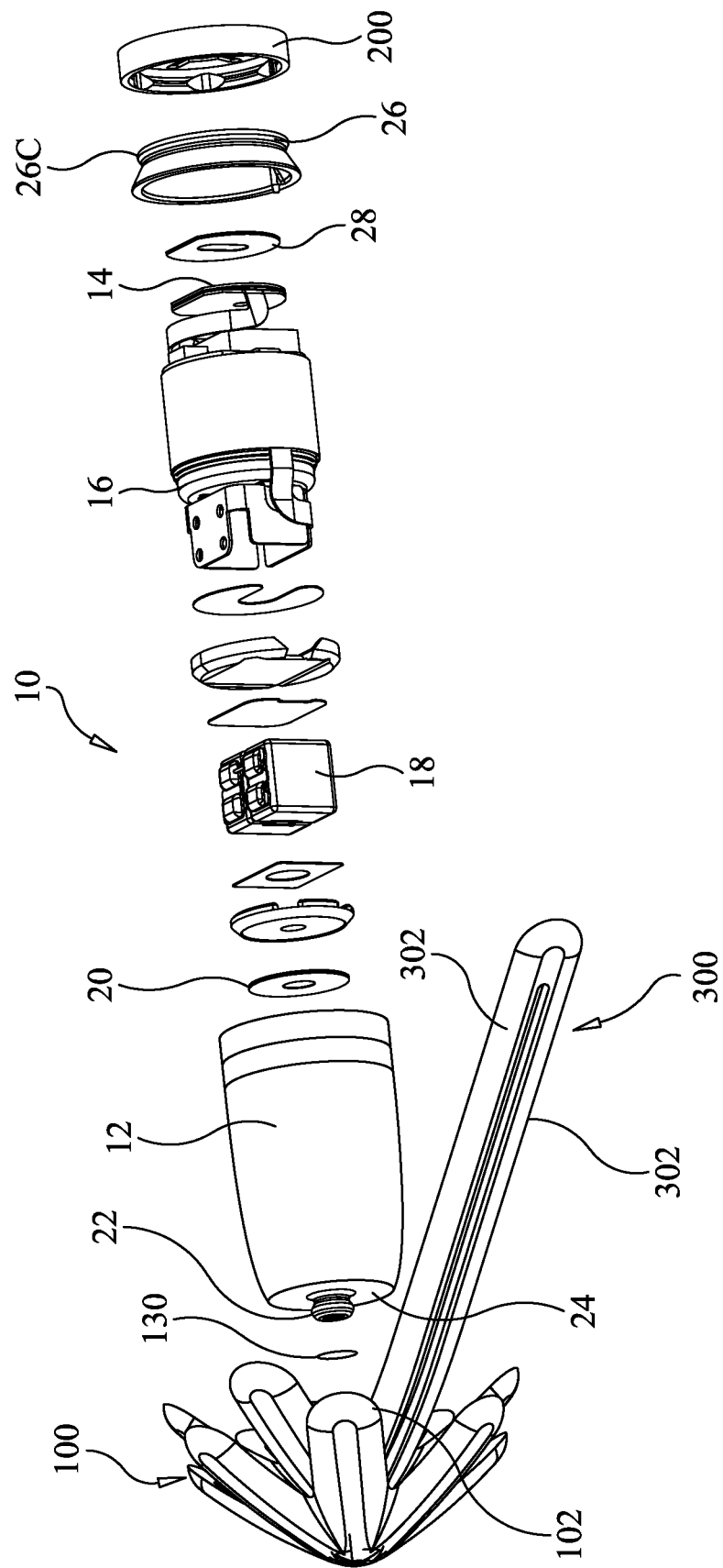
FIG. 2 is an exploded view of FIG. 1.

FIG. 2 is an exploded view of the space access device 10 of FIG. 1. As noted with regard to FIG. 1, in this embodiment space access device 10 comprises an in the ear hearing aid. Space access device 10 includes a housing or shell 12 which may house electronic components and provides a structure to which guards 100, 200 are attachable and removable. Electronic components that may be housed by the shell/housing 12 may include, without limitation, a microphone 14, a battery 16, a receiver 18, which may include a sound processor, and/or an actuator. The battery 16 or any other energy storage system may provide power to the other electronic components. The microphone 14 may receive and/or collect sound. The sound processor may be used for sound amplification. The actuator may be used for sound transmission to a passive amplifier. In the embodiment shown in FIGS. 1-2, the receiver 18 is contained within the distal end portion of the housing/shell 12 and the central portion of the housing/shell 12 may house a sound processor. The microphone 14 opens through the proximal end of the housing/shell 12. In the embodiment of FIGS. 1-2, shell 12 is substantially cylindrically-shaped, but tapers to a relatively smaller diameter at the distal end portion so as to be generally "bullet-shaped", although other shapes, such as cylindrical or other configuration could be substituted, although less desired as of this filing. A receiver filter 20 may optionally be provided within the shell/housing 12 between the distal end of the shell/housing and the receiver 18, so as to provide an additional level of protection against moisture and/or wax reaching the receiver 18, as well as to provide dirt, dust and debris protection, and visually cover up the receiver port to improve aesthetics. The filter 20 may be made of PET monofilaments woven into a mesh pattern, covered in a hydrophobic coating, which is then laminated with pressure sensitive adhesive (PSA) on either side and stuck to a shell/dampener during assembly. In one specific embodiment the pores of the filter 19 um squares, but this may vary depending on acoustic performance desired. A metal mesh (e.g., woven, stamped, etched and/or/drilled, etc.) could be used in lieu of plastic mesh. A membrane-style filter made of expanded polytetrafluoroethylene (ePTFE) could also be used in lieu of a mesh.

The shell/housing 12 further comprises a distal tip 22 that extends distally of the distal surface 24 of the shell. The distal tip 22 includes one or more openings (not shown in FIG. 2) that allow air flow/sound to pass therethrough. The distal tip 22 is configured to mate with a mating connector 102 of the guard 100, as described in more detail below.

Figure 3:
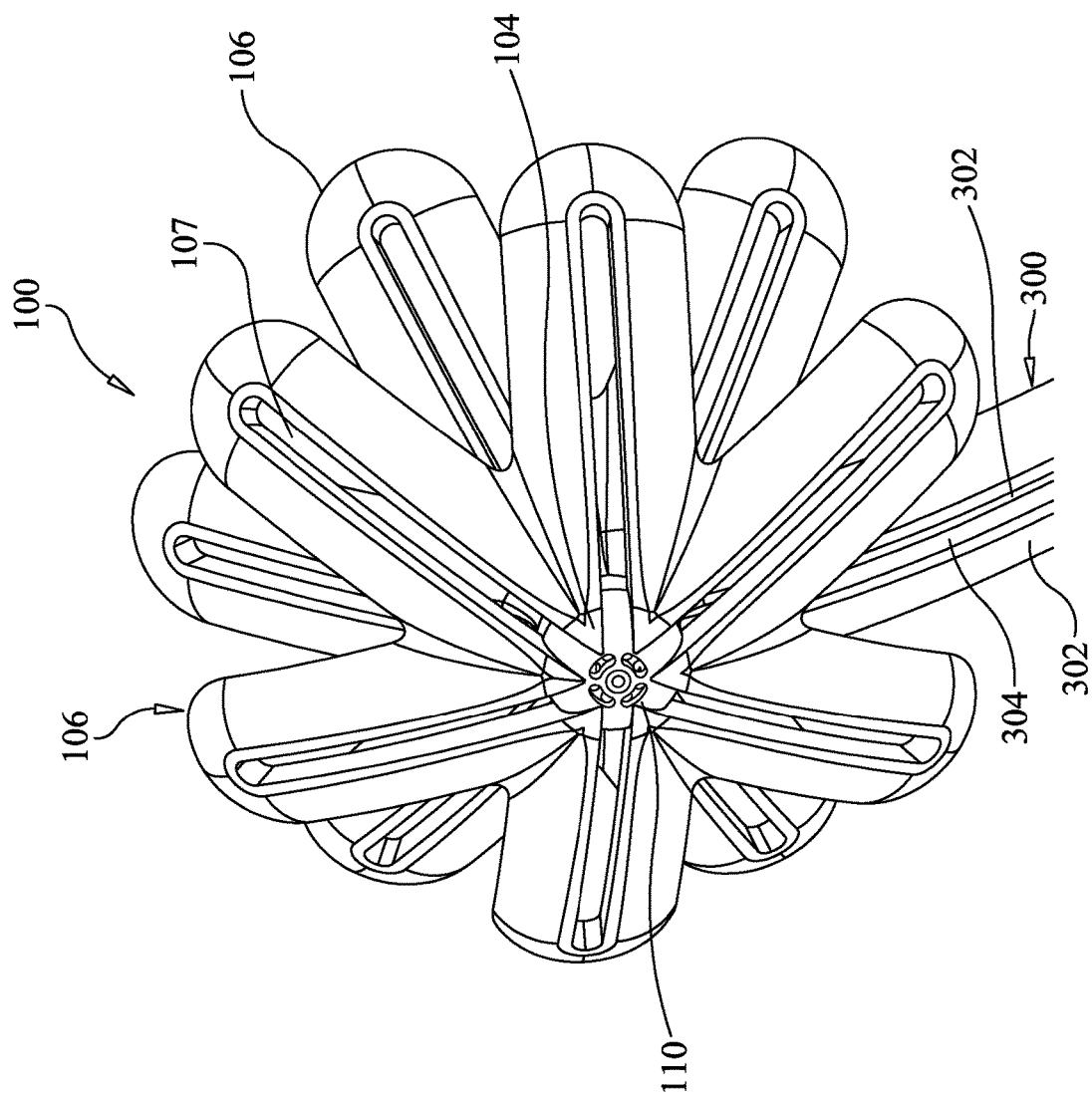
FIG. 3 shows a distal end view of a guard according to an embodiment of the present invention.

At the proximal end of the shell/housing 12, a cap 26 is configured to be fitted to and seal off the open proximal end of the shell/housing, thereby forming the proximal end of the housing 12 upon such joining. Cap 26 contains at least one opening (not shown in FIG. 2) that is designed to allow air flow/sound to pass therethrough so as to reach the microphone 14. Optionally a microphone filter 28 may be provided within the shell/housing 12 between the microphone 14 and the cap 26, so as to provide an additional level of protection against moisture and/or wax reaching the microphone 14. The microphone filter 28 may be constructed in the same way and from the same materials as the filter 20 described above. The proximal end portion of the cap 26 is provided with a connecting feature such as a shoulder or lip or equivalent 26C that is configured to mate with a mating connector of guard 200, which is not clearly shown in FIG. 2, but is described in more detail below FIG. 3 shows a distal end view of guard 100 according to an embodiment of the present invention. Guard 100 includes a base 104 that extends longitudinally from the distal end of guard 100 to the mating connector 102. Flexible fibers 106 extend radially outwardly from base 104 as shown in FIG. 3. Flexible fibers 106 are outwardly projecting members that may include, but are not limited to, one or more of fins, bristles, blades, rods, vanes, skirts, protrusions, ridges, grooves, bubbles, balloons, hooks, looped structure, disks, and/or tubes and/or combinations of these. For example, projecting members may include a central bristle or rod flanked by vanes or blades. In the embodiment shown in FIG. 3, the flexible fibers 106 comprise vanes having slots or gaps 107 extending longitudinally therealong to facilitate airflow therethrough. However, the present invention is not limited to only this design of flexible fibers 106. Further examples of flexible fibers 106 that may be employed are described in U.S. application Ser. No. 15/785,731, filed Oct. 17, 2017, and U.S. Pat. Nos. 8,457,337; 9,167,363; 9,344, 819; 9,826,322; 8,577,067; 9,060,230 and 9,866,978, each of which is hereby incorporated herein, in its entirety, by reference thereto.

Together, the base 104 and outwardly projecting members 106 function as a securing mechanism that has a flexible compressible mechanism. When connected to the housing 12 and inserted into an ear canal, the flexible compressible mechanism can remain permeable to both airflow and sound to maintain an open ear canal throughout the securing mechanism. The guard 100 therefore additionally functions as a securing mechanism configured to secure the space access device 10 within the ear canal. The flexible fiber 106 assembly is configured to be compressible and adjustable in order to secure the device 10 within an ear canal. The flexible fiber assembly may contact an ear canal surface when the device 10 is in use, and provide at least one airflow path through the hearing aid or between the hearing aid and ear canal surface. The flexible fibers 106 are preferably made from a medical grade silicone, which is a very soft material as compared to hardened vulcanized silicone rubber. The flexible fibers 106 and base 104 may be made from a compliant and flexible material selected from a group including i) silicone, ii) rubber, iii) resin, iii) elastomer, iv) latex, v) polyurethane, vi) polyamide, vii) polyimide, viii) silicone rubber, ix) nylon and x) combinations of these, but not a material that is further hardened including volcanized rubber. Note, the plurality of fibers being made from the compliant and flexible material allows for a more comfortable extended wearing of the hearing assistance device in the ear of the user.

The outwardly projecting members 106 are compressible, for example, between two or more positions, and may act as an adjustable securing mechanism to the inner ear. The plurality of outwardly projecting members 106 may be compressible to a collapsed position in which an angle that the outwardly projecting members 106, in the collapsed position, extend outwardly from the base 104 to the surface of the ear canal is smaller than when the plurality of outwardly projecting member 106 are expanded into an open position. Note, the angle of the outwardly projecting members is measured relative to the housing 12 when the guard 100 is connected thereto. The outwardly projecting members 106 are compressible to collapsed positions expandable to adjustable open positions, where the securing mechanism is expandable to the adjustable open position at multiple different angles relative to the ear canal in order to contact a surface of the ear canal so that one manufactured instance of the hearing assistance device can be actuated into the adjustable open position to conform to a broad range of ear canal shapes and sizes.

The flexible fiber assembly may contact an ear canal surface when the hearing aid is in use, and provide at least one airflow path through the hearing aid or between the hearing aid and ear canal surface. In an embodiment, the hearing assistance device may be a hearing aid, or simply an ear bud in-ear speaker, or other similar device that boosts human hearing range frequencies. The body of the hearing aid may fit completely in the user's ear canal, safely tucked away with merely a pull tab 300 coming out of the ear. Because the flexible fiber assembly suspends the hearing aid device in the ear canal and doesn't plug up the ear canal, natural, ambient low (bass) frequencies pass freely to the user's eardrum, leaving the electronics-containing portion to concentrate on amplifying mid and high (treble) frequencies. This combination gives the user's ears a nice mix of ambient and amplified sounds reaching the eardrum. The ability to let air flow in and out of the ear further makes the hearing assistance device incredibly comfortable and breathable. And because each individual flexible fiber 106 in the bristle assembly exerts a miniscule amount of pressure on the ear canal, the hearing assistance device will feel like it is merely floating in the ear while staying firmly in place.

Figure 4A:
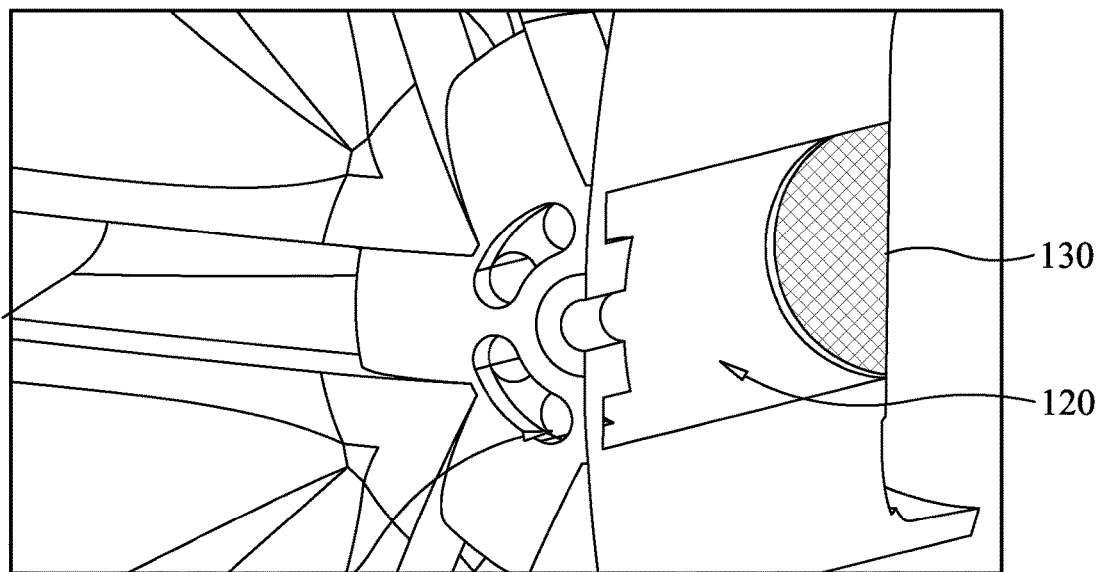
FIGS. 4A-4C are partial, longitudinal sectional views of the guard of FIG. 3.
Figure 4B:
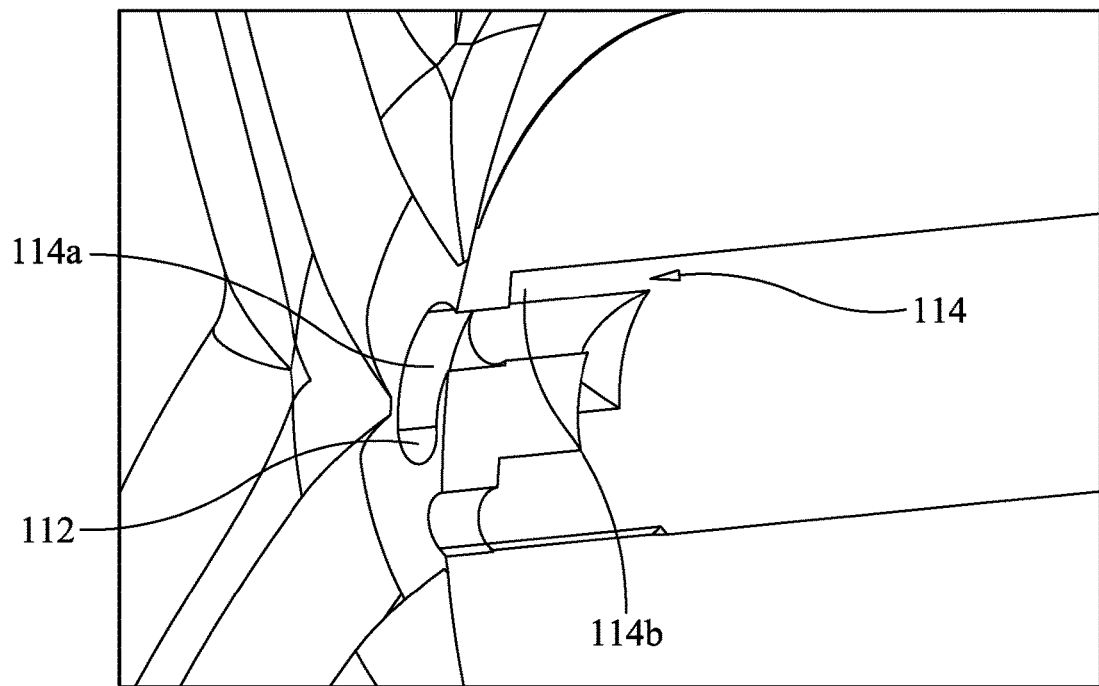
Figure 4C:
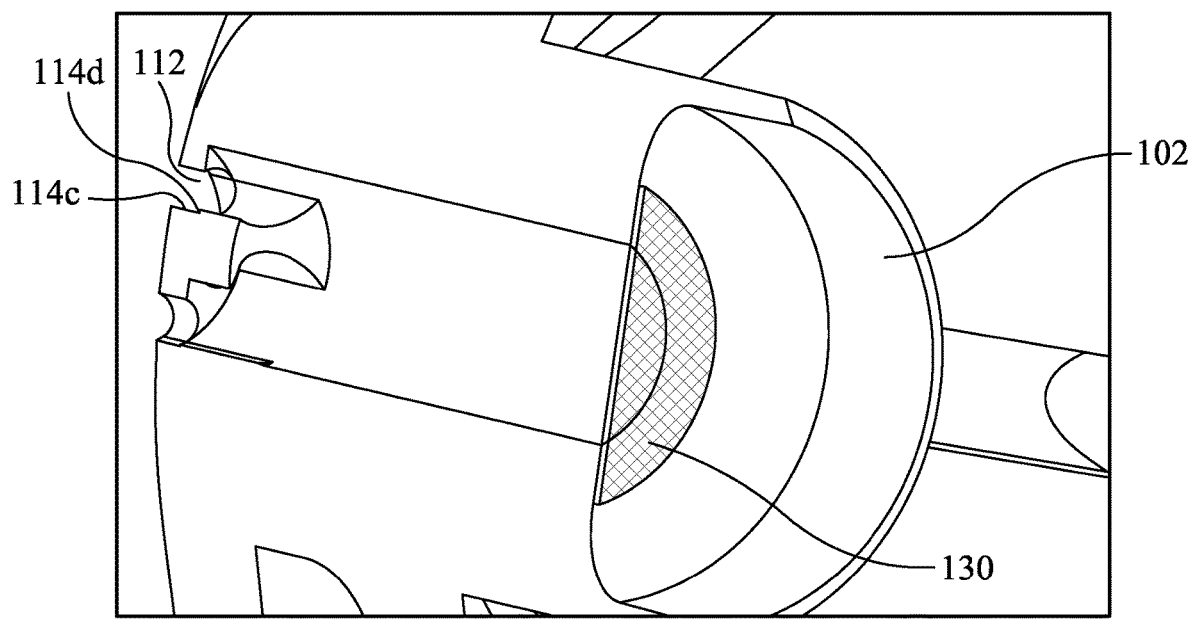

Guard 100 is further provided with a filter 110 located on a distal face of the base 104 of the guard 100. Filter 110 is configured to allow air flow/sound therethrough, while discouraging the inflow of wax and moisture. The openings 112 of the filter 110 may have a diameter in the range from about 0.05 mm to about 0.5 mm, typically in the range from 0.10 mm to 0.35 mm. In one particular embodiment, openings 112 had a diameter of 0.20 mm. FIGS. 4A-4C are partial, longitudinal sectional views of the guard 100 illustrating convoluted pathways 114 that are in fluid communication with the openings 112 of the filter 110, reservoir 120 and second filter 130. For example, in FIG. 4A, as sound/air passes through opening 112 of filter 110 it is redirected by a right angle (but could be an angle within a range of 30 to 150 degrees, or 60 to 120 degrees, or other range) along the pathway 114a portion of the convoluted pathway, and is again redirected along pathway 114b (by a right angle in this embodiment, but could be another angle). In one non-limiting embodiment, the area of the bean-shaped cutout 114a was about 0.094248 mm$^2$ and the holes 112 connecting 114a/114b had a diameter of about 0.2 mm, although these dimensions may vary. The bean shape is a 45-degree spacing of two of these holes 112, with an outer bean radius of about 0.50 mm and an inner bean radius of about 0.30 mm. The dimensions of 114b may be the same, with the bean shape being offset so that holes 112 overlap, but the bean shapes 114a, 114b do not, so as to establish the convoluted pathway. Additional convolutions of the pathway may be provided to those shown, or alternatively, only one convolution 114a may be used. Preferably at least two convolutions 114a, 114b are provided. The forced redirection of the air/sound flow provides surfaces against which wax, moisture and/or other impurity/debris may accumulate, so that it is trapped in the convoluted pathway and prevented from advancing toward the receiver 18. Thus the convoluted pathway 114 may function as a reservoir where wax may build up and be retained, thereby preventing its advance toward the receiver 18. Additionally, a reservoir 120 may be provided between the convoluted pathway 114 and the second filter 130. If wax somehow is able to travel through the convoluted pathway, the large dimensions of the reservoir 120 ensure that no capillary action is imposed on any furtherance of wax travel and the wax simply accumulates in the reservoir as it collects at the base of the reservoir 120 under the force of gravity and/or insertion/extraction pressure.

Thus, first filter 110 at the distal end of the base 104 and second filter 130 at the proximal end of the base 104 may be interconnected in fluid communication with each other by convoluted pathway 114 and reservoir 120. The reservoir 120 is much greater in cross-sectional dimension than in the convoluted pathway 114. For example, an inside diameter of the convoluted pathway may be in the ranges described above for openings 112 and may be, but is not necessarily, equal to the diameter/inside dimension of opening 112. Reservoir 120 is made as big as possible while still maintaining the outside diameter of the base 104 small enough to allow sufficient space for the outwardly extending members 106 to function properly and comfortably between the base 104 and the walls of the ear canal. For example, the diameter/largest cross sectional dimension of the reservoir may be in a range from 0.75 mm to 1.3 mm, or from 0.85 mm to 1.2 mm or from 0.95 mm to 1.1 mm. In one specific embodiment, largest cross sectional dimension of reservoir 120 was 1.0 mm. Thus, the largest cross-sectional dimension of reservoir 120 is at least twice as large as the largest cross-sectional dimension of the pathway 114 that it is in fluid communication with, or at least three times, four times, five times, up to twenty-six times larger. In one specific, non-limiting example, the largest cross-sectional dimension of reservoir 120 is 1.0 mm and the largest cross-sectional dimension of the pathway 114 is 0.20 mm. Optionally, opposing angular surfaces 114c, 114d (see FIG. 4C) may be provided along the convoluted pathway to further discourage capillary action on the wax. As can be seen, the features/plates 114c, 114d are on adjacent, but different planes, so that the aperture 112 is not formed by a tubular or other enclosed structure on any one plane parallel to or coplanar with the planes of the plates 114c, 114d. This greatly decreases, if not eliminates capillary action on any wax or liquid in the vicinity of aperture 112 that would otherwise occur if aperture 112 were formed as a tubular structure, such as by laser drilling through a plate or other manner of making a tubular aperture. Aperture 112 has perimeter walls formed by plate 114c on one side of the aperture 112, with opposite perimeter walls formed by plate 114d on the opposite side of the aperture 112 and in a different plane, since plate 114c is in a different plane from plate 114d.

Additionally, the cross-sectional dimensions of openings 114c and 114d are much greater than the cross-sectional dimensions of the aperture 112. In one non-limiting example, the aperture 112 had a cross-sectional dimension (diameter, in this instance) of 0.20 mm, and 114c, 114d had a depth of 0.2039 mm to 0.2450 mm, with the angulation between 112 and 114c,d being ninety degrees. However, the present invention is of course not limited to this specific example as the dimensions may vary. For example, the cross-sectional dimension of 112 need not be a diameter as 112 could be non-circular. The cross-sectional dimension may be in a range from 0.05 mm to 0.5 mm, or from 0.05 mm to 0.10 mm, 0.1 mm to 0.25 mm, 0.15 mm to 0.45 mm, 0.15 mm to 0.3 mm, or any value therebetween. The depths of 114c, 114d may vary between 0.15 mm to 0.5 mm, 0.2 mm to 0.4 mm, or any values therebetween. The angulation between 112 and 114c,d is typically about 90 degrees, but may be in a range from 60 degrees to 120 degrees, 70 degrees to 110 degrees, 80 degrees to 100 degrees. This results in the walls of the openings 114c and 114d being much greater in surface area that is exposed to wax, so that no capillary action occurs relative to the large openings 114c, 114d. Also, the opening perimeters of openings 114c, 114d provide large surface edges that may interact with the wax preferably and with greater attraction than any that may occur with the underlying perimeters of openings 112, further preventing migration of wax through apertures 112. The smallest cross-sectional dimension of openings 114c, 114d may be at least twice as great as the largest cross-sectional dimension of aperture 112, or at least three times as great, or at least four times as great or in a range of 1.5 to 12 times as great, preferably in a range from about 3 to 10 times as great, more preferably in a range from about 4 to about 8 times as great. In at least one embodiment, apertures 112 are rectangular, each having a length of about 0.120 mm and a width of about 0.060±0.025 mm and openings 114c, 114d are rectangular, each having a length of about 0.41 mm and a width of about 0.28 mm. The thickness of each plate may be in a range from about 0.1 mm to about 1 mm, typically from about 0.2 mm to about 0.5 mm. In one example, the thickness was about 0.25 mm. The cross-sectional area of aperture 112 may be less than 25 percent of the cross-sectional area of opening 114c or 114d, preferably less than 15 percent, and may be in a range from about 15 percent to about 2 percent, typically from about 10 percent to about 3 percent. In one example the cross-sectional area of aperture 112 was about 6.27 percent of the cross-sectional area of opening 114c and about 6.27 percent of the cross-sectional area of opening 124d. In another example, the cross-sectional area of aperture 112 was about 3.66 percent of the cross-sectional area of opening 114c and about 3.66 percent of the cross-sectional area of opening 114d.

The second filter 130 may be formed of a mesh having openings therein with dimensions that may be the same as or similar to those described above with regard to filter 20 and which may be constructed in the same manner. The cross sectional area of the second filter is much greater than a cross-sectional area circumscribing the openings 112 of the first filter 110, and preferably is similar or equal to the cross-sectional area of the reservoir space 120. The first filter 110 and/or second filter 130 may alternatively be provided with any other filter design, including, but not limited to: laser-drilled holes, microporous filters, gauze or overlying plates forming a waffle structure as described in U.S. Provisional Patent Application No. 62/573,254, filed Oct. 17, 2017, which is hereby incorporated herein, in its entirety, by reference thereto. FIG. 4C illustrates the placement of second filter 130 at or adjacent to the distal end of the mating connector 102. The length (distance) between the first filter 110 and the second filter 130 is maximized, given other practical constraints that limit the length of the device on which it is to be used. The longer the length is, the more opportunity the inter-filter space provides for wax trapping, where wax falls out, accumulates and/or is trapped to prevent it from reaching the second filter. The longer the length, the more volume that is provided for these functions as well, so that more wax can potentially be trapped prior to the necessity of replacing (or cleaning or other servicing) of the guard, thereby increasing the time intervals between changing wax guards. Since the ear gets more sensitive as it receives objects further and further inwardly, and since the eardrum also prevents infinitely extending the length, there is a range that provides the optimum distances between the filters 110 and 130, typically in the range of from 0.3 mm to 10 mm, or 1.0 mm to 8 mm, or 1.5 mm to 7 mm, or 2.0 mm to 6 mm or 3 mm to 5 mm. In one particular embodiment, the length was 3.89 mm.

Figure 5:
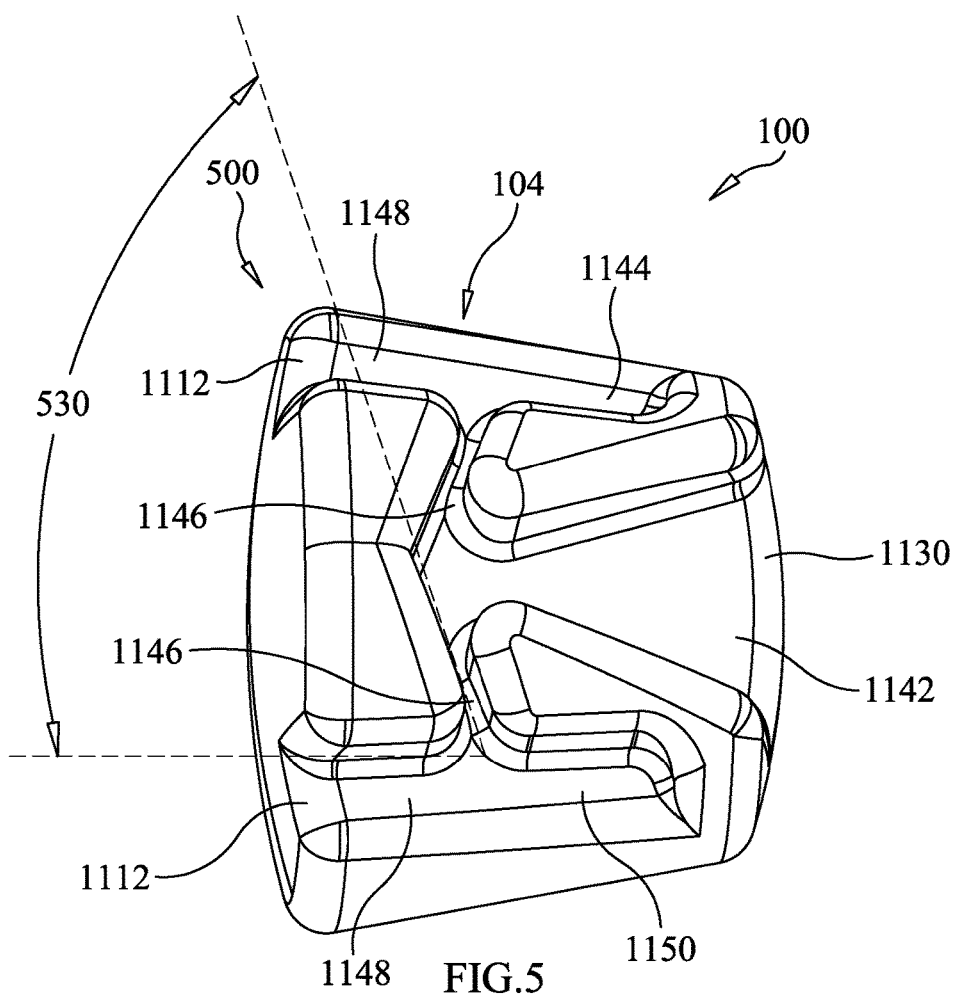
FIG. 5 is a longitudinal, partial view of a guard according to an embodiment of the present invention.

FIG. 5 is a longitudinal view of a guard 100 (not showing outwardly projecting members 106, mating connector 102 or first or second filters 110 or 130 to focus on and better show the convolution features) according to another embodiment of the present invention. The base 104 includes sound exit ports 1112 which may optionally contain first filters 110 (not shown) and opening 1130 which may optionally contain second filter 130 (not shown). There are no straight through openings or pathways connecting 1112 and 1130 through the bae 104. Rather, the sound travels through a convoluted pathways 114. The convoluted pathways have the largest cross-sectional area 1142 at the location of the sound entrance port/opening 1130 (only one shown in FIG. 5, but another port 1130 is on the back side, not visible in FIG. 5) and funnels down to a smaller cross sectional area 1144 at a junction with cross paths 1146. Cross paths 1146 join with exit paths 1148 at the opposite ends thereof. Exit paths 1148 end at sound exit ports 1112 that open to the distal end of guard 100 where they output sound to the tympanic membrane, for example. Exit paths 1148 are larger in cross-sectional area than the cross-sectional areas of cross paths 1146, but are typically smaller in cross-sectional area than the cross-sectional area of sound inlet port 1142. The exit paths 1148 may extend substantially in a longitudinal direction from distal end towards the proximal end of the guard 100. The exit paths 1148 extend past and proximal to their junctions with the cross paths 1146 to form wax repositories 1150 as extensions of the exit paths 1148. The cross-sectional dimensions and areas of the wax repositories 1150 can be essentially the same as the cross-sectional dimensions and areas of the exit paths 1148, as they can essentially be extensions of the same pathways, that extend proximally past the cross paths 1146. Because the wax repositories 1150 having significantly larger cross-sectional areas than the cross-sectional areas of the cross paths 1146, and because the wax repositories 1150 are reached simply by straight through travel of the wax from the sound exit ports 1112 and the exit paths 1148 to the wax repositories 1150, wax flow is encouraged into the wax repositories 1150 and away from the junctions of the sound exit paths 1148 with cross paths 1146. The cross-sectional area of cross path 1146 is less than the cross-sectional area of exit path 1148/wax repository 1150, as noted, typically less than 90% of the cross-sectional area of 1148, 1150, or less than 80% or less than 75% or less than 67%, or less than 60%, or less than 50% or less than 40% or less than 30% or less than 25%.

Additionally, the cross path 1146 may join the sound exit path 1148 at an acute angle 530 as shown in FIG. 5, such that the trajectory of cross path 1146 in a direction from the sound exit path 1148 toward the junction 1144 is in a retrograde trajectory, (a proximal to distal direction), as shown. Because of this arrangement, the direction in which the wax must travel to enter the cross path 1146 has to have a reverse vector component along the longitudinal direction i.e., the wax, if considered to be travelling in a distal to proximal direction in its travel from opening 112 toward the wax repository 1150, must travel in a reverse direction (having a proximal to distal direction) to travel along cross path 1146. This additionally prevents wax from entering cross path 1146 as the wax flow will tend to travel along the past of least resistance.

Figure 6B:
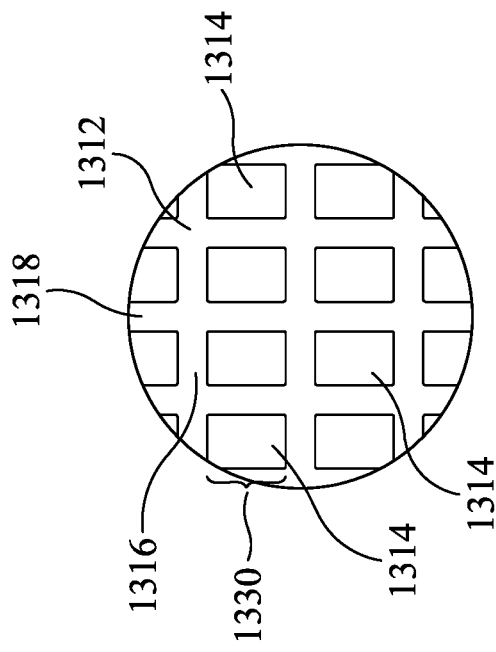
FIGS. 6B and 6C show the distal-more (outer) plate and the proximal-more (inner) plate, respectively, of the filter shown in FIG. 6A.
Figure 6C:
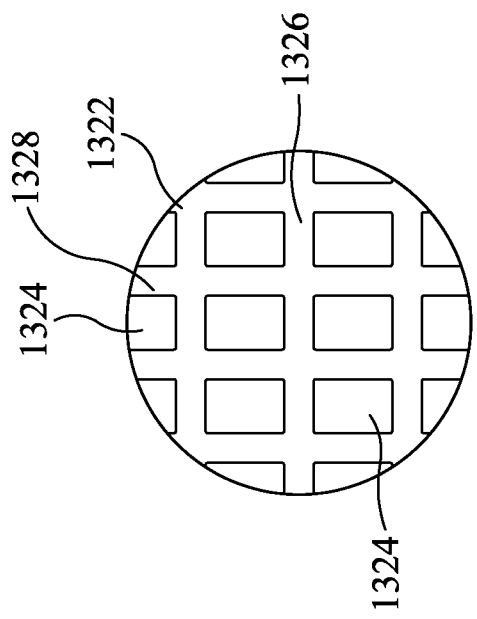
Figure 6A:
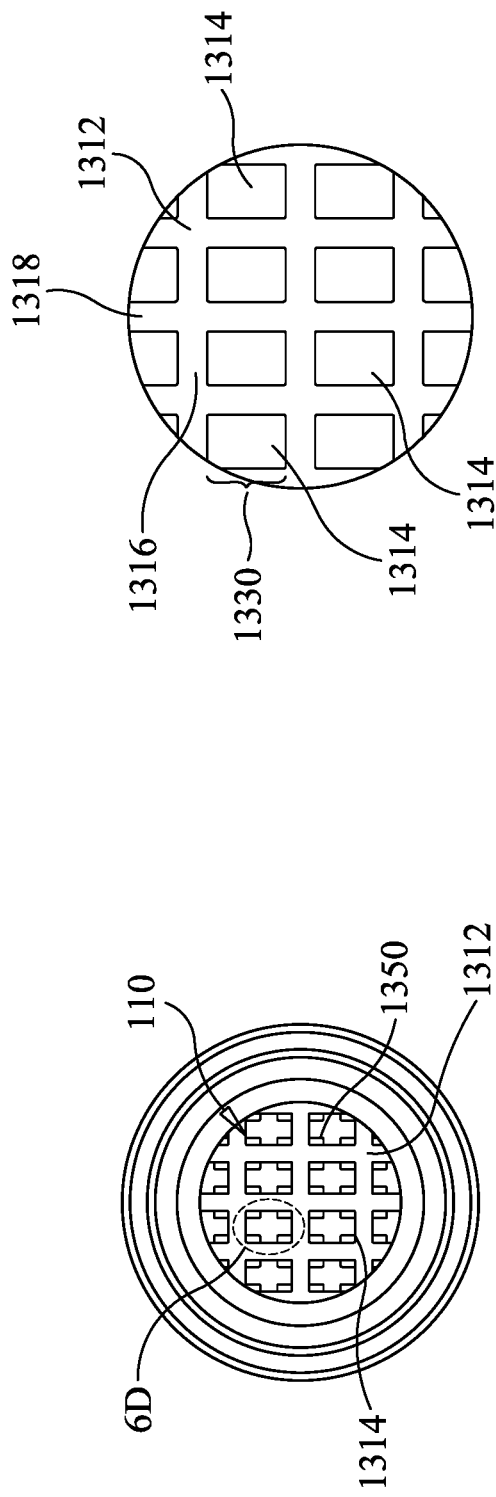
FIG. 6A is a distal end view of a filter that may be employed according to an embodiment of the present invention.

FIG. 6A is a distal end view of a filter 110 that may be employed in an embodiment of the present invention. It is further noted that this type of filter could alternatively or additionally be employed as filter 130 in one or more embodiments of the present invention. Filter 110 is a waffle design filter portion made up of a pair of plates 1312, 1322 both having a plurality of openings 1314, 1324, respectively, therethrough. FIGS. 6B and 6C show the distal-more (outer) plate 1312 and the proximal-more (inner) plate 1314, respectively. Only the outer plate 1312 is shown in FIG. 6A, as it overlies the inner plate 1314 when assembled. The only portions of plate 1322 that are visible in FIG. 6A are the cross-shaped structures that appear in the centers of the openings 1314. As shown in FIGS. 6B and 6C, the openings 1314, 1324 are rectangular in shape, but other embodiments may have openings 1314, 1324 of other shapes, including, but not limited to, square, triangular, circular, oval, elliptical, other polygonal, or irregular. Currently, rectangular and square shaped embodiments are preferred.

Figure 6D:
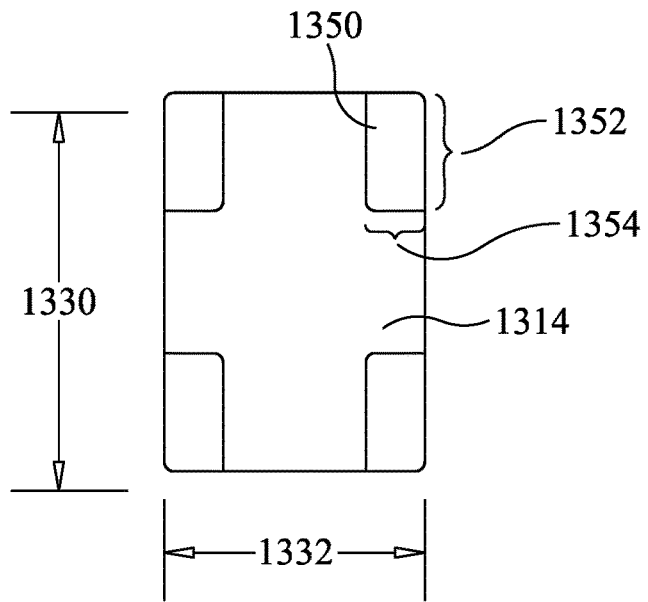
FIG. 6D is an enlarged view of the portion of FIG. 6A within oval 6D shown in FIG. 6A.

The openings 1314 in plate 1312 are arranged in a regular pattern of rows and columns separated by row spacings of equal heights 1316 and column spacings of equal widths 1318. The openings 1324 in plate 1322 can be of the same size, shape and orientation as those of openings 1314 in plate 1312 and can be separated by row spacings 1326 of equal height which are equal to the heights of row spacings 1316 and by column spacings 1328 of equal width equal to the column spacing widths 1318. However, the positions of openings 1324 on plate 1322 in the X and Y directions (width and height directions), respectively, are offset relative to the positions of the openings 1314 on plate 1312 in the X and Y directions, by a distance in the Y (height) direction equal to the height 1330 of opening 1314 minus the height 1352 of aperture 1350 (see FIG. 6D), and by a distance in the X (width) direction equal to the width 1332 of opening 1314 minus the width 1354 of aperture 1350. By offsetting the openings 1324 relative to the openings 1314 as described, upon overlaying plate 1312 on plate 1322, this results in the configuration shown in FIG. 6A, wherein only small apertures 1350 pass through the assembled filter 110 (comprising plates 1312 and 1322 stacked together in contact). In alternative embodiments, the rows and/or columns of openings do not need to be regularly spaced, or even the same size and/or shape from one plate to the other, as long as the overlaying of the plates 1312, 1314 results in apertures as described. The shapes and/or sizes of the openings 1324 in plate 1322 can be different from the openings 1314 in plate 1312 and still produce the apertures 1350 as described, upon overlaying the plate 1312 on plate 1322.

Figure 6E:
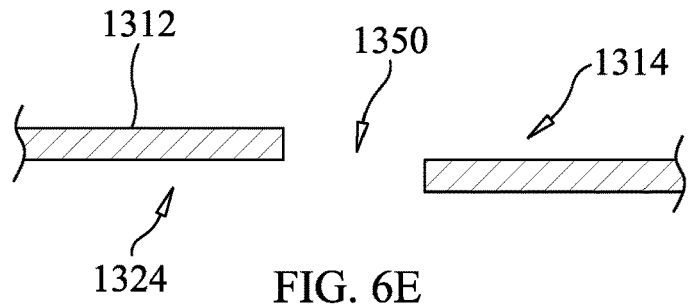
FIG. 6E is a cross-sectional illustration of portions of plates of FIGS. 6A-6D for the purpose of illustrating formation of an aperture by the same.

FIG. 6E. is a cross-sectional illustration of portions of plates 1312 and 1314 for the purpose of illustrating formation of an aperture 1350 by the same. As can be seen, the plates 1312, 1314 are on adjacent, but different planes, so that the aperture 1350 is not formed by a tubular or other enclosed structure on any one plane parallel to or coplanar with the planes of the plates 1312, 1314. This greatly decreases, if not eliminates capillary action on any wax or liquid in the vicinity of aperture 1350 that would otherwise occur if aperture 1350 were formed as a tubular structure, such as by laser drilling through a plate or other manner of making a tubular aperture. Aperture 1350 has two perimeter walls formed by plate 1312 on one side of the aperture 1350, with two opposite perimeter walls formed by plates 1314 on the opposite side of the aperture 1350 and in a different plane, since plate 1314 is in a different plane from plate 1312.

Additionally, the cross-sectional dimensions of openings 1314 and 1324 are much greater than the cross-sectional dimensions of the apertures 1350. This results in the walls of the openings 1314 and 1324 being much greater in length and width than the lengths and widths of the apertures, which provides a much greater amount of surface area that is exposed to wax, so that no capillary action occurs relative to the large openings 1312, 1322. Also, the opening perimeters of openings 1312 provide large lengths and widths of surface edges that may interact with the wax preferably and with greater attraction than any that may occur with the underlying perimeters of openings 1322, further preventing migration of wax through apertures 1350. The smallest cross-sectional dimension of opening 1314, 1324 may be at least twice as great as the largest cross-sectional dimension of aperture 1350, or at least three times as great, or at least four times as great or in a range of 1.5 to 12 times as great, preferably in a range from about 3 to 10 times as great, more preferably in a range from about 4 to about 8 times as great. In at least one embodiment, apertures 1350 are rectangular, each having a length of about 0.120 mm and a width of about 0.060±0.025 mm and openings 1312, 1322 are rectangular, each having a length of about 0.41 mm and a width of about 0.28 mm. The thickness of each plate may be in a range from about 0.1 mm to about 1 mm, typically from about 0.2 mm to about 0.5 mm. In one example, the thickness was about 0.25 mm. The cross-sectional area of aperture 1350 is less than 25 percent of the cross-sectional area of opening 1314 or 1324, preferably less than 15 percent, and may be in a range from about 15 percent to about 2 percent, typically from about 10 percent to about 3 percent. In one example the cross-sectional area of aperture 1350 was about 6.27 percent of the cross-sectional area of opening 1314 and about 6.27 percent of the cross-sectional area of opening 1324. In another example, the cross-sectional area of aperture 1350 was about 3.66 percent of the cross-sectional area of opening 1314 and about 3.66 percent of the cross-sectional area of opening 1324. In the embodiments shown, the apertures 1350 are formed in the four corners of the openings 1314, 1324, and portions of the plates 1312, 1314 obstruct the remainders of the openings, as the plate 1312 is overlaid on plate 1324 and the plates are contacted together as described. The distance between apertures 1350 is typically at least two to three times the greatest cross-sectional dimension of the aperture 1350, and may be in a range of 1.25 to about 6 times the greatest cross-sectional dimension, typically in a range of from about 1.75 to about 4 times the greatest cross-sectional dimension.

Figure 7:
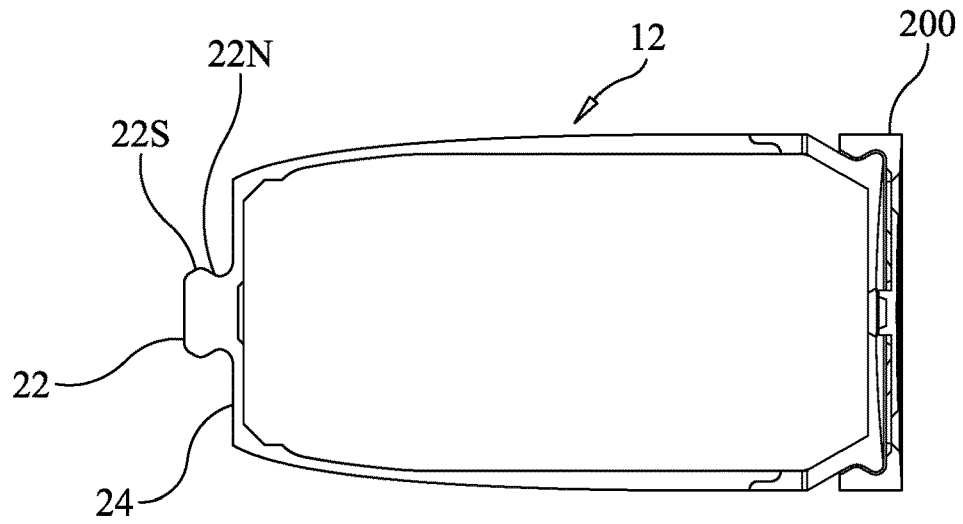
FIG. 7 is a side view of the housing/shell of the device of FIG. 1 with a proximal guard installed thereon and showing a distal tip extending distally from the distal surface of the housing/shell.

FIG. 7 is a side view of the housing 12 with the guard 200 installed thereon and showing the distal tip 22 extending distally from the distal surface 24 of the housing/shell 12. The distal tip 22 may be formed as any shape that may be matingly attached to a mating connector of the guard 100 in a manner that does not require any tools. Therefore distal tip 22 may be any type of projection that can be engaged and matted with a mating connector having features that mate with the distal tip 22. Further alternatively, the distal tip 22 may extend into the distal end portion of the shell 12 in cases where the mating connector of the guard 100 is a projection. In the embodiment shown in FIG. 7, distal tip 22 comprises a nipple that extends from the surface 24 of the distal end of the shell 12. The nipple 22 includes a shoulder or enlarged portion 22S and a necked region 22N in between the enlarged portion 22S and the distal surface 24. Preferably, the shoulder 22S extends circumferentially, 360 degrees about the distal tip, but it need not. For example, the shoulder 24 could be intermittently formed in sections circumferentially about the distal tip. Preferably both the shoulder 22S and necked region 22N are rounded, as shown in the view of FIG. 7, so that the features of the mating connector of the guard 100 can slide smoothly thereover and form a snap fit therewith. In the embodiment of FIG. 7, the distal tip 22 as well as the shell are metal, such as stainless steel, aluminum, titanium, alloys thereof, or the like. However, they could alternatively be made of rigid plastic, such as a thermosetting polymer or other plastic that is more rigid than the plastic from which the mating connector 102 of the guard 100 is made. In one particular embodiment, shell 12 and nipple 22 were made of 316L stainless steel. In other particular embodiments, shell 12 and nipple 22 were made of PA-11 Nylon or PA-12 Nylon or a polycarbonate/PET blend (PC/PET) or a polycarbonate/polybutylene terephthalate (PC/PBT) blend.

Figure 8:
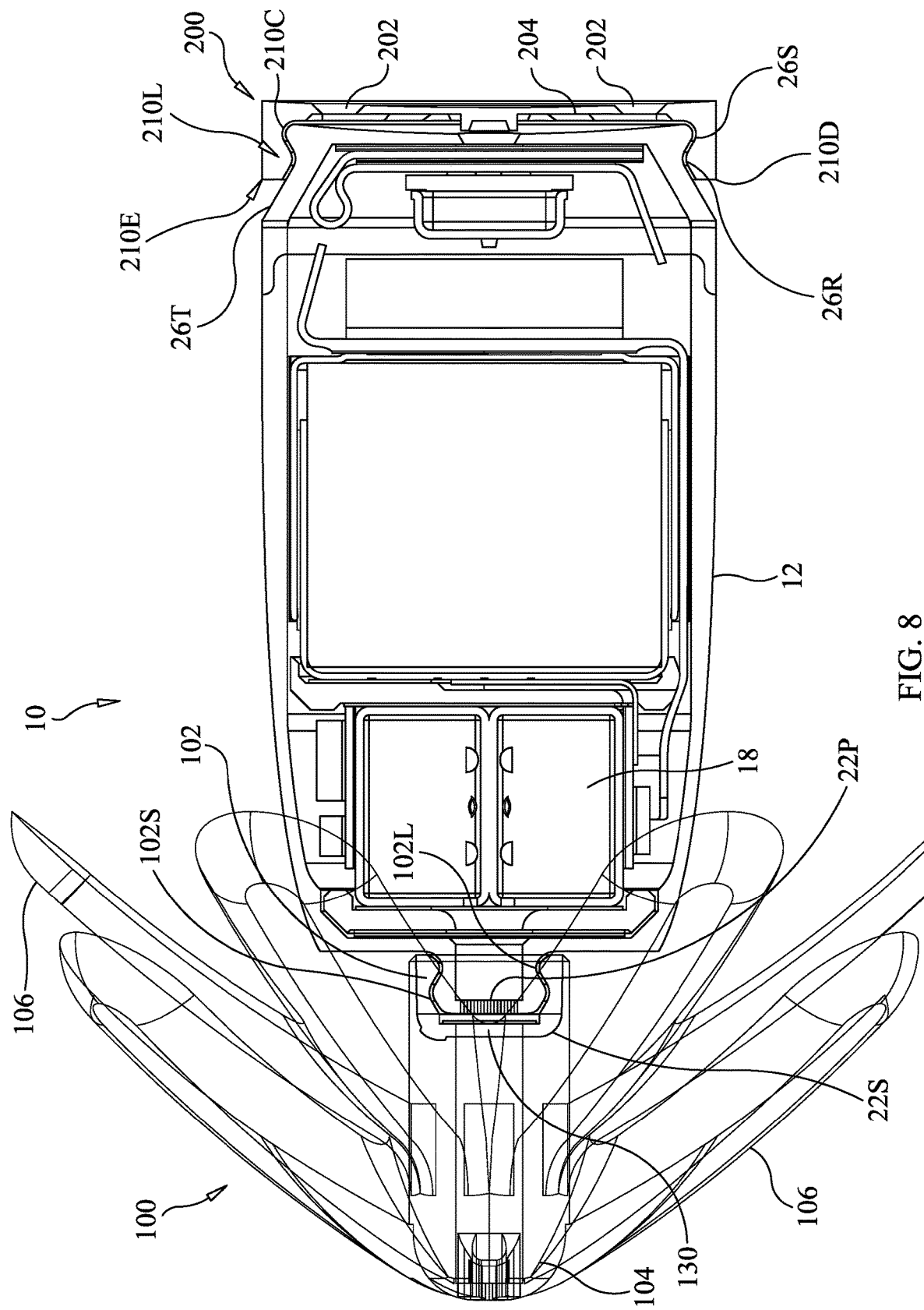
FIG. 8 is a longitudinal sectional view of the device of FIG. 1.

FIG. 8 is a longitudinal sectional view of the device 10 of FIG. 1 which better shows the details of the mating connector 102 of the guard 100 mated with the distal tip 22 of the shell 12 according to an embodiment of the present invention. Mating connector 102 comprises a proximal opening defined by inwardly extending lip 102L, which opens distally to a socket or channel 102S configured and dimensioned to receive and mate with the distal tip 22. As noted above, the material from which mating connector 102 is made is less rigid than the material from which the distal tip 22 is made. For example, the mating connector can be made from PA-11 Nylon or any other type of plastic that will function as described, preferably plastics that chemically bond with silicone. Nylons and polycarbonates are currently preferred materials. The lip 102L has an inside diameter that is less than an outside diameter of the shoulder 22S and is preferably only slightly less than or equal to the outside diameter of the necked region 22N. The largest inside diameter of the socket or channel 102S is slightly less than or equal to the outside diameter of the shoulder 22S and has a curvature that conforms thereto. Likewise, the curvature of the lip 102L (convex, in the embodiment of FIG. 8) conforms to the curvature of the necked region 22N. Like shoulder 22S, the lip 102L need not be continuous around the entire perimeter, but could be intermittently provided in sections. Alternatively, both distal tip 22 and mating connector 102 may be made from the same plastic and mating connector 102 is configured so that it is easier to deform than the distal tip 22.

Attachment of the guard 100 to the shell 12 can be performed by holding the shell 12 in one hand and using the other hand to align the mating connector 102 with the distal tip 22. The guard 100 can then be pressed against the shell 12, such as by pushing against the outwardly extending members 106 and/or tab 300 and/or base 104, while applying counterforce through the shell 12 with sufficient force to cause the mating connector 102 to mate with the distal tip 22. Alternatively, the outwardly extending members 106 and/or tab 300 and/or base 104 can be pulled toward the shell 12 while applying counterforce through the shell 12. In either case, sufficient force can be readily applied by hand to cause the lip 102L to elastically deform and expand as it rides over the shoulder 22S. As the lip 102L passes the shoulder 22S, it then resiliently contracts against the neck region 22N forming a snap fit therewith, as the shoulder 22S also simultaneously mates with the socket or channel 102S. This snap fit may cause an audible snapping sound to provide positive feedback to the user that the connection has been successfully accomplished. Further, additionally or alternatively, haptic feedback may be provided to the fingers of the user through the outwardly extending members 106 or other portion of the guard and/or through the shell as the snap occurs, so that the user can actually feel the snap connection being made. Although a snap connection is currently the preferred type of mating connection to be performed by joining the mating connector 102 and distal tip 22, alternative types of connections could be performed, each without the need to resort to any types of tools. Such alternative types of connections include, but are not limited to: press fit, bayonet fit, screw thread, ball and detent, or other equivalent mechanical fitting that does not require tools. Mating connector 102 is formed of a more rigid material than that of the base 104 and outwardly extending members 106 of the guard, which are softer and more flexible. The additional rigidity is needed to establish the positive snap fit with the distal tip.

The distal tip includes one or more openings 22P passing therethrough to allow sound and air to travel from the receiver 18 therethrough and out through the guard 100 to deliver sound to the eardrum of the user. When assembled as shown, the distal end of the distal tip abuts or is positioned closely adjacent the filter 130 of the guard 100.

Not only can the guard 100 be connected to the shell 12 without the need to use any tools, as described, the guard 100 can also be removed from the shell 12 without the need to use any tools. This, like the attachment process, can be performed by the user, since it does not require a high level of training or dexterity and does not require the use of any tools. To remove the guard, the user grasps the shell 12 in one hand and grasps the pull tab 300 and/or one or more outwardly extending members 106 and/or the base 104 and pulls the guard 100 in one direction while holding the shell 12 stationary or pulling it in the opposite direction. Similarly, the guard could be held stationary while pulling the shell 12 away, but most users find it easier to hold the shell 12 and pull on the guard 100. The largest outside diameter or largest outside cross-sectional dimension of the shell 12 may be a value in a range from about 5.5 mm to about 7.85 mm, typically in a range from 6.5 mm to 7.5 mm. In one specific example, the outside diameter was about 6.8 mm. In another specific example, the outside diameter was 7.0 mm. The largest outside diameter or cross-sectional dimension of shell 12 is typically constrained by a desire to make it as large as possible for containing the battery and other components, as well as facilitating easier handling and manipulation by the user, while at the same time keeping this dimension small enough to fit within a large population of various ear canal sizes with comfort. The largest outside diameter or largest outside cross-sectional dimension of the base 104 of the guard 100 may be in a range from about 1.5 mm to about 3.5 mm, typically from 2.0 mm to 3.0 mm. In one specific example the largest outside diameter of the base 104 was 2.4 mm. When sufficient extension forces are established between the mating connector 102 and the distal tip 22, the lip 102L expands as it rides distally over the shoulder 22S and then breaks contact with the distal tip 22 as the guard 100 is separated from the shell 12 and the lip 22L resiliently returns to its unbiased configuration.

Advantageously, when the base 104 and outwardly extending members 106 are formed of a clear or translucent material such as silicone, for example, this may provide the user the ability to see when wax buildup has occurred in amounts and/or locations which indicate that the device 10 needs to be serviced. This may help the user to change out the guard 100 before wax buildup gets to a level where it starts deteriorating the performance of the hearing device.

Since the guard 100 integrates the outwardly extending members 106 and wax filters 110, 130, the user can easily perform maintenance to the device to eliminate wax buildup and replace the outwardly extending member 106 all in one simple procedure that does not require any tools to perform and is easy and fast to perform.

Figure 10:
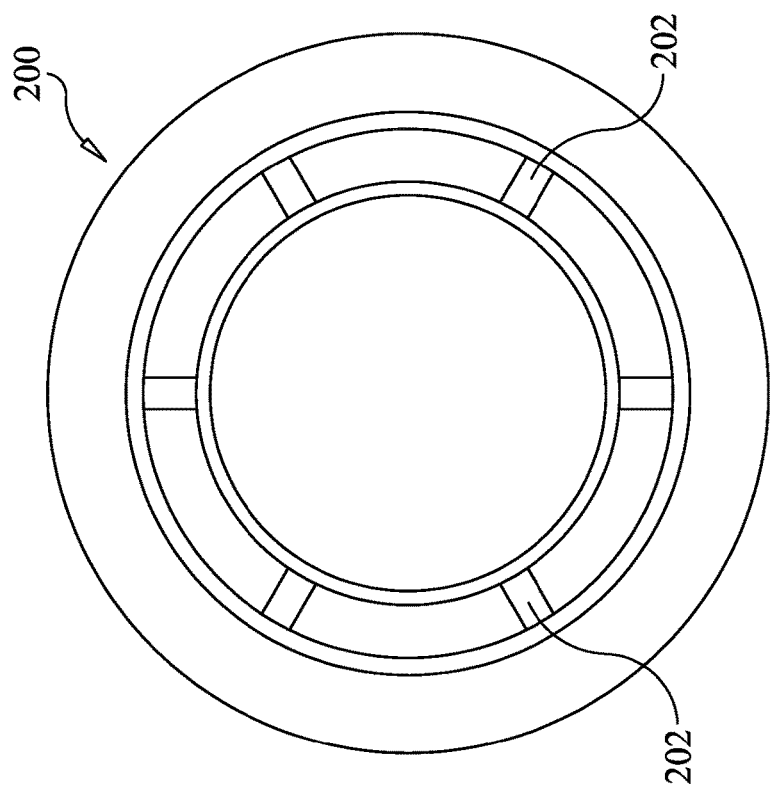
FIG. 10 is a proximal end view of the guard of FIG. 9.
Figure 9:
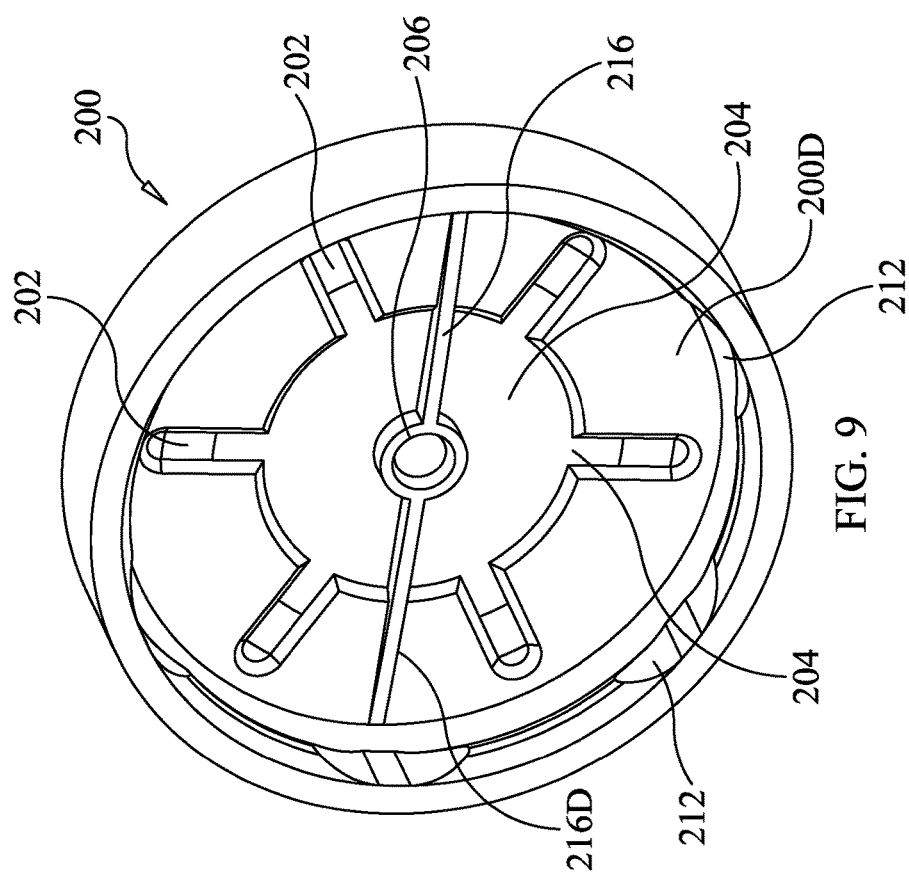
FIG. 9 shows a perspective view of a distal end of the proximal guard of FIG. 1.

FIG. 9 shows a perspective view of a distal end of the guard 200 of FIG. 1. FIG. 10 is a proximal end view of the guard 200 of FIG. 9. The guard 200 has an outside diameter (in embodiments when cross-section of guard is circular, such as the embodiment shown in FIG. 9) or largest outside cross dimension (for embodiments where cross-section is non-circular) in the range from about 5.5 mm to 8 mm, preferably from 6 mm to 7.5 mm, more preferably from about 6.5 mm to about 7.4 mm. In one preferred embodiment, outside diameter is about 6.8 mm. In another preferred embodiment, outside diameter is about 7.0 mm. By making this dimension sufficiently large as described, this facilitates the manipulation of the guard 200 by the user in snapping the guard onto and off from the device 10. Not only is the guard easier to grasp, which is an important feature as many users have impaired dexterity, but the resultant large inside diameter at the distal end portion of the guard 200 makes alignment of the guard 200 with the cap 26 easier, thereby further facilitating snapping the guard 200 onto the cap 26. FIG. 11 is a proximal end view of the cap 26 shown in FIG. 2. Filter 200 is provided with openings 202 that are configured to allow air and sound to pass therethrough. However, it is also possible for wax to pass through openings 202. The end cap 26 that closes the proximal end of the shell 12 when attached thereto, as described above, is provided with a single central opening 280 (in the shape of an oval or lozenge as shown in FIG. 11, but could be other shapes, such as circular, square, rectangular, other polygonal, or irregular) that aligns with the microphone 14, but has a larger perimeter and cross sectional area than that of the microphone 14. When guard 200 is connected to cap 26 as illustrated in FIG. 8, the distal surface 200D contacts or forms a close fit with the proximal surface 26P of cap 26. In cases where a close fit is formed the tolerance between the surfaces is in a range from 0.01 mm to 1.2 mm, typically from 0.02 mm to 1.0 mm, more preferably from 0.03 mm to 0.08 mm or 0.04 mm to 0.07 mm. In one particular embodiment the tolerance was 0.05 mm. Because of the close proximity of the surfaces 26P, 200D, airflow and sound are directed through channels 204 that extend radially inwardly from openings 202 toward central cover 206. Central cover 206 aligns with the microphone 14 and blocks flow directly thereto. Thus, airflow/sound, as well as any wax that may enter through openings 202 must travel a convoluted pathway through opening 204, making a ninety degree or greater (or somewhat less, e.g., in the range of 70 to 110 degrees, or 80 to 100 degrees, or 85 to 95 degrees) turn to travel radially inwardly along pathway 204 toward central cover 206, into a portion of central opening 280 that extends outside the perimeter of microphone 14 and under central cover 206 in order to reach the microphone 14. While this is not an overly restrictive pathway for sound and air to travel, it does provide significant obstacles to wax flow, making it unlikely that wax will reach the microphone 14 before being deposited at turns along the convoluted pathway, including, but not limited to where the wax passes through opening 202 and is diverted to channel 204, as well as channel 204 and, potentially the central opening 208 at locations radially outwardly of central cover 206. The guard 200 will typically be replaced and the proximal surface of the cap 26 cleaned before complete clogging that would prevent sound from reaching the microphone 14, but if the device 10 were neglected and not timely serviced, clogging is likely to occur in one of the bends of a convoluted pathway before clogging of the microphone 14 with wax ever gets a chance to occur.

The proximal end of the cap 26 is configured to mate with the guard 200, so that the guard 200 can be attached thereto and removed therefrom without the need to use any tools and is relatively simple to perform so that these tasks can be accomplished by a user of the device. As illustrated in FIG. 8, the cap 26 tapers between the distal and proximal ends thereof to form a recessed or necked region 26R. A shoulder or enlarged portion 26S extends proximally of the necked region 26R. Preferably, the shoulder 26S extends circumferentially, 360 degrees about the proximal end of the cap 26, but it need not. For example, the shoulder 26S could be intermittently formed in sections circumferentially about the proximal end of the cap 26. Preferably both the shoulder 26S and necked region 26R are rounded, as shown in the view of FIG. 8, so that the features of the mating connector of the guard 200 can slide smoothly thereover and form a snap fit therewith. In the embodiment of FIG. 8, the cap 26 is formed of a rigid plastic such as PA-11 Nylon or PC blend that is more rigid than the plastic from which guard 200 is made. For example, guard 200 could be made of BioPBS plastic (biocompatible polybutylene succinate), silicone, metal, thermoplastic polyurethane or rubber. Alternatively, both cap 26 and guard 200 may be made from the same plastic and guard 200 is configured so that the mating connector of the guard is easier to deform than the shoulder 26S of the cap 26.

FIG. 8 is a longitudinal sectional view of the device 10 of FIG. 1 which better shows the details of the mating connector 210 of the guard 200 mated with the proximal end portion of the cap 26. FIG. 12 is a sectional view of the guard 200 showing details of the mating connector 210. Mating connector 210 comprises a distal opening defined by inwardly extending lip 210L, which opens proximally to a channel 210C configured and dimensioned to receive and mate with the proximal end portion of cap 26. As noted above, the mating connector 210 is more readily deformable than is the shoulder 26S at the proximal end portion of the cap 26. Mating connector 210 and/or the entire guard 200 can be made of a plastic that is less rigid than the plastic from which cap 26 is made, and/or, the mating connector 210 can be provided with weakened sections 212 such as scallops, cutouts or even gaps that break the continuity of the lip 210L, so as to make the lip 210L, and optionally, the channel 210C easier to deform. The lip 210L has an inside diameter that is less than an outside diameter of the shoulder 26S and is preferably only slightly less than or equal to the outside diameter of the necked region 26R. The largest inside diameter of the channel 210C is slightly less than or equal to the outside diameter of the shoulder 26S and has a curvature that conforms thereto. Likewise, the curvature of the lip 210L (convex, in the embodiment of FIGS. 8 and 12) conforms to the curvature of the necked region 26R. Like shoulder 26S, the lip 210L need not be continuous around the entire perimeter, but could be intermittently provided in sections and/or separated by weakened sections 212.

The distal end portion of the cap 26 tapers into the necked region 26R as shown in FIG. 8. The distal surface of the mating connector 210 of the guard 200 is not tapered but is oriented substantially normal to the longitudinal axis of the cap 26, as illustrated in FIG. 8. The interface between the tapered surface 26T and the distal surface 210D of the mating connector 210 forms a notch or gap such that the distal surface 210D has an exposed edge 210E that can be readily engaged by the fingers of the user to apply force thereto so as to disconnect the guard 200 from the cap 26. The height of the edge 210E may be in a range from about 0.1 mm to 2 mm. In one specific example, the height of the edge 210E (measured from the bottom of the notch or gap to the outer side wall of the guard 200) was 0.30 mm. The surface of the notch or gap formed by the edge 210E and/or all or a portion of the outer side wall of the guard 200 may be surface-roughened, such as by knurling or the like to provide more friction when the user's finger(s) is interacting therewith to facilitate removing the guard 200. Edge 210E can alternatively be a raised feature that would likewise facilitate engagement by the fingers of a user.

Attachment of the guard 200 to the cap 26 can be performed by holding the shell 12 in one hand and using the other hand to align the mating connector 210 with the shoulder of the cap 26. The relatively large outside diameter of the guard 200 makes it easily manipulatable by the user, thereby facilitating the alignment and attachment processes, even for users that may have arthritis, shakiness, or other moderate dysfunction of the fingers. The guard 200 can then be pressed against the cap 26, such as by pushing against the proximal end of the guard 200 while applying counterforce through the shell 12 with sufficient force to cause the mating connector 210 to mate with the cap 26 as shown in FIG. 8, wherein the lip 210L is mated in the neck region 26R and the shoulder 26S is mated in the channel 210C. Sufficient force applied causes the lip 210L to elastically deform and expand as it rides over the shoulder 26S. As the lip 210L passes the shoulder 26S, it then resiliently contracts against the neck region 26R forming a snap fit therewith, as the shoulder 26S also simultaneously mates with the channel 210C. This snap fit may cause an audible snapping sound to provide positive feedback to the user that the connection has been successfully accomplished. Further, additionally or alternatively, haptic feedback may be provided to the fingers of the user through the guard 200 and/or through the shell 12/cap 26 as the snap occurs, so that the user can actually feel the snap connection being made. Although a snap connection is currently the preferred type of mating connection to be performed by joining the mating connector 210 and cap 26, alternative types of connections could be performed, each without the need to resort to any types of tools. Such alternative types of connections include, but are not limited to: press fit, bayonet fit, screw thread, ball and detent, or other equivalent mechanical fitting that does not require tools.

Figure 13A:
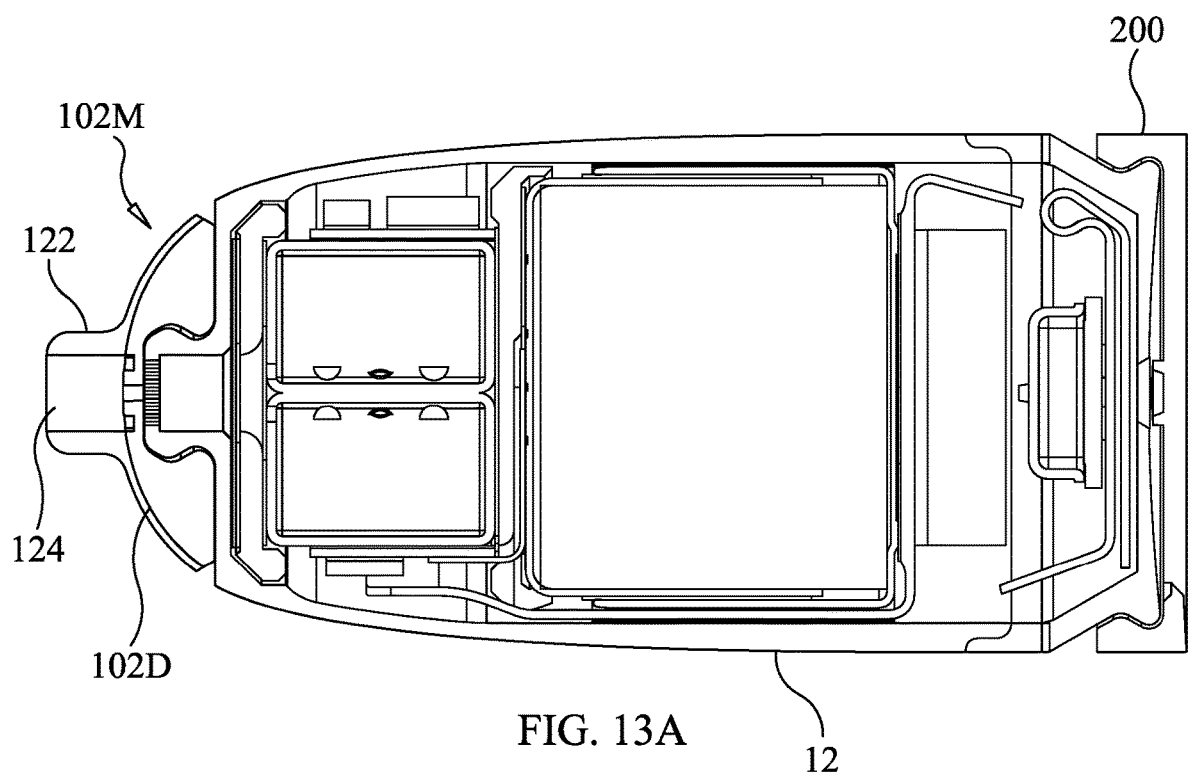
FIG. 13A shows a mating connector releasably connected to a distal tip, according to an embodiment of the present invention.
Figure 13B:
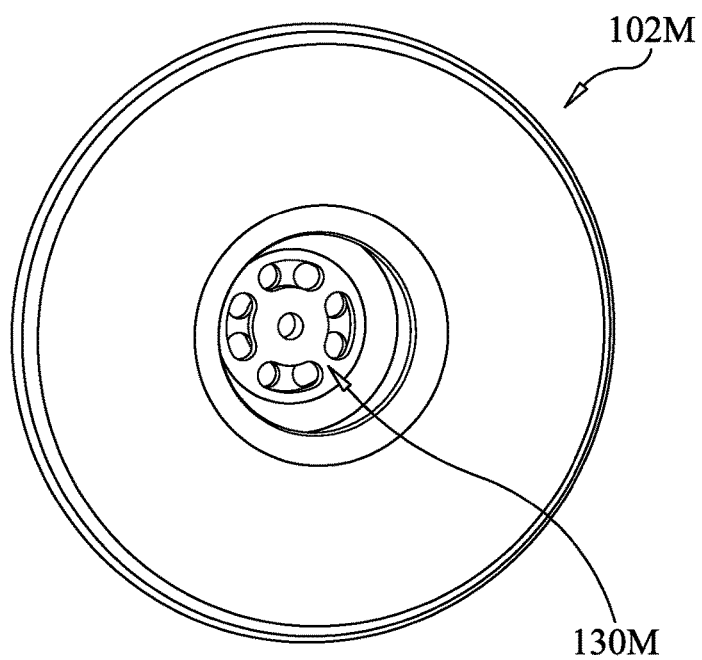
FIG. 13B is a proximal end view of the mating connector of FIG. 13A.

FIGS. 13A-13E are now referred to in describing a modular guard 100 according to an embodiment of the present invention. FIG. 13A shows a mating connector 102M releasably connected to the distal tip 22 (not shown in FIG. 13A) of the shell 12. Although in practice the mating connector 102M will typically not be connected to the shell as a singular component, it is shown this way to demonstrate that the mating connector features may be the same as 102 above and function in the same manner. Mating connector 102M may be made of any of the same materials used to make mating connector, and any particular feature of mating connector 102M not described here may be the same as that of mating connector 102 described above. The filter 130M shown in the proximal end view of mating connector 102M in FIG. 13B comprises a plurality of through holes that allow fluid communication with the openings 22P (see FIG. 8) so as to allow air/sound flow from within the shell (e.g., from the receiver) through the openings 22P and openings of 130M to a location distal of the mating connector 102M. Alternatively, the filter 130M may be a mesh, as described above with regard to filter 130, or any of the other alternative embodiments of wax filters described above with regard to filter 130. Further alternatively, a mesh, such as mesh 130 may be placed within the mating connector 102M, adjacent the openings of filter 130M shown in FIG. 13B so as to be positioned between those openings and the openings 22P when the mating connector 102M is snapped onto the distal tip 22.

A mating tip 122 extends distally of the distal surface 102D of the mating connector 102M. The mating tip 122 has an outside diameter configured and dimensioned to be received within a proximal connector of modular guard component as described below. A channel or annulus 124 extends through mating tip 122 and is in fluid communication with openings of filter 130M such that mating connector 120M is configured to allow airflow/sound axially therethrough.

Figure 13C:
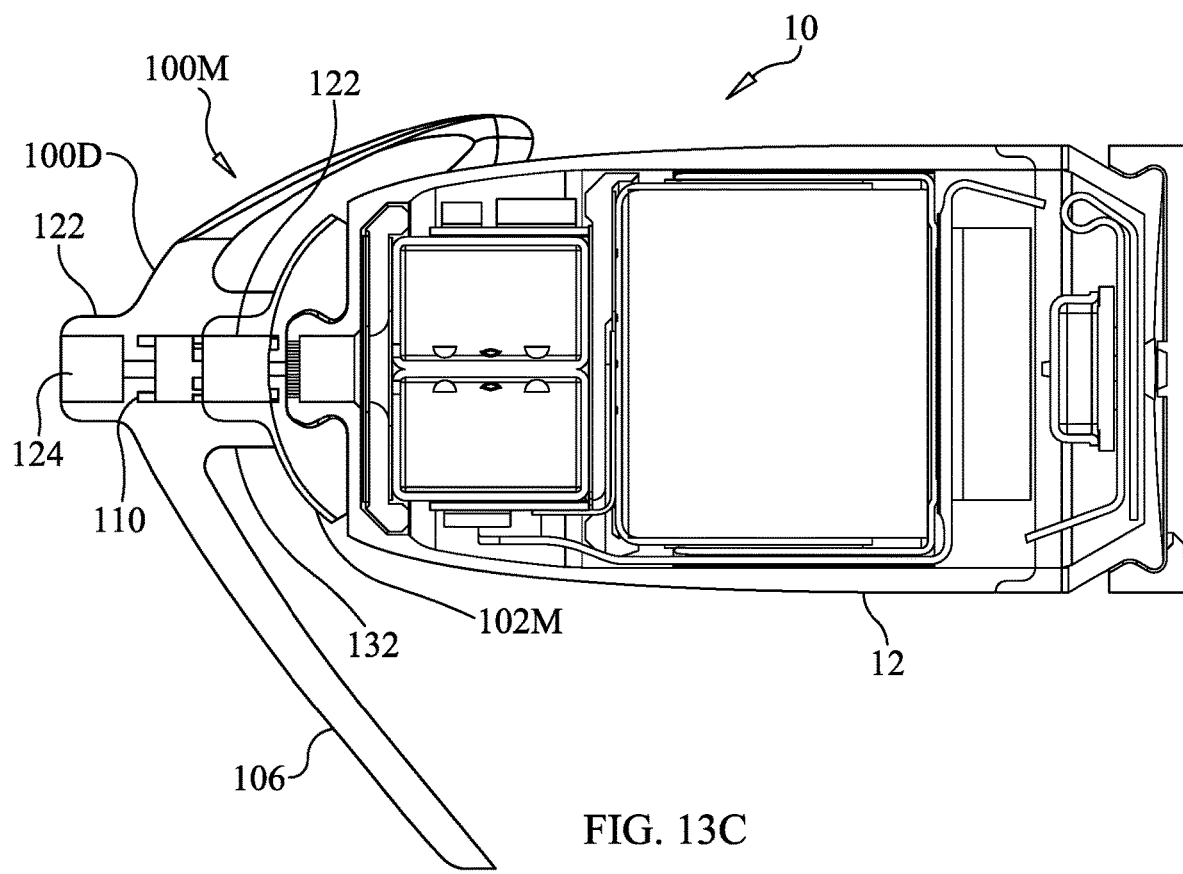
FIG. 13C shows a modular guard component having been joined to the modular mating connector of FIG. 13A.

FIG. 13C illustrates a modular guard component 100M having been joined to the modular mating connector 102M. The main body of the mating connector 102M may be made of the same material used to make mating connector 102, as noted above. The mating tip 122 of the modular mating connector 102M may be made of the same material that the proximal connector 132 of the modular guard component 100M is made. For example, if the proximal connector 132 is made of silicone, then making the mating tip 122 of silicone facilitates joining the mating tip 122 and connector 132 together, such as by adhesive, heat bonding, welding (including, but not limited to laser welding), over molding or the like. Modular guard component 100M includes a base 104M that extends longitudinally from a mating tip 122 that extends distally of a distal surface 100D of the guard component 100M, to the proximal connector 132. Proximal connector 132 is dimensioned and configured to form a close fit with mating tip 122 of modular mating connector 102M. A cavity formed within the proximal connector 132 has a length and diameter substantially equal to the outside diameter and length of mating tip 122 of the modular connector. Alternatively, the cavity diameter may be slightly less than the outside diameter of 122, or slightly greater to provide tolerance for an adhesive. Similarly, the length of the cavity may be slightly greater than the length of the mating tip 122.

Figure 13D:
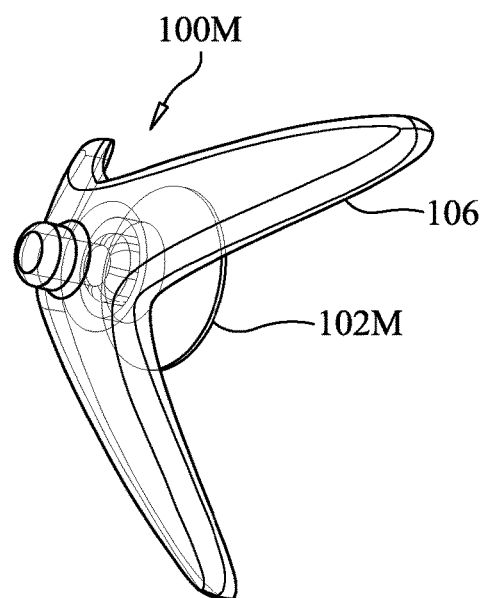
FIG. 13D is a perspective view of a modular guard component joined to a modular mating connector, according to an embodiment of the present invention.

Flexible fibers 106 extend radially outwardly from base 104 as shown in FIGS. 13C-13D. Typically, each modular guard component 100M will have one row of outwardly extending members/flexible fibers 106 as shown, but alternatively, two or more rows of outwardly extending members/flexible fibers could be provided on a single modular guard component 100M. The modular guard components 100M may be made from any of the same materials as the main body and outwardly extending members of guard 100.

Like guard 100, each modular guard component 100M is further provided with a filter 110 located on or adjacent to the distal face of the base 104 as shown in FIG. 13C. A mating tip 122 extends distally of the filter 110 and has a channel 124 in fluid communication with filter such that modular guard component 100M is configured to allow airflow/sound axially therethrough to receive/send airflow/sound between the modular mating connector 102M and the space distal of the distal end of mating tip 122 of the modular guard component 100M. Filter 110 is configured to allow air flow/sound therethrough, while discouraging the inflow of wax and moisture. The dimensions of the pore filters may have a largest cross-sectional dimension in the rage from 0.1 mm to 0.5 mm. In one particular embodiment, the pores were square with dimensions of 0.2 mm×0.2 mm Like guard 100, at least one convoluted pathway 114 and reservoir 120 may be provided to connect the filter 110 and filter 130M once modular guard component 100m is joined with modular mating connector 102M.

Figure 13E:
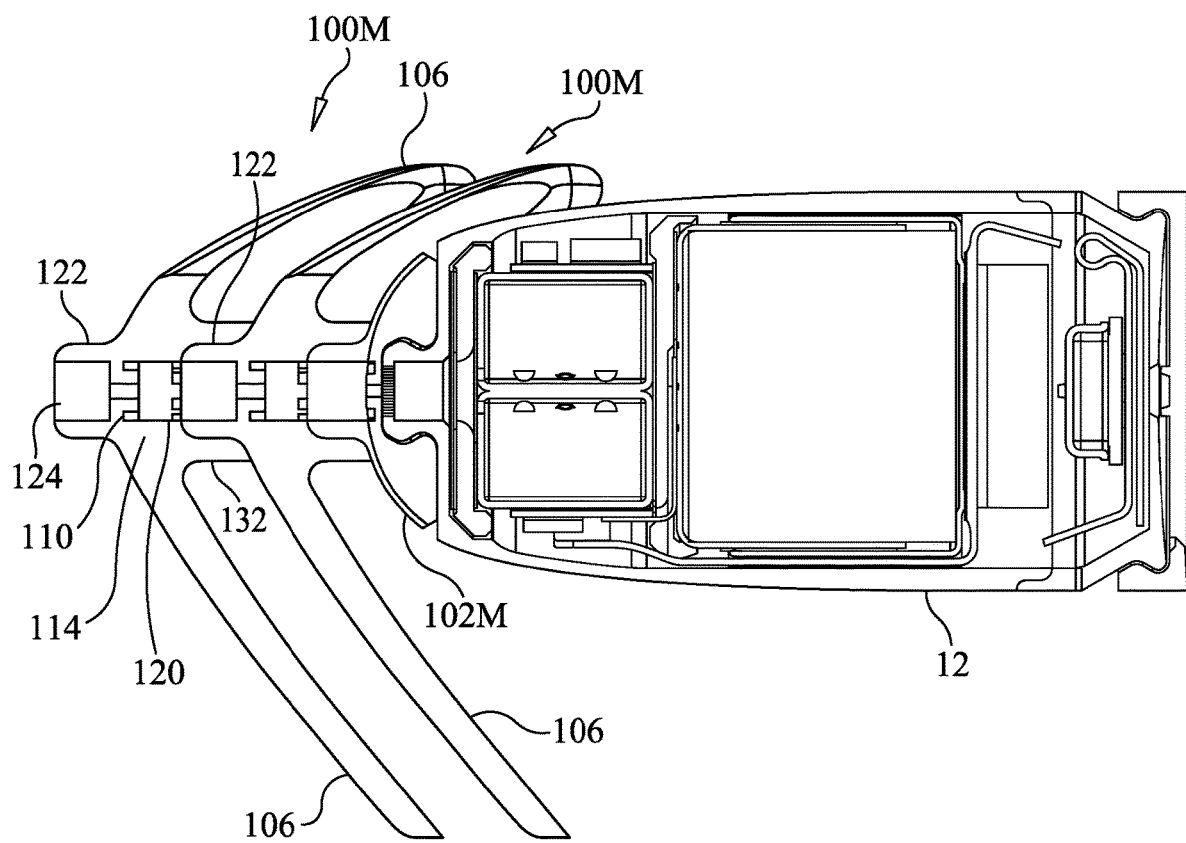
FIG. 13E shows a longitudinal sectional view of the device of FIG. 13C after joining a second modular guard component to the first modular guard component shown in FIG. 13C.

FIG. 13E illustrates a longitudinal sectional view of the device 10 of FIG. 13C after joining another modular guard component 100M to the modular guard component 100M shown in FIG. 13C. In this embodiment, the second modular guard component 100M is identical to the first one shown in FIG. 13C. Alternatively, the second modular component 100M could be different from the first, such as by including two rows of outwardly extending members 106, for example. The second module 100M is mounted to the first module 100M preferably so that the outwardly extending members 106 are offset from the outwardly extending members 106 of the first modular component 100M when viewed in a direction of the longitudinal axis, similar to what is shown in FIG. 1 with regard to the outwardly extending members 106 of guard 100. Alternatively, the members 106 of each row could be aligned in the direction along the longitudinal axis. Because the second module 100M can be joined to the first module 100M in any orientation about the longitudinal axis, it is possible to arrange the first row of outwardly extending members 106 in alignment with, or offset by any amount desired, from the second row of outwardly extending members. Like the first module 100M, the second module 100M also may be provided with a filter 110, at least one convoluted pathway 114 and reservoir 120. In this way, by assembling modules of the guard 100M, the resulting guard can have more than the two filters 110, 130 described with regard to the guard 100 of FIG. 1. For example, in FIG. 13E, there are two filters 110 (one in each of modules 100M) and a filter 130M in the modular mating connector 102M. Further, each filter 110, 110, 130M is separated from its adjacent filter by at least one convoluted pathway 114 and a reservoir 120, providing even greater resistance to wax flow and thereby providing further restrictions to wax flow ever reaching the shell 12. The modules 100M assembled to the snap base part could have various different types of tip styles, depending on the required fit/acoustic performance. For example, modules 100M may differ from one another in terms of filter pore sizes, amount of acoustic occlusion provided, wherein the number, size and or placement of the outwardly extending members 106 may vary, more or less acoustically occlusive seals, or custom-fit designs that may be customized and produces by 3D printing. Because all of the modular components are integrated upon assembly, they form a singular unit that can be attached to and removed from the shell 12 in the same manners as described above with regard to guard 100. This modular technique of building a wax guard allows any number of modules 100M to be assembled to the guard assembly, as long as the resultant construct remains sufficiently acoustically transparent so as to not detract from the acoustic function of the device that it is attached to and is not too long so as to contact the eardrum or otherwise provide unwanted obstruction in the ear canal. Accordingly, more than three filters could be installed in a modular guard of this type if desired and, likewise, more than two sets of convoluted pathways and/or more than two reservoirs could be provided in between the filters in the manner described above.

Figure 14:
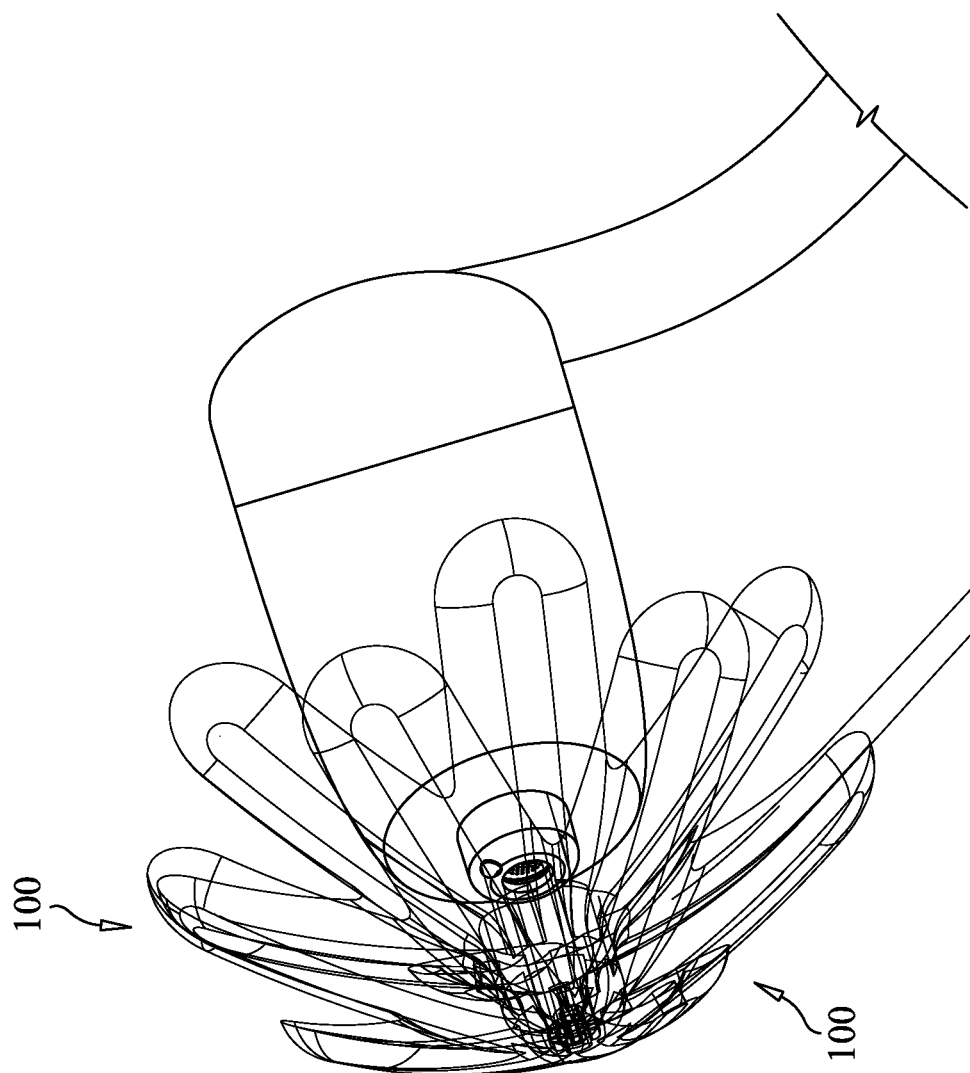
FIG. 14 is a perspective view of a guard attached to an in ear hearing bud, according to an embodiment of the present invention.

FIG. 14 is a perspective view of a guard 100 attached to an in ear hearing bud, according to an embodiment of the present invention.

Figure 15:
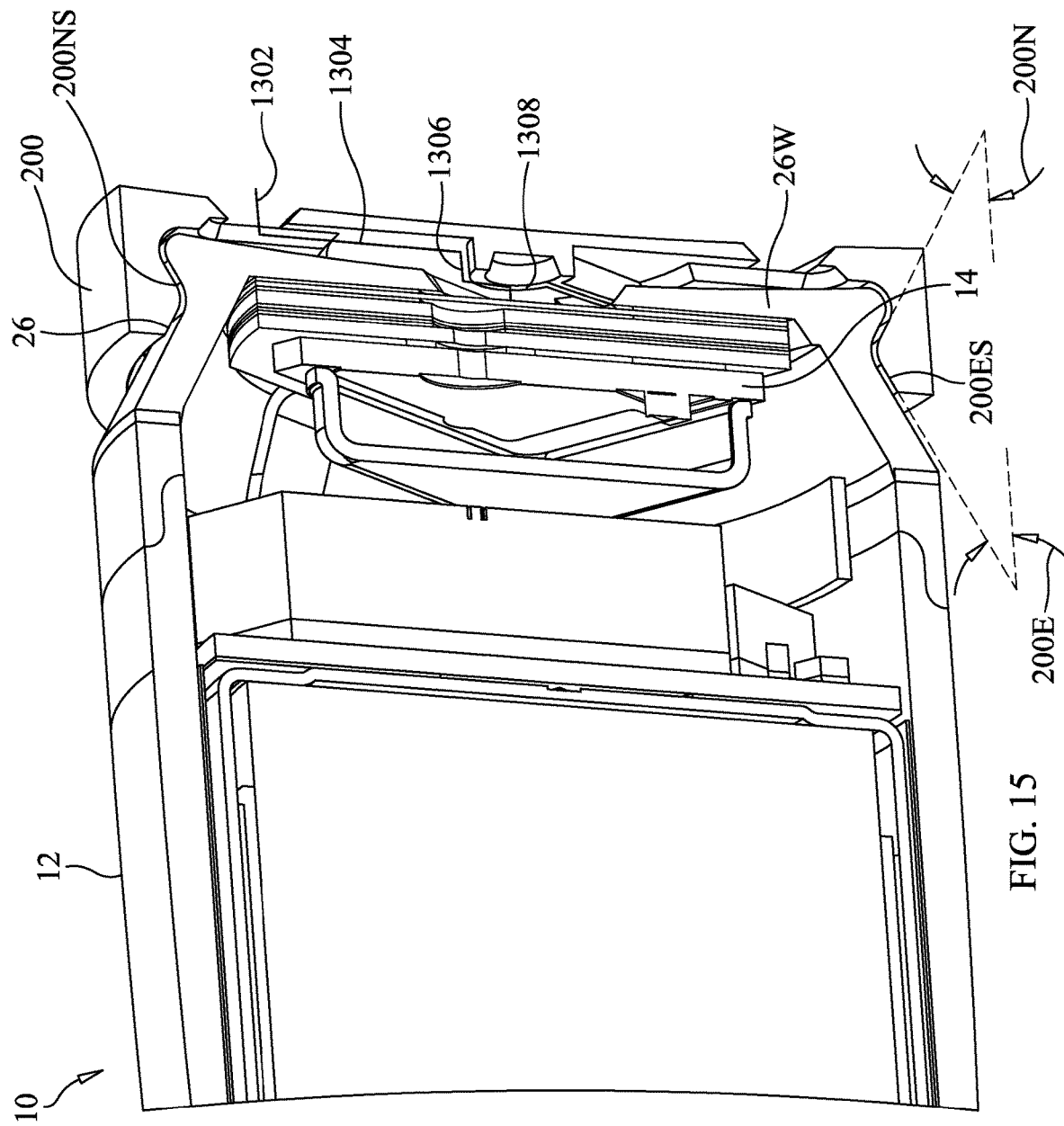
FIG. 15 is a perspective view of a proximal end portion of the device shown in FIG. 8.

FIG. 15 is a perspective view of a proximal end portion of the device 10 shown in FIG. 8. This view illustrates convoluted pathways 214 that sound/air must travel from outside of the device 10 to reach the microphone 14. As described with regard to FIGS. 9-11 above, sound/air and/or wax can enter through openings 202 in a direction 1302 towards cap 26. Upon contacting the cap 26 at location 26W, the sound/air flow is redirected along pathway 1304 through channel 204 that extends radially inwardly from opening 202 toward central cover 206 (see FIGS. 15 and 9). Central cover 206 aligns with the microphone 14 and blocks flow directly thereto. Thus, airflow/sound is again redirected in directions 1306 and 1308 by central cover 206 (outside surface first, then inside surface) to reach the microphone 14. Thus, airflow/sound, as well as any wax that may enter through openings 202 must travel a convoluted pathway through opening 204, making a ninety degree or greater (or slightly less) turn to travel radially inwardly along pathway 204 toward central cover 206, into a portion of central opening 280 that extends outside the perimeter of microphone 14 and under central cover 206 in order to reach the microphone 14. While this is not an overly restrictive pathway for sound and air to travel, it does provide significant obstacles to wax flow, making it unlikely that wax will reach the microphone 14 before being deposited at turns along the convoluted pathway, including, but not limited to where the wax passes through opening 202 and is diverted to channel 204, as well as channel 204 and, potentially the central opening 208 at locations radially outwardly of central cover 206. FIG. 15 also identifies the entry and egress surfaces of the guard 200 that function during attachment to and detachment from the cap 26. The entry angle 200E is the angle of the entry surface relative to the longitudinal axis of the guard 200 and the egress angle 200N is the angle of the egress surface relative to the longitudinal axis of the guard. Angles 200E and 200N are typically within the range from 20 to 55 degrees, more preferably 25 to 50 degrees. In one embodiment, angles 200E and 200N were about 30 degrees. In another embodiment, angles 200E and 200N were about 45 degrees. Although angles 200E and 200N are typically equally, they need not be. During attachment the angled entry surface 200ES contacts the cap 26 and is deformed outwardly so that it can pass over the lip feature 26c and then return to its undeformed state (or nearer to its undeformed state while still being slightly deformed) upon establishing the snap fit. When detaching the guard 200, the angle egress surface 200NS contacts the lip 26C and is deformed outwardly so that it can pass over the lip feature and the guard 200 can be removed from the cap 26. As the entry surface 200ES clears the lip 26C, the guard 200 returns to its undeformed state, being clear of the cap 16.

Figure 16:
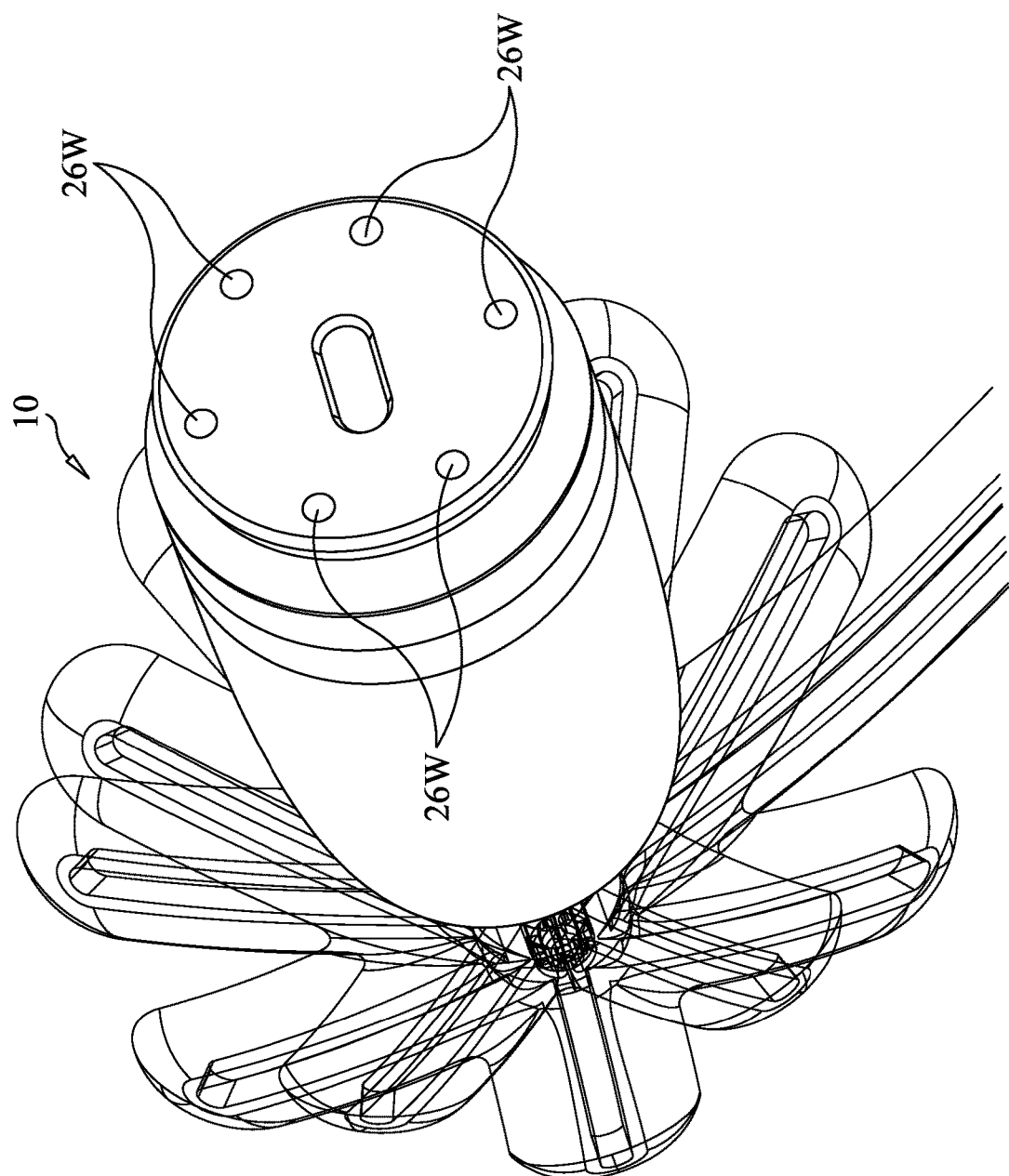
FIG. 16 is a perspective view of a device, from the proximal end, showing the proximal surface of the cap, according to an embodiment of the present invention.

The primary location of wax deposits are first made at locations 26W. FIG. 16 is a perspective illustration viewed from the proximal end of device 10 showing device 10 with the guard 200 removed, thus showing 26 exposed. The locations 26W of cap 26 have been indicated as the locations aligned with guard 200 when guard 200 is attached to the cap 26. Of course, this is only an exemplary embodiment, as the locations 26W can vary, depending upon the rotational orientation of the openings 202 of guard 200 relative to the surface of the cap 26, since guard 200 can be rotated relative to cap 26. Also, as noted previously, the guard 200 is not limited to only six openings 202, as more or fewer could be provided, resulting in more or fewer locations 26W as well. Locations 26W are the primary locations on which wax will accumulate during use of the device. Secondarily, wax may additionally accumulate along the locations of cap surface 26 opposite channels 204, as would become more likely the longer the device is used without servicing to clear or remove wax buildup.

Figure 17:
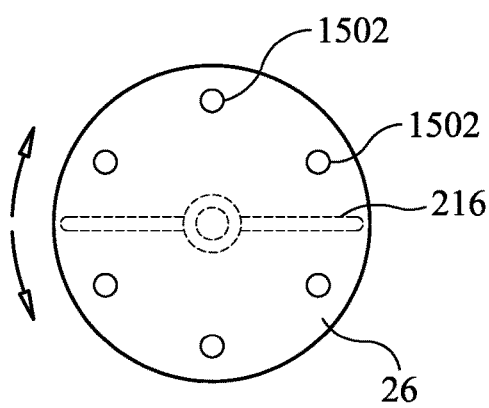
FIG. 17 schematically illustrates deposits of wax that have built up on the proximal surface of a cap, according to an embodiment of the present invention.
Figure 18:
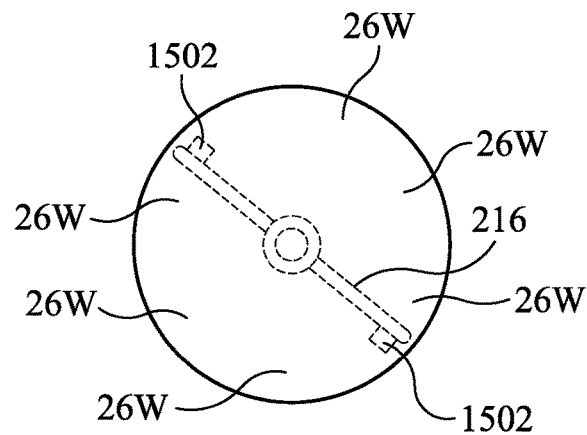
FIG. 18 illustrates a wiper moving the wax deposits of FIG. 17, according to an embodiment of the present invention.

Guard 200 may include a wiper 216 configured to wipe or move wax deposits out of a pathway through which air/sound travels from outside the device 10 to the microphone 14. In the embodiment shown in FIG. 9, wiper 216 is mounted to or integral with the distal surface 200D of guard 200 and extends therefrom by a distance sufficient to form a close fit with the proximal surface of cap 26 when guard 200 is attached to cap 26. The proximal surface of cap 26 may be concave flat or convex and the distal surface of the wiper 216ad distal surface 200D will therefore be convex, flat or concave, respectively, to form the close fit with the proximal surface of the cap 26. FIG. 17 schematically illustrates deposits of wax 26 that have built up on the proximal surface 26 at locations 26W in a manner as described above. Also, shown in phantom lines, is wiper 216 in a position that it may assume when guard 200 (not shown in FIG. 17) is attached to cap 26. In this situation, wax 1502 can be moved from the locations 26W by rotating the guard 200 (either clockwise or counter-clockwise as indicated by the arrows in FIG. 17) so that the wiper 216 contacts the wax 1502 build ups and moves them away from the locations 26W, as illustrated in FIG. 18. Upon completion of the rotation, the wax 1502 remains in contact with the wiper 216 but is moved away from channels through which sound travels, including being moved away from the locations 26W opposite the openings 202. Note that although the locations 26W are shown in the same locations that the wax 1502 occupied in FIG. 17, that this is not always the case, as the locations 26W are determined by the locations that openings 202 are placed in after the rotation. However, no matter where the locations 26W end up being, the wax 1502 buildups are ensured to be removed from the locations 26W as they remain in contact with the wiper 216 and the wiper 216 is in a fixed position between and away from openings 202.

Figure 19:
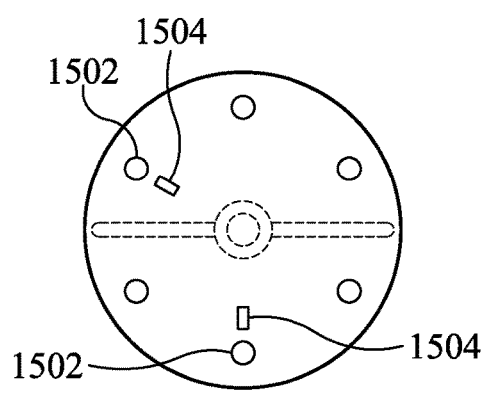
FIGS. 19-20 illustrate a wiper moving wax deposits, including wax deposits that have been made radially inwardly of the openings of the guard, according to an embodiment of the present invention.
Figure 20:
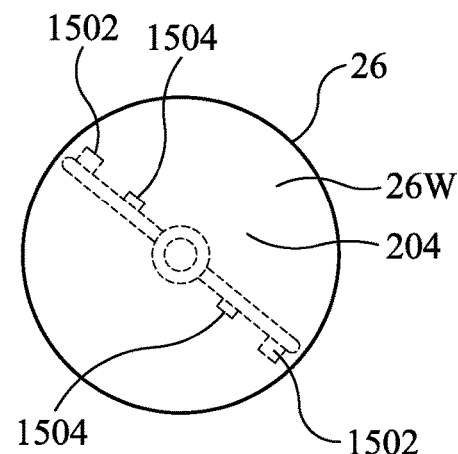

Should wax advance beyond locations 26W and along channels 204, even radially inwardly as far as central cover 206, actuation of wiper 216 as described can be performed to also wipe these wax deposits 1504 from channels 204 as well, as illustrated in FIGS. 19-20.

Figure 21:
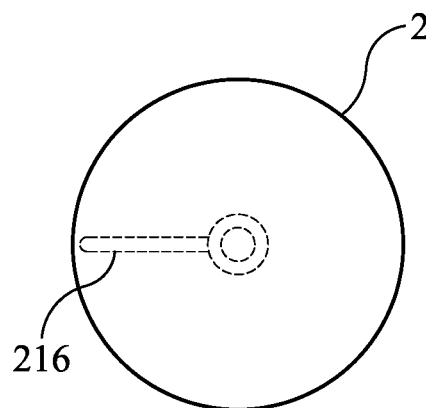
FIG. 21 schematically illustrates a single sided wiper according to an embodiment of the present invention.
Figure 22:
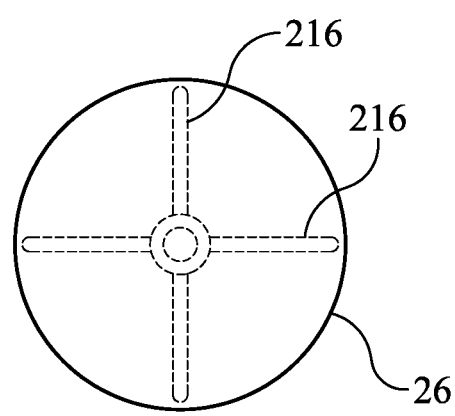
FIG. 22 illustrates a pair of double sided wipers oriented at right angles to one another, according to an embodiment of the present invention.
Figure 23:
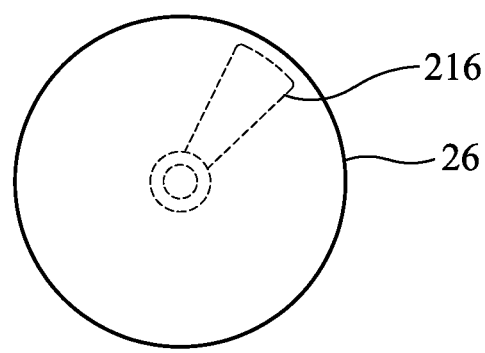
FIG. 23 illustrates a wiper in the form of a wedge, according to an embodiment of the present invention.

As noted, wiper 216 can be configured to form a close fit with the proximal surface of cap 26 when guard 200 is attached to cap 26. In at least one embodiment, the distance between the distal surface or edge 216D of wiper 216 and the proximal surface of cap 26 is about 50 µm, but may be in a range from about 1 µm to 150 µm, preferably from about 20 µm to 100 µm, more preferably from about 35 µm to about 75 µm. Preferably, the fit is as close to 1 µm as possible, so that the wax is wiped as completely as possible by action of the wiper 216 against the surface of the cap 26 and so as to avoid friction between the wiper 216 and surface of the cap 26 during relative rotation, but this is offset by the need to control costs in manufacturing, so that a somewhat looser tolerance as described is satisfactory, while keeping the manufacturing costs lower. In the embodiment of FIG. 9, the wiper 216 may extend distally from the distal surface 200D by about 0.1 mm, or in the range of 1 µm to 0.15 mm and may extend distally from channels 204 by about 0.2 mm or in the range from 0.15 mm to 0.4 mm and wiper 216 is coextensive distally with the distal surface of central cover 206. In the embodiment of FIG. 9, the wiper 216 is typically made of the same material as the guard 200, again, to keep manufacturing costs lower. Alternatively all or part of the wiper (including at least the distal edge or surface 216D) can be made of a more flexible material, such as silicone or other elastomer. This would allow the distal edge or surface 216D to contact the proximal surface of the cap 26 upon attachment of the guard 200 to the cap 26, so that rotation of the guard 200 relative to the cap 26 would result in an action similar to a squeegee or windshield wiper whereby the wiper 216 would effectively wipe the wax 1502 deposits from their current locations. However this embodiment would increase the cost of manufacture and somewhat increase the frictional forces between the wiper 216 and the cap 26 during rotation. Although shown as a dual sided blade in FIGS. 17-20, alternative forms of wiper 216 could be substituted and still perform the functions described. For example, wiper 216 may be a single sided blade as illustrated in FIG. 21; multiple blades, either dual-sided as illustrated in FIG. 22, single-sided, or a combination of dual-sided and single sided; a block as illustrated in FIG. 23; a beam, or other structure configured to function as described.

Figure 24:
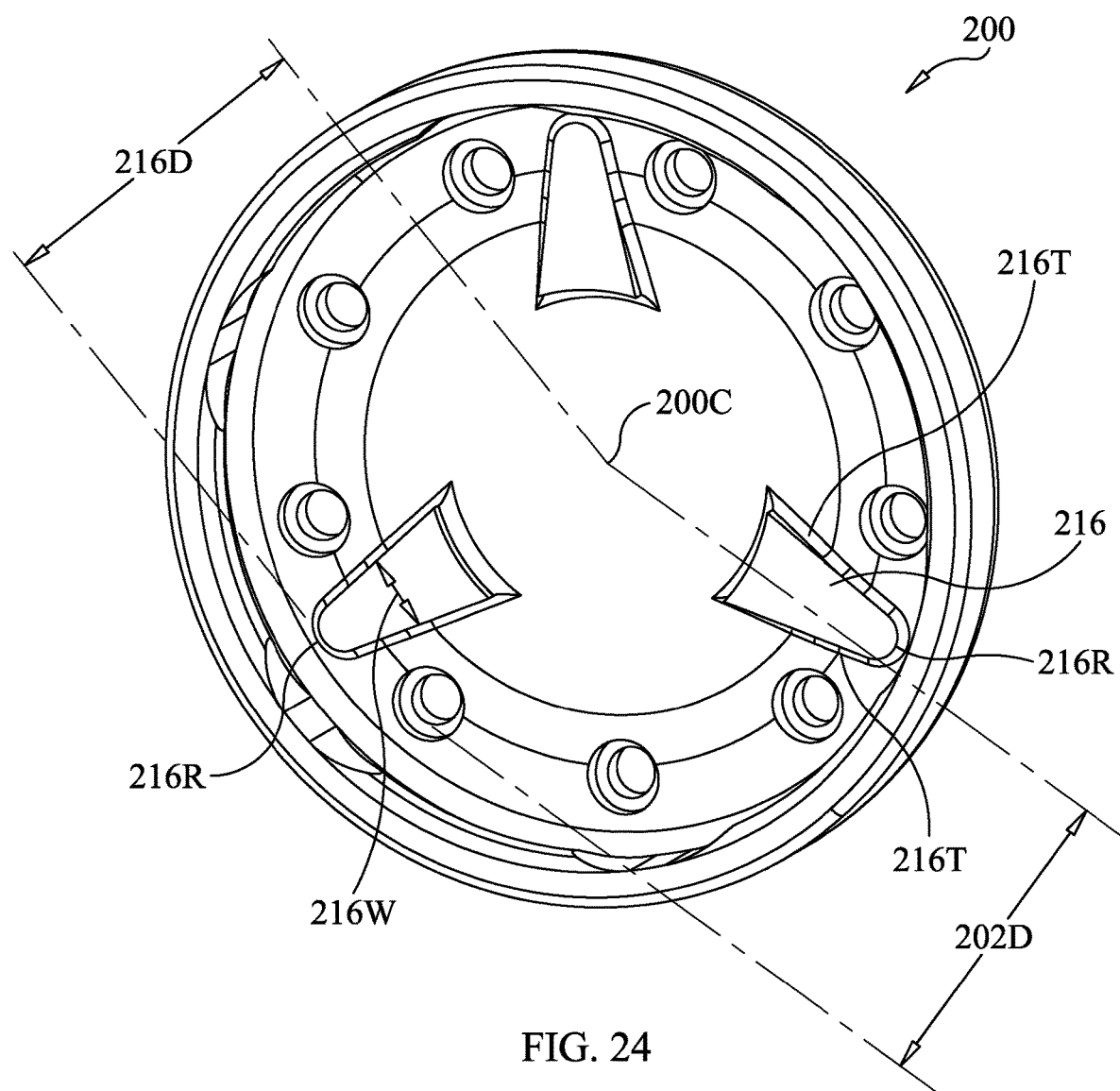
FIG. 24 is a distal end view of a guard provided with wipers configured to move wax not only rotationally, but also radially outwardly, according to an embodiment of the present invention.

FIG. 24 is a perspective view of guard 200 according to another embodiment of the present invention. In this embodiment, wipers 216 are tapered so that the width 216W gradually decreases in a direction going radially outwardly. The tapered surfaces 216T act to not only move the wax contacted in a rotational direction, but also tend to move the wax radially outwardly. Thus, wax may be moved radially outwardly to locations that are further radially from the center of the guard 200 than the radial distance at which the openings 202 are located from the center of the guard 200, thereby moving the wax completely out of the pathways through which sound and air travel from the openings 202 to the microphone 14. Wipers 216 extend from the distal surface of the guard and may otherwise be configured like described previously. It is further noted that the radially outmost ends 216R of wipers 216 may extend from the center 200C of guard 200 by a distance 216D that is greater than a distance 202D by which the radially most outward point of the periphery of opening 202 extends radially from the center 200C. This enables wax to be moved along the tapered surface(s) 216T to a location radially distant of the opening 202. Although three wipers 216 are shown in FIG. 22, it is noted that one, two or more than three such wipers may alternatively be employed.

Figure 25:
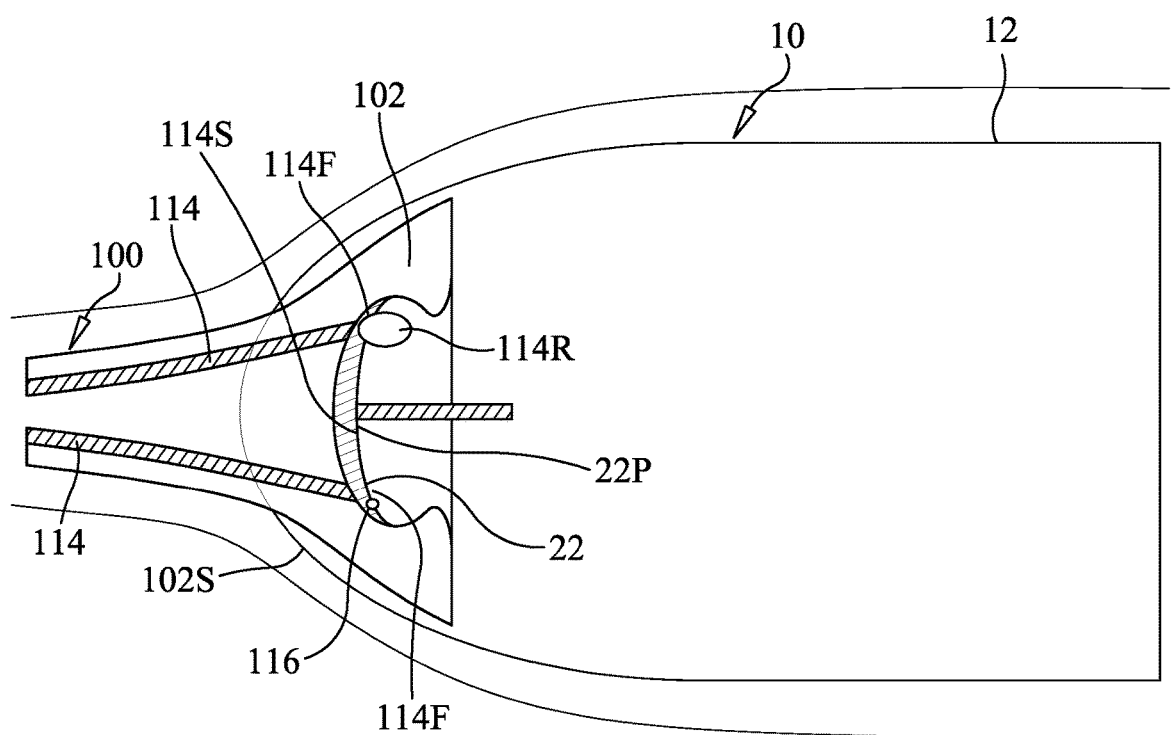
FIG. 25 schematically illustrates a wiper provided to extend proximally from a proximal surface of a mating connector of a proximal guard, according to an embodiment of the present invention.

The provision of one or more wipers 216 for clearing wax deposits from air/sound channels is not limited to those applied at the proximal end portion of the device 10, such as those described with regard to guard 200 above. Additionally or alternatively, one or more wipers 116 may be provided with guard 100, 100M. FIG. 25 schematically illustrates wiper 116 provided to extend proximally from a proximal surface of mating connector 102, such that rotation of the guard 100 relative to the shell 12 causes the wiper 116 to rotate relative to the distal surface of distal tip 22, thereby wiping wax having been deposited in the portions of the pathways 114S formed by the interface between mating connector 102 and distal tip 22. Optionally one or more wax reservoirs 114R may be formed in distal tip 22 proximally of the location(s) where the convoluted pathways/channels 114 interface between the mating connector 102 and the distal tip 22, and extending proximally of the interface, as shown in FIG. 25. In this optional arrangement, wax may be deposited in reservoir(s) 114R by advancing straight into the same, as the path of least resistance, rather than making a sharp angular change in direction so as to travel into the transverse channel 114S. Whether or not the reservoirs(s) is/are employed, relative rotation between guard 100 and shell 12 causes the wiper 116 to effectively clear wax deposits within channels 114S. Preferably, the channel(s) 114 interface between the mating connector 102 and tip 22 at locations 114S forming the transverse channels after traveling through channels or convoluted pathways 114. The one or more openings 22P in the distal tip are located radially inwardly of the locations 114F where the channels 114 extend from interfacing between the mating connector 102 and distal tip 22, and through the mating connector 102.

It is further noted here that any or all components of the guards 100, 100M, 200, as well as tab 300 and/or shell 12 may be coated with one or more hydrophobic and/or oleophobic coatings to further inhibit ingress of wax and/or moisture. Further, one or more components of the guards described herein may be coated with various materials and compositions to enhance the lubricity, alter the friction, adjust the hydrophobicity, or increase the stability in the chemical, environmental, and physical conditions of the target space or opening of the projecting members. In all embodiments herein, the shell 12 may be textured and or coated to enhance the friction of the outer surface thereof with the hand/fingers of a user to aid in gripping it during removal and/or attachment of a guard 100, 100m, 200 thereto or therefrom.

Likewise any or all components of the guards 100, 100M, 200, as well as tab 300 and/or shell 12 may be coated with or contain various materials to allow for administration of a pharmacological agent or composition to biological tissue. The coating material can thus comprise, without limitation, active agents or drugs, such as anti-inflammatory coatings, and drug eluting materials. The coating material can additionally or alternatively include non-pharmacological agents.

As noted previously a removal tab 300 may be attached to a space access device 10 to have a length that extends out of a space or opening in which the space access has been inserted, so that the tab 300 can be pulled out to extract the space access device 10 from the space or opening. FIGS. 1-2 illustrate pull tab 300 according to an embodiment of the present invention. Pull tab 300 is formed as an integral part of the wax management guard 100 in FIG. 2 and may be made of the same material as the outwardly extending members 106 and base 104. The length 300L of the pull tab 300 is sufficient so that at least a proximal end portion 300P extends out of the ear canal when space access device 10 is installed in the ear canal in an operative position. For example, the length may be a value in a range from about 20 mm to about 40 mm, typically from 25 mm to 35 mm. In one specific example, length 300L was 28 mm. The "extension length" (length to which the pull tab 300 extends beyond the proximal surface of guard 200 when installed on device 10 when pull tab 300 is folded down against the surface of the shell 12) is a value in a range from about 7 mm to about 20 mm, typically from about 9 mm to about 15 mm. In one specific example, the extension length was 10 mm. In another specific example, the extension length was 12 mm. In still another specific example, the extension length was 14 mm. The lengths of the outwardly extending members 106 may be in a range from about 4 mm to about 20 mm and may be all the same or some or all can be different from one another. In one specific example, the lengths of the outwardly extending members were all the same and we about 14.32 mm. In another specific example, the lengths of 106 were all equal and about 7 mm. In another specific example, the outwardly extending members 106 all had a length of 11 mm. In another specific example, the outwardly extending members 106 all has a length of 15 mm.

In such an embodiment the entire space access device 10 is inserted within the ear canal such that only the proximal end portion 300P can be seen extending out of the ear. Alternatively, pull tab 300 could be used similarly to extract a space access device 10 wherein only a portion of the device is contained within the opening or space and a proximal end portion of the device 10 extends out of the space or opening during use. After repeated use, or even on a first use, it is possible that a pull tab 300 will fail and break off without successfully removing the space access device 10 first. In order to provide more reliability against failure, the pull tab 300 of FIGS. 1-3 provides redundancy in that two or more (two in the embodiment of FIGS. 1-3) tab legs 302 are integral with the base 104 from which the pull tab 300 and outwardly extending members 106 extend. To make the pull tab 300 easier to operate, the proximal end portions of the legs 302 may be made integral or otherwise connected to facilitate grasping and pulling on all of the tab legs 302 simultaneously during use. Optionally the proximal end portions of the legs 302 may remain independent and detached from one another, but this is not preferred. Because of the redundancy provided by the multiple legs 302, if one of the legs 302 should fail or break off when pulling on the pull tab 300, another leg 302 remains connected to the device 10 to finish the extraction.

Additionally, a gap or slot 304 extending therebetween to facilitate airflow therethrough in the same way that slots 107 of outwardly extending members facilitate airflow as described. In such an instance, pull tab 300 serves a dual function as both a pull tab extractor and also as one of the outwardly extending members 106 as it contacts the ear canal to provide a similar anchoring function and provides an air flow pathway 304. Because the pull tab 300 can be integrally formed with the guard 100, it is automatically exchanged each time a guard 100 is exchanged, thereby further reducing the risk of failure due to fatigue resulting from too many uses.

Although pull tab 300 may be formed of the same material as the outwardly extending members 106 and 104 as noted above (for example, all can be made of the same silicone), alternatively, pull tab 300 may be fortified to make it of stiffer and or stronger materials to further reduce the risk of failure. For example, the pull tab may be made of a mixture of materials to accomplish this result, or use a stiffer or stronger material. For example, a stiffness additive, such as a fiber and/or thermoplastic additive may be included in the silicone used to make the pull tab. Proprietary stiffeners available from Momentive Performance Materials Inc., Waterford, N.Y., USA may be used. Outwardly extending members 106 and base 104 may be made from a relatively softer material. Even when all components are silicone, the silicone used to make pull tab 300 can have a greater hardness or stiffness than that used to make outwardly extending members 106 and base 104. In one embodiment, outwardly extending members 106 are made from a 40 A (Shore hardness) silicone and the pull tab 300 (tab legs 302) are made from 65 A (Shore hardness) silicone combined with a stiffness additive.

Figure 26:
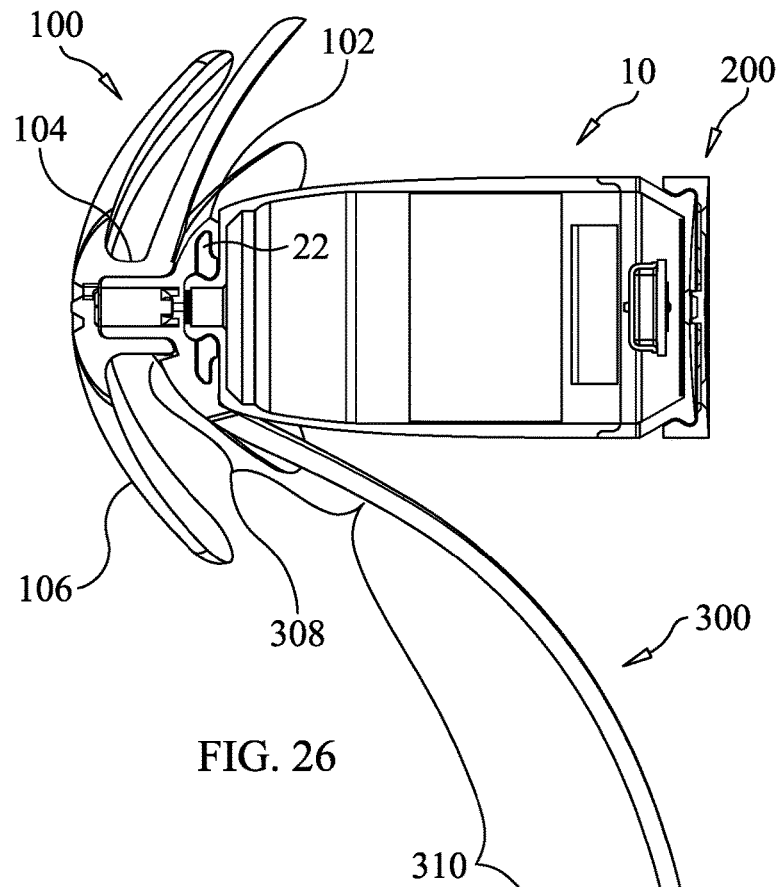
FIG. 26 illustrates an embodiment of space access device that employs a pull tab that is made of a material that is stronger in tensile strength than the material from which outwardly extending members are made, according to an embodiment of the present invention.

FIG. 26 illustrates an embodiment of space access device 10 that employs a pull tab 300 that is made of a material that is stronger in tensile strength than the material from which outwardly extending members 106 and base 104 are made. In this embodiment as well as all other embodiments of pull tab 300 described herein a nub 306 or other protrusion (one or more) can be provided on the proximal end portion of the pull tab 300 near the proximal end, to facilitate grasping by the user as he/she pulls on the pull tab 300 to perform an extraction. The nub 306 helps to prevent the user's fingers from slipping off the proximal end of the pull tab 300 during the extraction operation. Another feature that can be provided with a pull tab 300, whether or not it is made from the same material as outwardly extending members 106, is a curvature that is configured to conform to the space or opening into which the space access device is inserted. In the case where the space access device is inserted into the ear canal, the pull tab 300 has a double curvature configured to conform to the curvature of the ear canal and the Intertragal Notch of the Pinna. Thus, a distal portion 308 of the pull tab 300/pull tab legs 302 curve so that they are concave on a side facing toward the shell 12 and convex facing toward the ear canal, and transition proximally of this first curve to a second curvature 310 that is curved in the opposite direction so as to better follow the contours of the ear canal and so that the proximal end portion can be tucked into the Intertragal Notch making it even less visible.

The embodiment of FIG. 26 employs a distal tip 22 that has a significantly larger outside diameter than that of the distal tip 22 shown in FIG. 2. For example, the embodiment of FIG. 2 has a distal tip 22 having a smallest outside diameter in a range from about 1.2 mm to about 1.8 mm with snap interference features extending outwardly therefrom by a distance in a range from about 0.1 mm to about 0.2 mm, making the largest outside diameter in a range from about 1.4 mm to 2.2 mm. The embodiment of FIG. 26 has a larger distal tip 22, as noted, having a smallest outside diameter in a range from about 2.5 mm to about 3.1 mm with snap interference features extending outwardly therefrom by a distance in a range from about 0.1 mm to about 0.2 mm, making the largest outside diameter in a range from about 2.7 mm to 3.5 mm. Consequently, the mating connector also has a larger inside diameter. This configuration has been found to make it even easier to attach and detach the guard 100 from the shell 12 without the use of tools, as alignment of the mating components is much easier, and the large dimensions lend more readily to the flexing required to form the snap fit.

Figure 27:
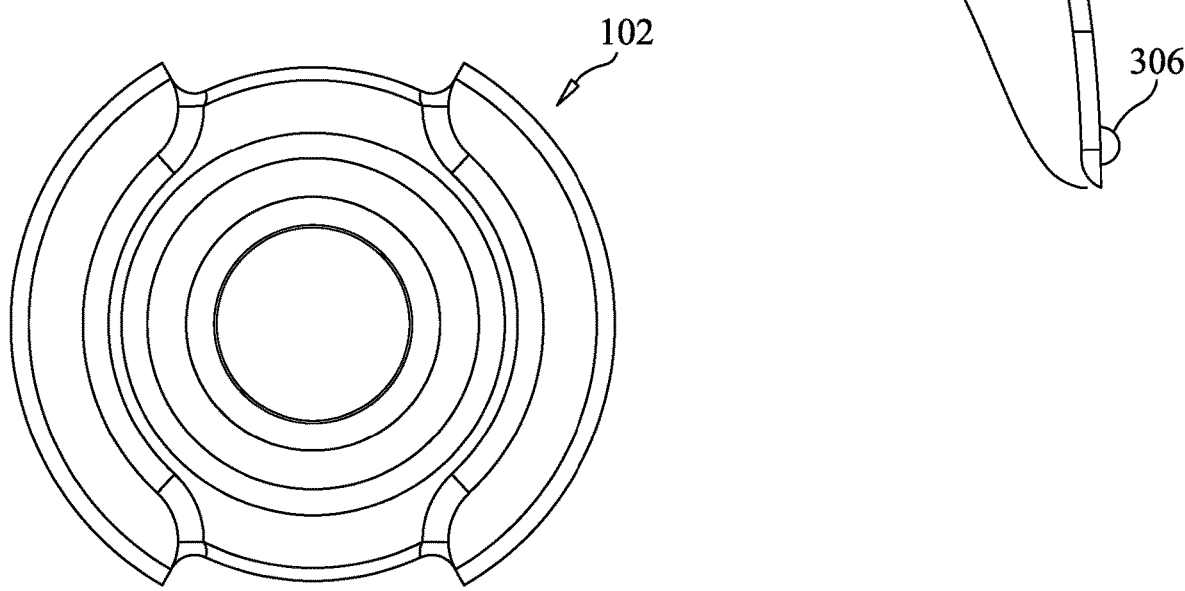
FIG. 27 shows a proximal end view of a mating connector to which a pull tab is to be integrally formed, according to an embodiment of the present invention.
Figure 28:
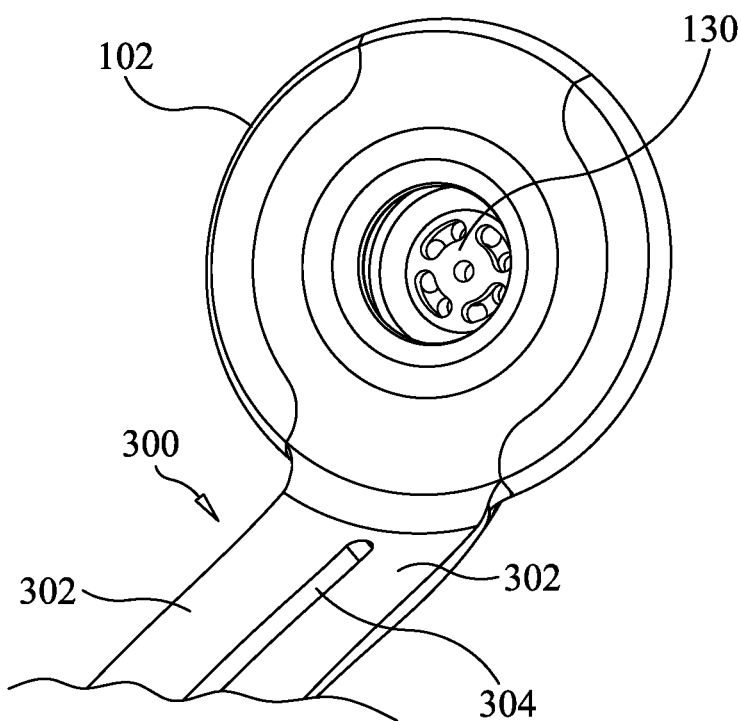
FIG. 28 is a partial view showing a pull tab having been integrally formed with the mating connector of FIG. 27.

The embodiment of FIG. 26 employs a modular guard 100 of a type described above. However, an integral guard may also use a pull tab 300 having different material characteristics from the outwardly extending members 106 and base 104. FIG. 27 shows a proximal end view of mating connector 102 to which pull tab 300 is to be integrally formed. Mating connector 102 may be made of a more rigid material than that used to make the pull tab 300, for example, mating connector 102 may be made of Nylon. FIG. 28 is a partial view showing the pull tab 300 having been integrally molded with the mating connector 102. In one non-limiting example, the pull tab 300 may be molded from silicone with a stiffening agent and the mating connector may be made of Nylon. Other material may be used where the pull tab 300 is more flexible than the mating connector 102. The filter 130 is also molded along with the pull tab 300 of the same material.

Figure 29:
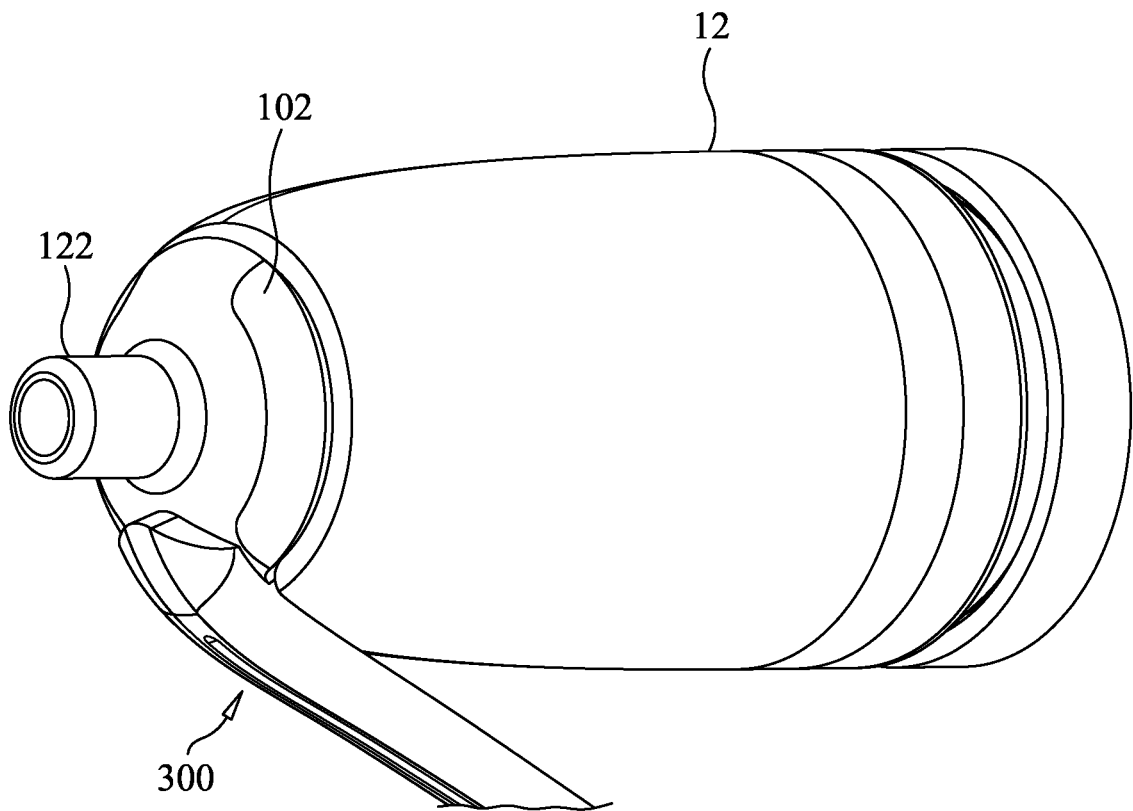
FIG. 29 illustrates the integrated mating connector and pull tab of FIG. 28 having been snap connected to a shell, according to an embodiment of the present invention.

FIG. 29 illustrates the integrated mating connector 102/pull tab 300 having been snap connected to the shell 12 in a manner as described previously. From FIG. 29 it can be seen that the mating tip 122 has also been integrally made from the same material as that used to make the pull tab 300. One or more modules 100M having outwardly extending members 106 formed of a softer material can next be assembled to the subassembly shown in FIG. 29 in the same manner as described previously with regard to FIGS. 13A-13E.

Figure 30:
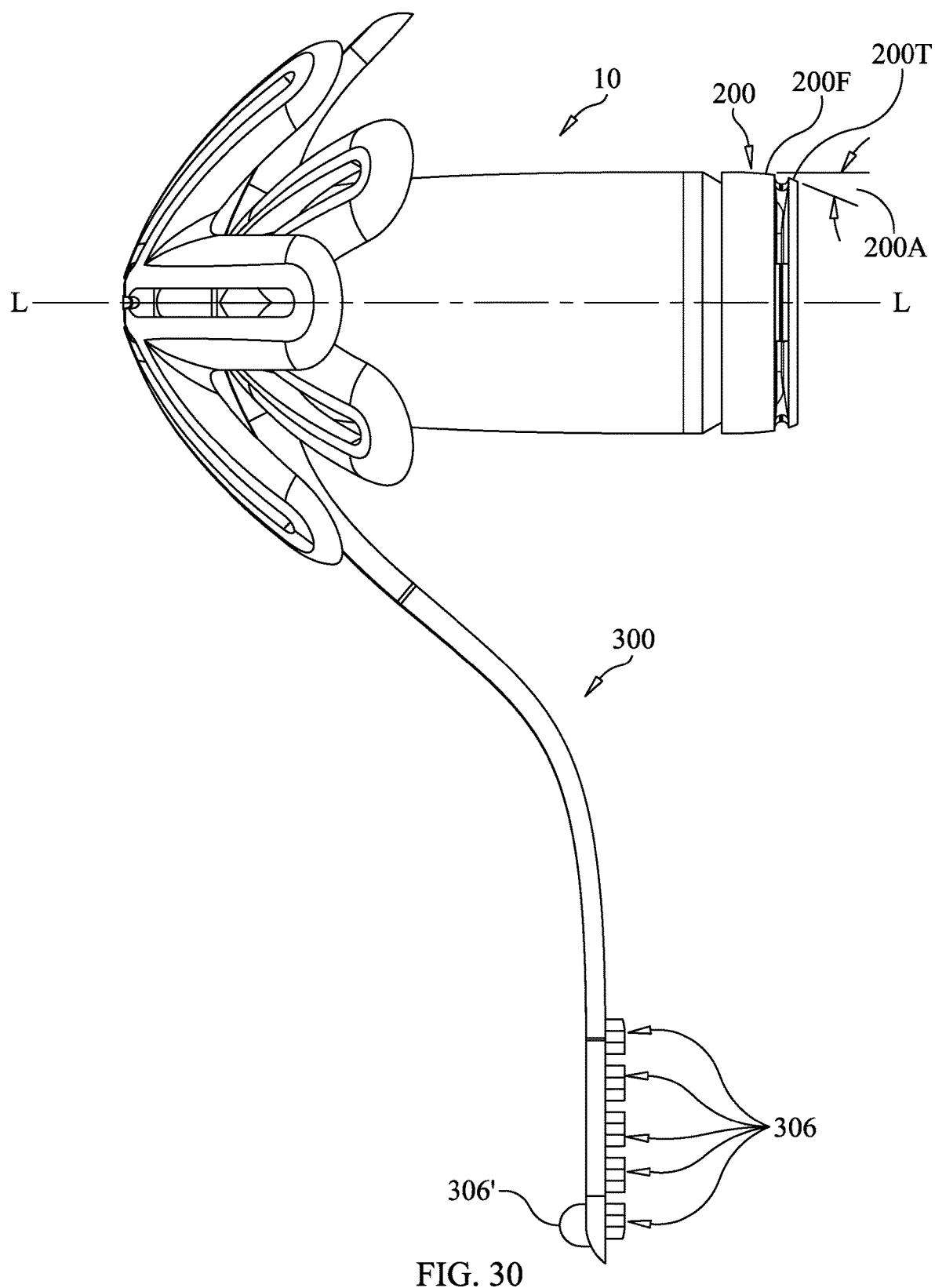
FIG. 30 shows a space access device according to another embodiment of the present invention.

FIG. 30 shows an embodiment of space access device that is similar to the embodiment shown in FIG. 26, so that similar features are not described here again, for sake of brevity. In the embodiment of FIG. 30, pull tab 300 includes multiple nubs or other friction enhancement features 306 extending along a proximal end portion of the pull tab 300 to help prevent the user's finger(s) from slipping relative thereto, when pulling on the pull tab 300. Optionally, one or more nubs or other friction enhancement features 306' may also be provided along the pull tab 300 at a location(s) opposite the one or more features 306. The proximal end portion of the guard 200 may be tapered 200T as illustrated in FIG. 30, such that the tapered surface 200T angles toward the longitudinal axis L-L in a direction toward the proximal end of the device 10. The taper angle 200A between the surface 200F that is parallel to the longitudinal axis L-L and the tapered surface 20T may be in a range from greater than zero degrees to 60 degrees, typically from 15 degrees to about 45 degrees. In one specific example, taper angle 200A was about 30 degrees. By tapering the proximal end portion of the guard 200 as described, this helps to prevent the edges of the proximal surface of the guard 200 from catching on the Tragus of the ear when the device 10 is pulled out of the ear canal by pulling the pull tab 300.

Figure 31:
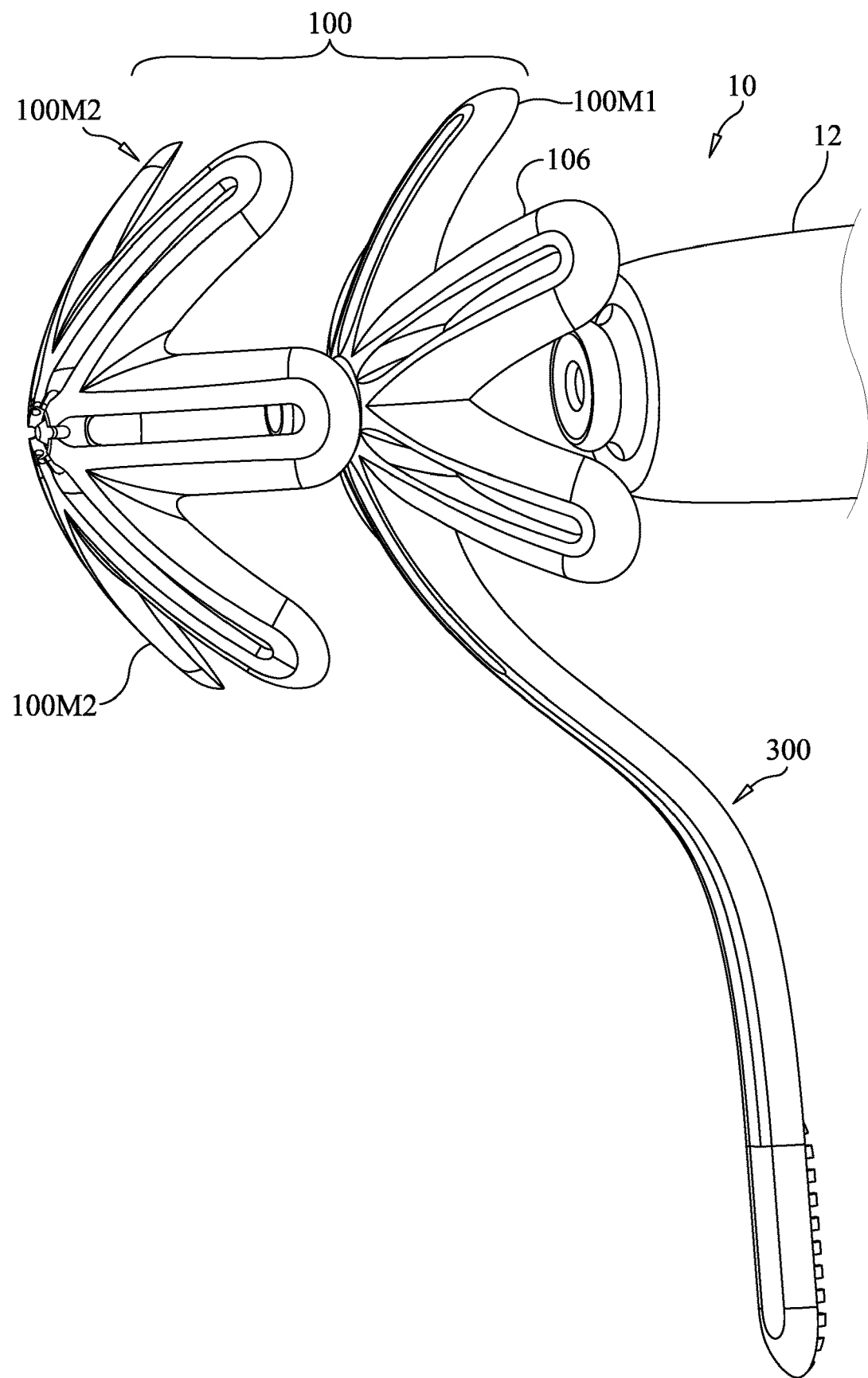
FIG. 31 is a partial, exploded view of the guard and a distal end portion of the shell of the device shown in FIG. 30.

FIG. 31 is a partial, exploded view of the guard 100 and a distal end portion of the shell 12 of the device 10 shown in FIG. 30. In this embodiment, the guard 100 may be manufactured in modules, similarly to that described with regard to FIGS. 13A-13E above. In this embodiment the first module 100M1 (clip and pull tab) includes the mating connector 102 (not shown in FIG. 31) and pull tab 300 as well as a first set of outwardly projecting members in the form of slotted petals 106. The second module (crown) 100M2 includes a second set of outwardly projecting members in the form of slotted petals 106. The connector 102 may be made from a harder material than that of the remainder of the module 100M1, like described above with regard to FIG. 28, or alternatively, the entire module may be made of the same material, such as a reinforced or stiffened silicone that has relatively low hardness but relatively high stiffness. Stiffeners may include, but are not limited to aramid fibers.

Figure 32:
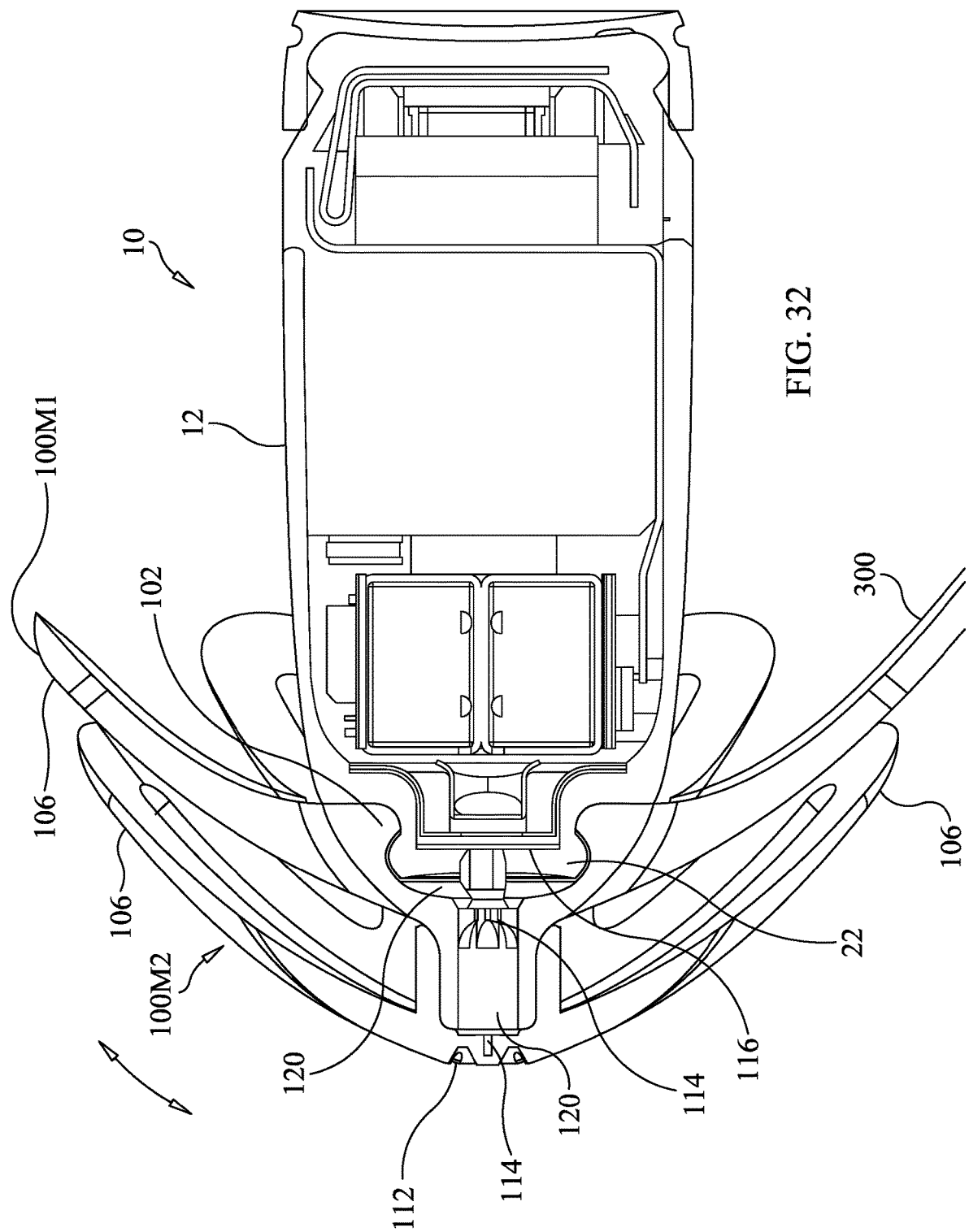
FIG. 32 is a longitudinal sectional view of the device of FIG. 30.

FIG. 32 is a longitudinal sectional view of the device 10 of FIG. 30. The first module 100M1 is shown having the connector 102, petals 106 and pull tab 300 all made of the same material, such as a stiffened silicone, for example. Alternatively, the connector 102 and pull tab 300 can be formed with the stiffened silicone and the petals 106 can be formed (such as with a second shot of a two-shot molding process) of less stiff, softer, silicone. The module 100M2 may be formed all of the same material, such as a less stiff, softer silicone. For example, module 100M2, including petals 106 and petals 106 of module 100M1 may be formed from 40 A Shore durometer silicone, and the stiffened silicone used to make pull tab 300 and connector 102 may be greater than 40 A Shore hardness, typically in the range from about 50 A Shore hardness to 80 A Shore hardness, more typically in the range from 60 A Shore hardness to 70 A Shore hardness. The stiffened material is provided to increase tear resistance, increase stiffness (Young's Modulus) to improve performance of the connector 102 and pull tab 300.

Figure 33:
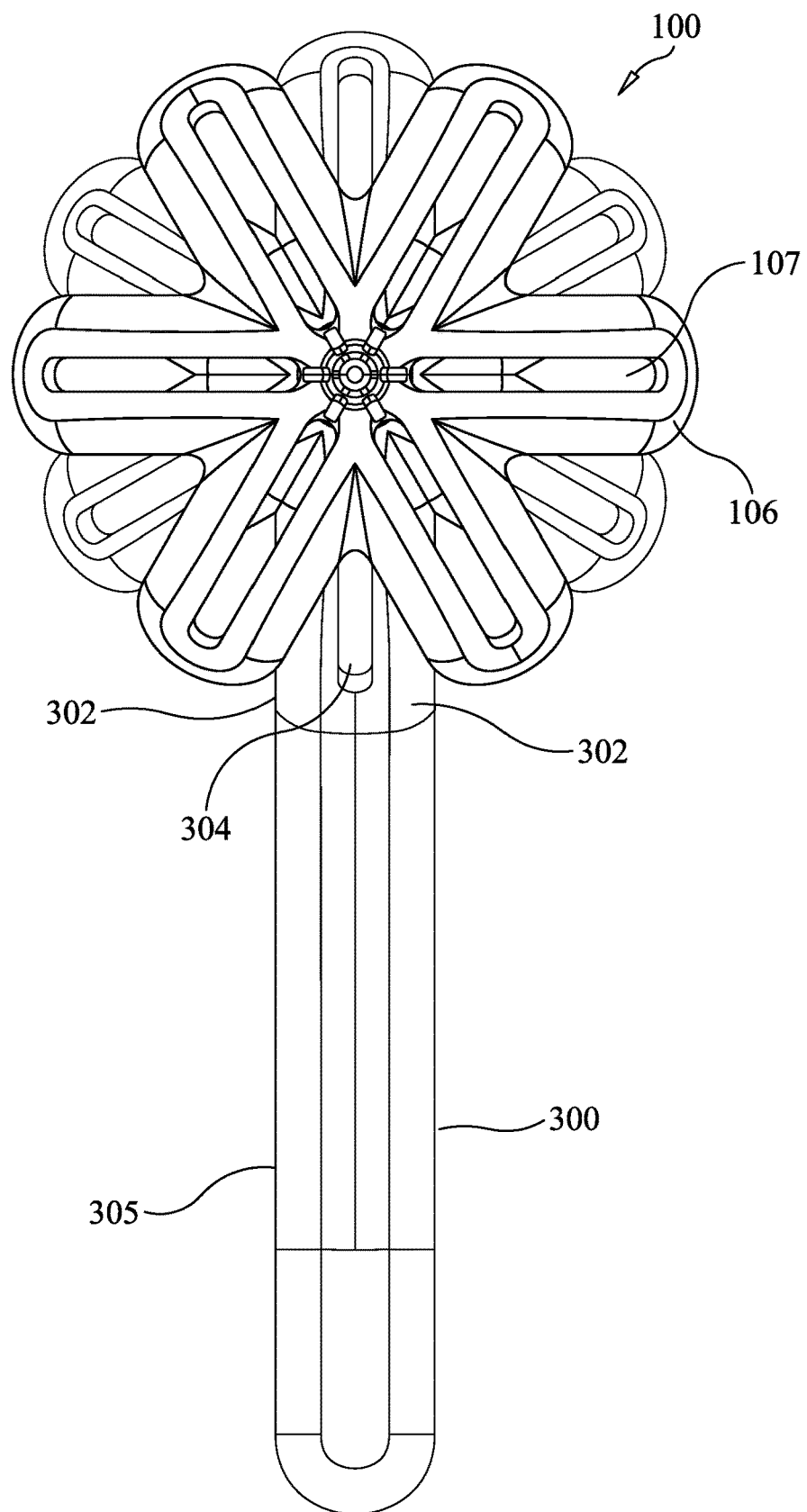
FIG. 33 shows a distal end view of a distal guard according to an embodiment of the present invention.

FIG. 33 shows a distal end view of guard 100 according to an embodiment of the present invention. Notably the slot 304 formed in pull tab 300 in this embodiment has substantially the same length as the slots 107 of outwardly extending members/petals 106. Thus the portion of pull tab 300 that incudes slot 304 still functions to allow airflow therethrough with the same performance as slots 107 in petals 106, Also legs 302 are still provided to perform the redundancy function described above. However, because the slot 304 is shorter than the slot in the embodiment of FIG. 2, the portion 305 of the pull tab 300 proximal of slot 304 is stronger and stiffer, as it is not slotted, but is formed as a solid, single length portion of the pull tab 300. The modules 100M1 and 100M2 may be connected via adhesive (e.g., silicone adhesive) or other means of attachment to form the guard 100. Although the components may be made of clear silicone, they can alternatively be colored. For example, materials having different stiffnesses may be color coded to indicate such. Color coding need not be limited to stiffness characteristics, as the color coding may be used to differentiate any differentiable characteristics of the components. As one non-limiting example, a first color could be used to identify module 100M1 and a second color could be used to identify module 100M2.

One or more openings 112 may be provided as an initial filter in the guard 100. In the embodiment of FIG. 32, the filter has only a single opening 112 that leads through a convoluted pathway 114 of any of the types described above to a reservoir 120, One or more additional convoluted pathways 114 are in fluid communication with a second reservoir 120 formed between the connector 102 and the distal tip 22. One or more wipers 116 may extend proximally of the proximal surface of connector 102 so that, upon rotation of guard 100 relative to shell 12, wiper 116 contacts wax or other debris in the second reservoir between the proximal surface of connector 102 and distal surface of distal tip 22 and moves the wax or debris to accomplish at least partial clearing of a pathway in fluid communication with the receiver of the device 10. The guard 100 thus provides a first molded in wax guard with a convoluted pathway in module 100M2 and a second wax guard with convoluted pathway in module 100M2. The guard 100 is flexible and can flex/rotate/tilt relative to the longitudinal axis of the device 10 (for example, but not limited to, the directions of the arrows shown in FIG. 32). That is, the device 10 is relatively rigid only to the distal tip 22. Distal of this location, the guard 100 is flexible and also provides a soft, atraumatic tip as a distal end of the device. This facilitates navigation of the device 10 through the ear canal, and placement of the device 10 in a desired location, as the ear canal may include curvature where the device 10 is to be placed.

Figure 34:
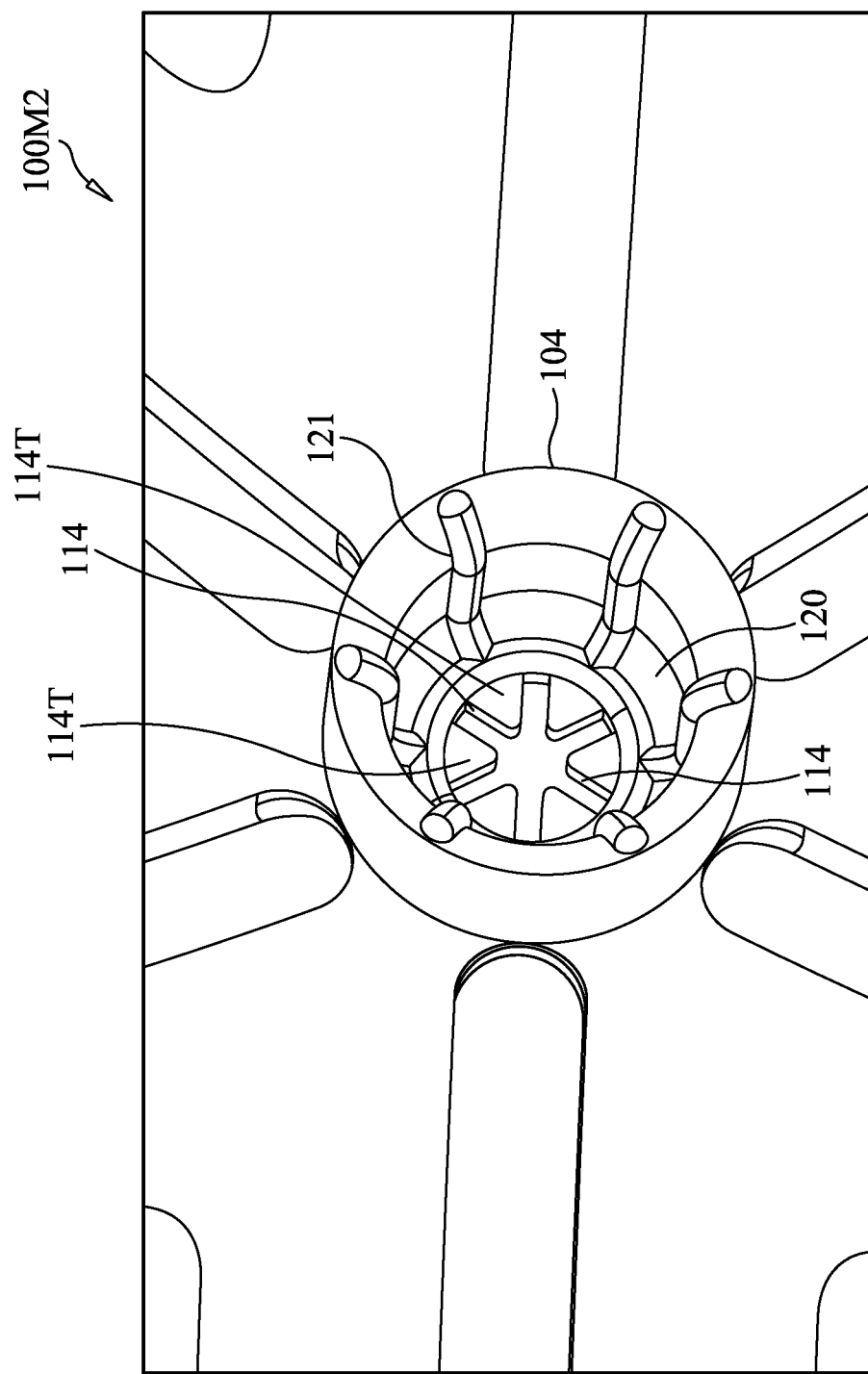
FIG. 34 is an enlarged, partial, proximal end view of a module of a distal guard, according to an embodiment of the present invention.

FIG. 34 is an enlarged, partial, proximal end view of module 100M2 showing the convoluted pathways 114 connecting the distal opening of the module 100M2 with the reservoir 120. Overlapping features 114T, such as tabs, ledges or other features that prevent airflow are arranged so that no straight through airflow pathway is provided in the module 100M2, Although white spaces or openings appear to be shown in FIG. 34, this is due to the perspective of the figure. No straight through pathways are provided, as air flow, wax and everything else must navigate around the angular impediments forming the convoluted pathway. Ribs or bosses 121 may be provided with a predetermined thickness to control the glue thickness that results when adhering the modules 100M2, 100M1 together. The outside diameter/dimension of the base 104 is designed to be kept to a minimum, for anatomical comfort, relative to the minimum port size of the reservoir 120 designed to achieve the desired acoustic results.

Figure 35B:
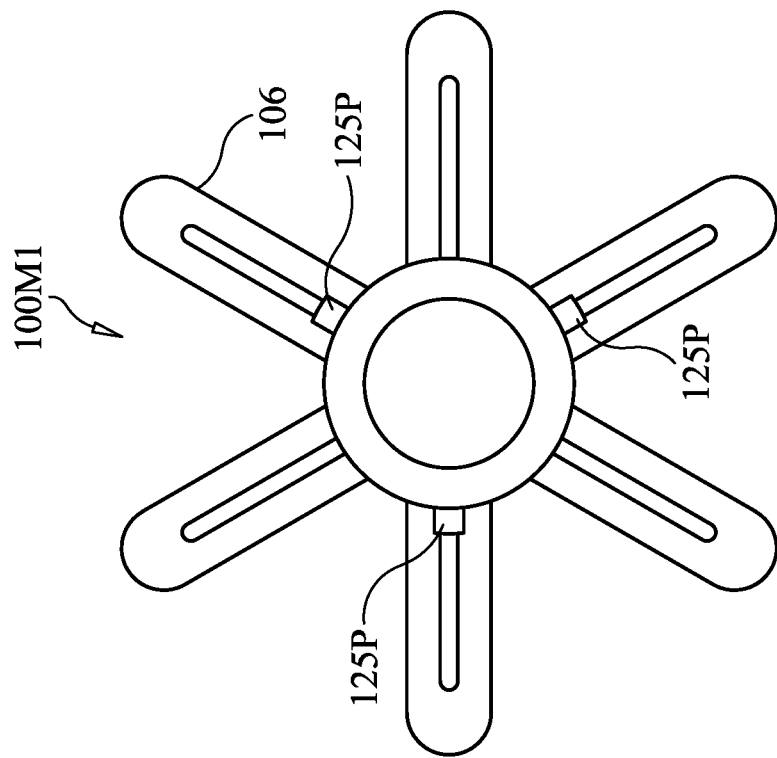
FIGS. 35A and 35B illustrate clocking features that may be provided to ensure that the rotational orientation of outwardly projecting members of interconnecting modules are fixed in the intended relative orientation relationships, according to an embodiment of the present invention.
Figure 35A:
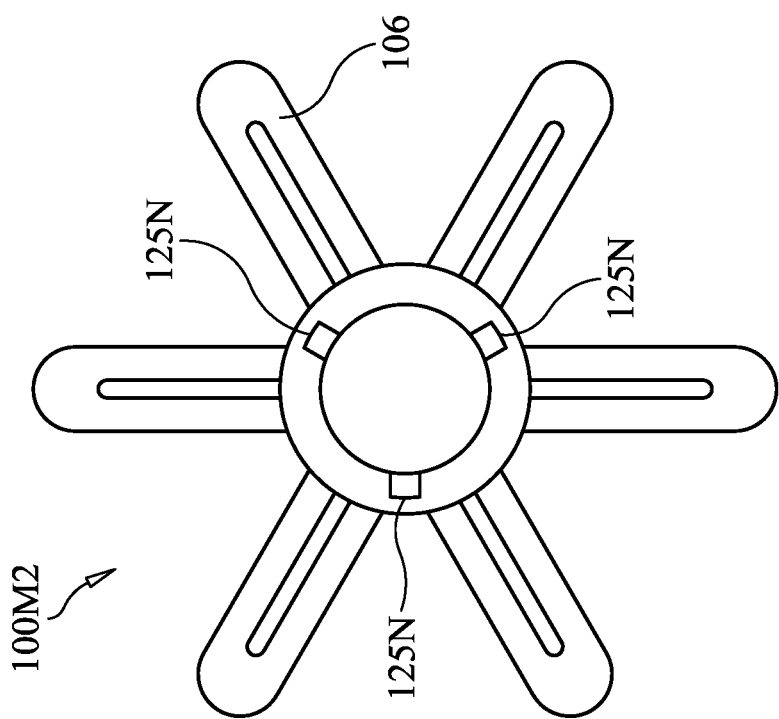

Optionally, clocking features may be provided to ensure that the rotational orientation of the outwardly projecting members 106 of the first module 100M1 relative to those of the second module 100M2 are fixed in the intended orientation relationship. The intended orientational relationship may be offset, as shown in FIG. 33, for example, aligned, or offset by a greater or lesser angulation than that shown in FIG. 33. Any orientation may be predetermined by the appropriate placement of the clocking features 125. Any feature that functions to predetermine the rotational orientation of one set of outwardly projecting members on a first module with respect to a second set of outwardly projecting members on a second module can be used as clocking features. In the proximal end illustration of module 100M2 of FIG. 35A, clocking features 125N are notches or other recesses formed in the module 100M2 to receiving projections 125P extending from module 100M1 as show in the distal end illustration in FIG. 35B. When these features mate, they ensure the rotational orientation of a first set of outwardly projecting members 106 relative to a second set of outwardly projecting members 106. For example, the clocking features may be configured so that the outwardly extending members of the second modular component are located to cover the gaps intermediate the outwardly extending members of the first modular component, when viewed in a direction along the longitudinal axis, like the arrangement shown in FIG. 3. Alternatively, the clocking features can be configured so that the outwardly extending members of the second modular component are aligned with (overlay) the outwardly extending members of the first modular component, when viewed in a direction along the longitudinal axis. Further alternatively, the clocking features can be configured to provide any angular offset between the previous two examples, i.e., between being completely aligned, or extending intermediately in the gaps. This allows the guard to be designed to allow varying degrees of air flow past the outwardly extending members, wherein the aligned orientation allows the greatest air flow therepast, and the orientation where the outwardly extending members of the second modular component are located to cover the gaps intermediate the outwardly extending members of the first modular component restricts the amount of airflow the greatest.

Figure 36:
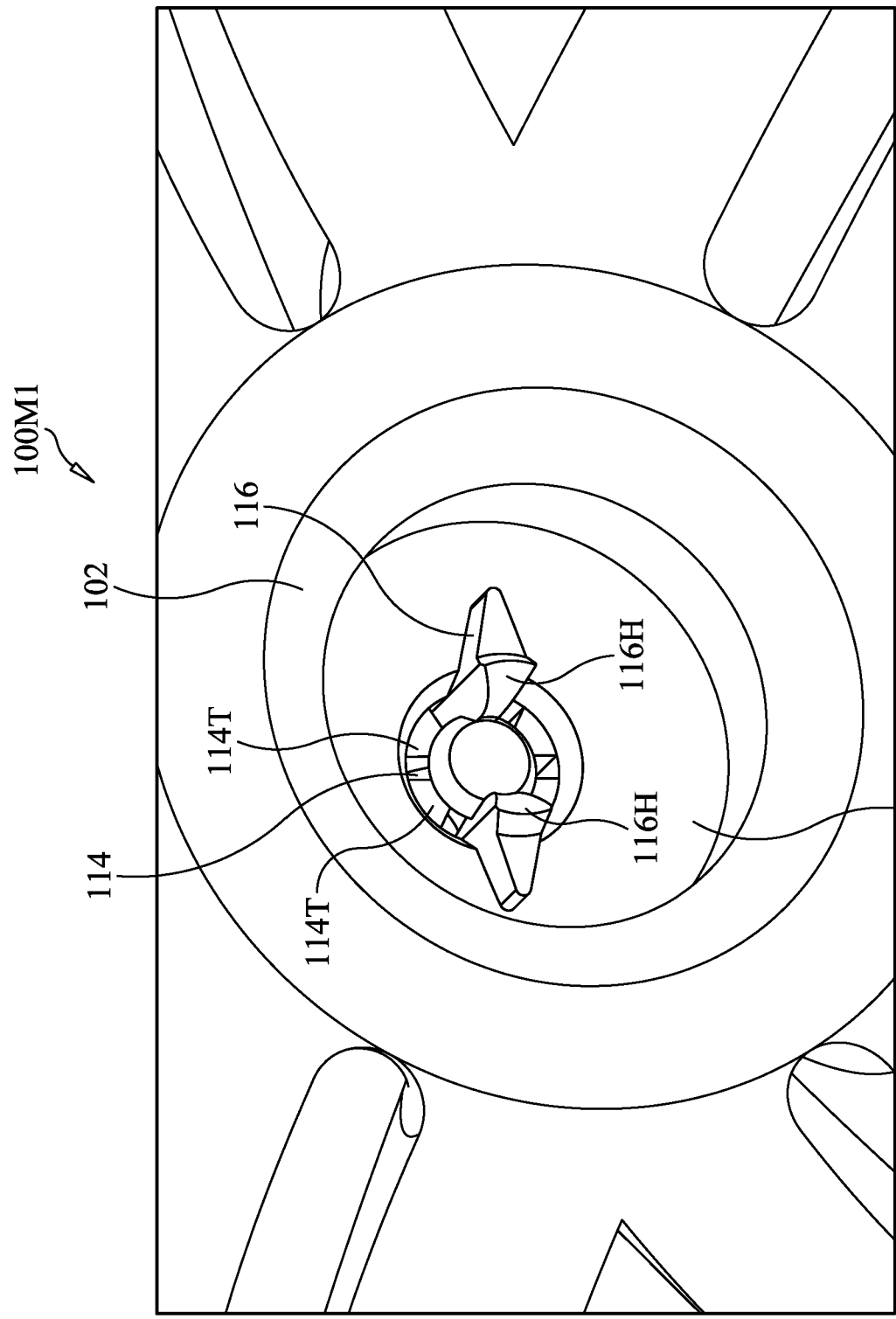
FIG. 36 is an enlarged, partial, proximal end view of a module showing the convoluted pathways connecting the distal opening of the module with a reservoir, according to an embodiment of the present invention.
Figure 37:
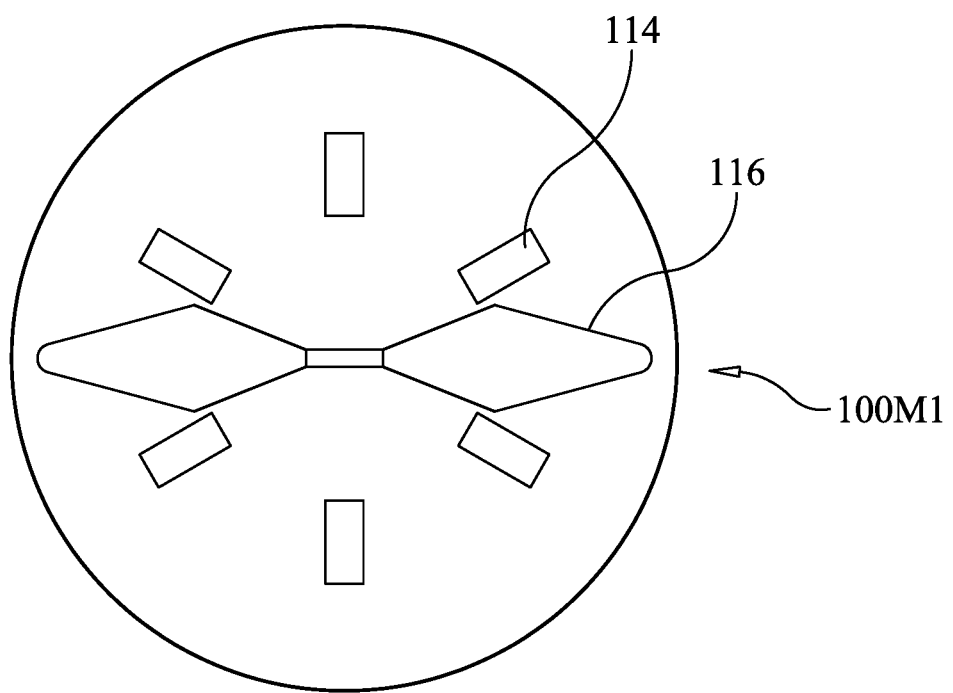
FIG. 37 illustrates an angled wiper extending proximally into a reservoir of a module, according to an embodiment of the present invention.

FIG. 36 is an enlarged, partial, proximal end view of module 100M1 showing the convoluted pathways 114 connecting the distal opening of the module 100M1 with the second reservoir 120. Overlapping features 114T may be provided in the same manner as that described above with regard to module 100M2 in FIG. 34 to form convoluted pathways 114. Additionally, at least one wiper 116 projects proximally into the reservoir 120 and is configured to be rotated to move wax and other debris as already described above. In the embodiment shown in FIG. 36, wiper 116 includes head regions 116H that extend further proximally than the remainder of the wiper 116 formed radially outwardly thereof. Head regions form notches with the remainder of the wiper 116. Head regions 116H are configured to insert into the receiver port and scrape the inner wall of the receiver port when the wiper 116 is rotated relative to the receiver to move wax and/or other debris out of the receiver port. FIG. 37 illustrates an angled wiper 116 extending proximally into a reservoir of a module 100M1. The angled wiper 116 functions to move wax/debris like that described with the angled wiper 216 of FIG. 24.

The shell 12 and cap 26 are hermetically sealed so that the only ways that air, wax, moisture or other debris can enter into it are through the ports provided at the proximal and distal end thereof.

Figure 38:
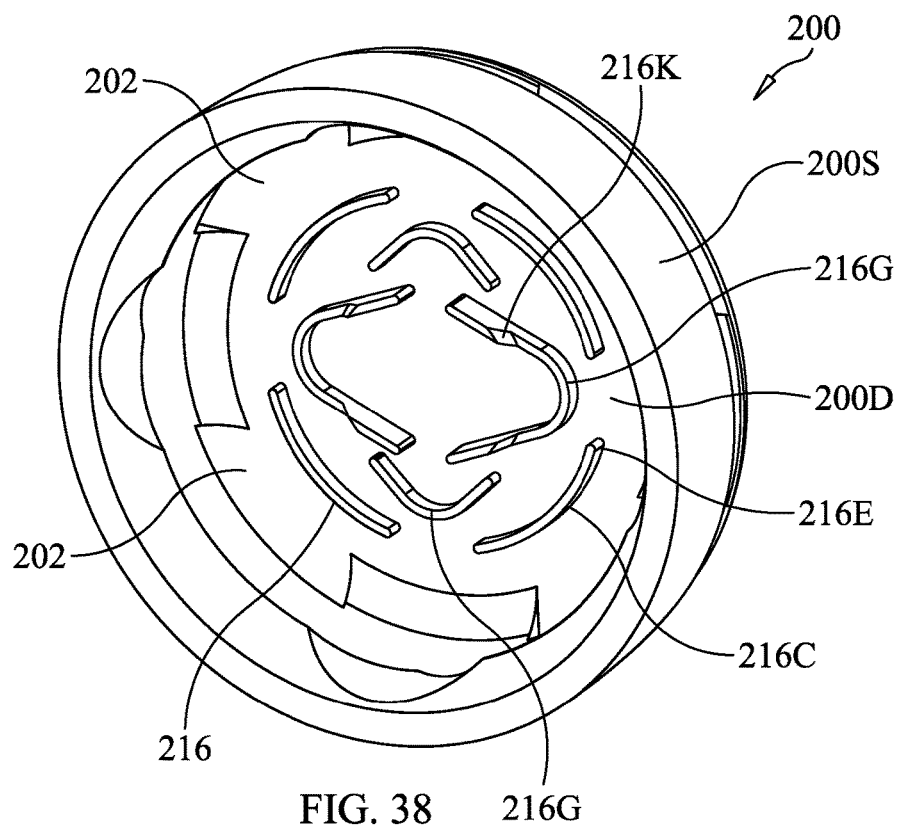
FIG. 38 is a perspective, distal end view of a proximal guard according to an embodiment of the present invention.
Figure 39:
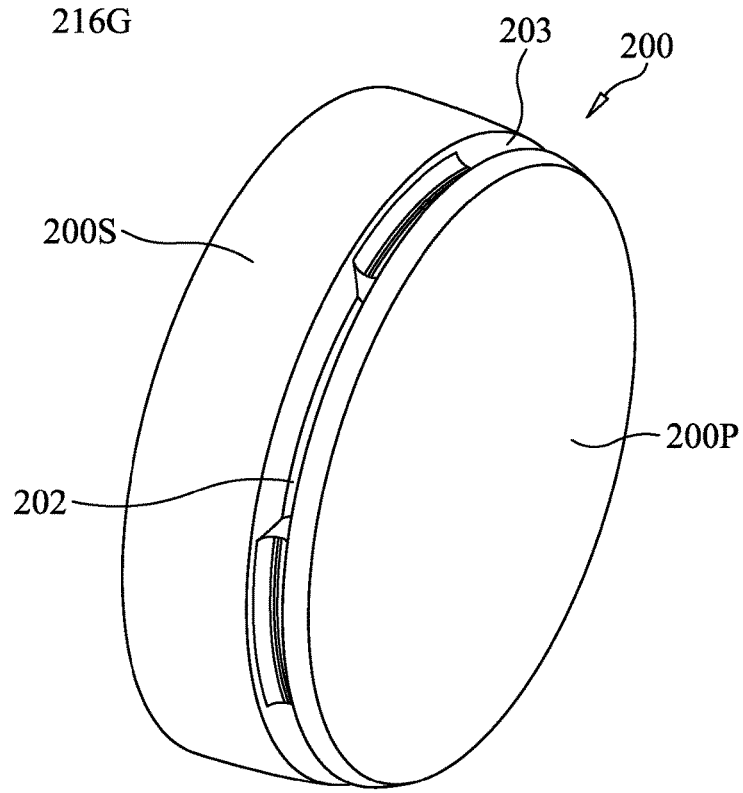
FIG. 39 is a perspective, proximal end view of the proximal guard of FIG. 38.
Figure 40:
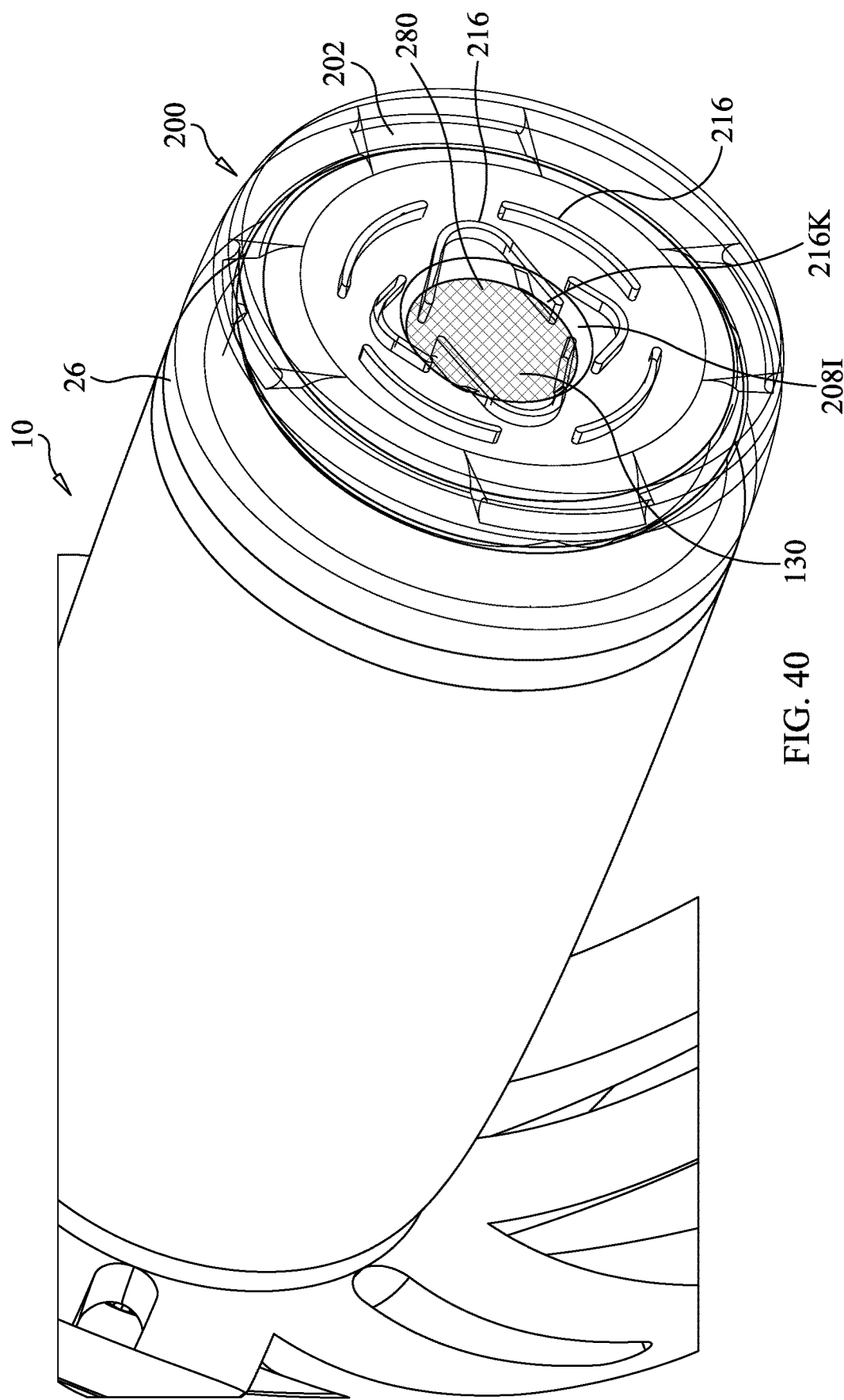
FIG. 40 shows the proximal guard (in a partially transparent view) of FIGS. 38-39 attached to a space access device, according to an embodiment of the present invention.

FIGS. 38 and 39 are perspective illustrations of the proximal end portion and distal end portion, respectively of a guard 200 according to another embodiment of the present invention. In this embodiment, rather than passing thorough the proximal end surface 200P of the guard 200 and through the distal surface 200D, openings 202 pass through the side walls 200S of the guard 200 so that air can flow thorough the outside wall and inside wall. 200S. Wipers 216 extend distally from the distal surface 200D and form a maze of convoluted pathways through which air must travel to go form opening 202 to the microphone port 280. FIG. 40 is a transparent view of the guard 200 of FIGS. 38-39 attached to cap 26 of a device 10 according to an embodiment of the invention. Note that the microphone port 280 in this case is circular rather than lozenge-shaped, but could be another shape, including, but not limited to, lozenge-shaped.

The wipers 216 may be provided in a nested configuration when viewed in a radial direction, which is what establishes the maze of air pathways. The nesting of the wipers 216 are to the extent such that they eliminate any radially straight through pathway from a port/opening 202 to the port 280, as can be seen in FIGS. 38 and 40. Thus, there is no direct air pathway in any radial direction outwardly from the port 280, either to a port 202, or to any other location along circumferentially along the inner wall 200S. At least one wiper may extend in a circumferential direction, such as wiper 216C shown in FIG. 38. Optionally, one or both ends 216E may be sharpened, tapered, or a knife edge. In any case, when guard 200 is rotated relative to cap 26 (FIG. 40) wiper 216C will cut through wax deposits in the air pathways. Other wipers 216 may form a wedge shape such as wipers 216G shown in FIG. 38. The wedge shaped wipers 216G tend to push wax/debris not only rotationally, but radially outwardly as the guard 200 is rotated relative to the cap 26. Like the wipers 216 in FIG. 24, the wipers 216G in FIG. 38 are tapered so that the width gradually decreases in a direction going radially outwardly. The tapered surfaces act to not only move the wax contacted in a rotational direction, but also tend to move the wax radially outwardly. The circumferentially extending wipers 216C also prevent wax from being pushed toward the openings 202. Blade 216K may be provided on one or more wipers 216 and extend distally further than a remainder of the wiper that it is formed on. Blade 216K is configured and positioned to extend into the microphone port 280 and interface with the inner wall of the opening of the microphone port 280 (see FIG. 40), so that rotation of guard 200 relative to cap 26 rotates the blade 216K along the inner wall, scraping wax accumulation (or other debris accumulation) that may formed there. The inner wall 208I may be angled outwardly to encourage scraped wax to move up and out of the opening 280. This outward angulation may be about 15 to 60 degrees relative to the longitudinal axis of the device 10, or about 20 to 45 degrees, in at least one embodiment about 30 degrees, where the angulation of the wall is outward in a direction from distal to proximal (i.e., toward the guard 200 and away from guard 100). Together, the plurality of wipers 216 are arranged to form a maze of convoluted air pathways through which air, sound and wax must travel to enter through openings 202 to reach the microphone port 280. The microphone port 280 is further covered with a mesh 130 which may include a hydrophobic and/or oleophobic coating. The same type of mesh may also be provided at the receiver port. The wipers 216 closely approximate the distal surface of the cap 26 when guard 200 is attached to cap 26. For example, the clearance between wiper 216 and surface of the cap 26 may be from 0 mm to about 1 mm, typically from about 0.1 mm to about 0.5 mm, In one particular example, the clearance was about 0.3 mm.

The provision of the openings 202 on the side walls of the guard may reduce the risk of compacting wax of other debris therethrough. For example, when a user inserts the device 10 into an ear canal, it is typically to push or press on the proximal wall of the guard 200 to push the device 10 into the ear canal. In the event that the users finger may have wax or other debris deposited on it, or, for example, if wax in the ear canal gets positioned between the user's finger and the proximal wall 200P, then there is a likelihood that this wax or other debris can be pressed into one or more openings 202 during the act of inserting the device. This likelihood is greatly diminished, if not eliminated, by placing the openings 202 through the side walls of the guard 200.

Openings 202 open through a slot 203 extending into the side outer wall 200S circumferentially around the guard 200. Slot 203 may also function as friction enhancement to the fingers of an operator as they are detaching the guard 200 from the cap 26. Additionally, or alternatively, the user may insert one or more finger nails into slot 203 to provide more leverage for detaching the guard 200 from the cap. As noted with regard to FIG. 30, the side walls 200S may also be tapered.

Surface 200P may be slightly concave to facilitate homing, self-centering or other secure addressing by the finger of a user during pushing on this surface for inserting the device. Further advantageously, the guard 200 can also be laid flat on a table or other flat surface, as a concave surface 200P will not prevent this. Alternatively, surface 200P could be flat or convex. Similarly, the proximal surface of the cap 26 may be slightly concave, but could alternatively be flat or convex. Likewise the distal end of the shell (e.g., distal tip 22) may be concave to make it easier to engage with the finger, and also to provide additional space for the second reservoir 120. Alternatively, the end may be convex or flat. Additionally, the concave surface 200P and/or other concave surfaces noted above, significantly reduce reflection/glare from being reflected therefrom. This helps keep the device 10 less noticeable when in position in the ear canal. All surfaces of the shell 12, cap 26 and guard 200 are preferably highly polished to further discourage adhesion of wax thereto. Further, the oleophobic and/or hydrophobic coatings described previously may be performed as a nano coating over all or any select portion of the device 10.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention.

The invention claimed is:

1. A guard for a space access device configured to output air flow through a distal end portion thereof, said guard comprising:
   a base comprising a longitudinal axis and an outer surface;
   a connector at a proximal end of said base, said connector configured to form a secure connection with a distal end of the space access device;
   a first filter located on a distal face of said base, and configured to allow air flow and/or sound therethrough, while discouraging the inflow of wax;
   a second filter at a proximal end portion of said base, said second filter being located within an opening defined by said connector; and
   at least one convoluted pathway within said base, for allowing air to pass through to said first and second filters;
   wherein said guard is configured to be attached to and removed from said space access device by hand, without the need for any tool.

2. A guard for a space access device configured to receive air flow through a proximal end portion thereof, said guard comprising:
   a first guard component comprising:
   a base comprising a proximal end, a distal external surface and a connector extending distally from said distal external surface;
   openings extending through said base from said proximal end to said connector;
   a filter located on or adjacent to said distal external surface, wherein said connector extends distally of said filter and has a channel in fluid communication with said filter and wherein said filter is configured to allow air flow/sound therethrough, while discouraging the inflow of wax and moisture; and
   a second connector extending proximally from said proximal end;
   wherein said first guard component is configured to be attached to and removed, via said second connector, from the space access device by hand, without the need for any tool; and
   wherein said connector is configured to connect to a second guard component.

3. A space access device comprising:
   a shell having a proximal end portion and a distal end portion; and
   a distal guard comprising: a base comprising a base proximal end portion; a base distal end portion; an outer surface; a connector at said base proximal end portion attachable to said distal end portion of said shell; a first filter located on a distal face of said base, and configured to allow air flow and/or sound therethrough, while discouraging the inflow of wax; a second filter in said base proximal end portion, within a first opening defined by said connector; and at least one convoluted pathway within said base, for allowing air to pass through to said first and second filters;
   wherein said distal guard is configured to be attached to and removed from said shell by hand, without the need for any tool.

4. The space access device of claim 3, wherein said shell comprises a distal tip extending from a distal end surface of said distal end portion, said distal tip configured and dimensioned to mate with said connector.

5. The space access device of claim 4, wherein said connector forms a snap fit with said distal tip.

6. The space access device of claim 3, wherein said distal guard further comprises a plurality of outwardly extending members integrally formed with said base and outwardly extending therefrom.

7. The space access device of claim 3, further comprising a pull tab extending from said base, said pull tab having a length sufficient so that at least a proximal end portion of said pull tab extends out of an ear canal when said space access device is installed in the ear canal in an operative position.

8. The space access device of claim 7, wherein said pull tab comprises at least two legs, each said leg being integrally attached to said distal guard to provide redundant features for more reliability against failure.

9. The space access device of claim 3, further comprising a proximal guard attachable to said proximal end portion of said shell, said proximal guard comprising:
   a second base comprising a proximal end, a distal surface and a second connector located distally of said distal surface; and
   at least one second opening extending through said second base and in fluid communication with at least one second convoluted pathway configured to be in fluid communication with said proximal end portion of said space access device when said second base is attached to said proximal end portion of said shell;
   wherein said proximal guard is configured to be attached to and removed from said proximal end portion of said shell by hand, without the need for any tool.

10. The space access device of claim 9, wherein said proximal end portion of said shell comprises a cap;
    wherein said cap comprises a central opening that overlies a microphone port contained in said shell; and
    wherein a proximal surface of said cap and said distal surface of said second base are configured to form said at least one second convoluted pathway between said at least one second opening and said central opening when said proximal guard is connected to said cap.

11. The space access device of claim 9, wherein said cap further comprises a mating connector configured and dimensioned to mate with said second connector.

12. The space access device of claim 11, wherein said second connector forms a snap fit with said mating connector.

13. The space access device of claim 11, wherein said cap tapers down from a distal end of said cap to said mating connector thereby forming a tapered surface;
    wherein a gap is formed between a distal end of said second connector and said tapered surface when said second connector and said mating connector are mated, such that an edge of said distal end is exposed, wherein said edge can be readily engaged by fingers of a user to apply force thereto so as to disconnect the proximal guard from the cap without the use of any tools.

14. The space access device of claim 3, wherein said space access device comprises an in-the-ear hearing aid.

15. The space access device of claim 3, wherein said space access device comprises an earpiece speaker.

16. The space access device of claim 9, wherein said space access device comprises an in-the-ear hearing aid.

17. A method of making a guard, said method comprising:
providing a base comprising a longitudinal axis and an outer surface and;
providing a connector at a proximal end of said base, said connector configured to form a secure connection with a distal end of a space access device;
providing a a first filter located on a distal end of said base, and configured to allow air flow and/or sound therethrough, while discouraging the inflow of wax; a second filter at a proximal end portion of said base, said second filter being located within an opening defined by said connector; and at least one convoluted pathway within said base, for allowing air to pass through to said first and second filters; and
integrally joining said base;
wherein said guard is configured to be attached to and removed from the space access device by hand, without the need for any tool.

18. A method of servicing a space access device, , said space access device including a shell having a proximal end portion and a distal end portion; and a distal guard comprising: a base comprising a base proximal end portion; a base distal end portion; an outer surface; a connector at said base proximal end portion attachable to said distal end portion of said shell; a first filter located on a distal face of said base, and configured to allow air flow and/or sound therethrough, while discouraging the inflow of wax; a second filter in said base proximal end portion, within a first opening defined by said connector; and at least one convoluted pathway within said base, for allowing air to pass through to said first and second filters; said method comprising:
securing a main body of the space access device with one hand;
using a second hand to align said connector of said distal guard with a distal mating connector on said main body; and
connecting said distal guard to said main body by hand, without the use of any tools.

19. A space access device comprising:
a shell having a proximal end portion and a distal end portion; and
a distal guard comprising: a base comprising a base proximal end portion; a base distal end portion; an outer surface; a connector at said base proximal end portion attachable to said distal end portion of said shell; a first filter in said base distal end portion; a second filter in said base proximal end portion, within a first opening defined by said connector; at least one convoluted pathway within said base, for allowing air to pass through to said first and second filters; and a pull tab extending from said base, said pull tab having a length sufficient so that at least a proximal end portion of said pull tab extends out of an ear canal when said space access device is installed in the ear canal in an operative position;
wherein said distal guard is configured to be attached to and removed from said shell by hand, without the need for any tool.

20. The space access device of claim 19, wherein said shell comprises a distal tip extending from a distal end surface of said distal end portion, said distal tip configured and dimensioned to mate with said connector.

21. The space access device of claim 20, wherein said connector forms a snap fit with said distal tip.

22. The space access device of claim 19, wherein said distal guard further comprises a plurality of outwardly extending members integrally formed with said base and outwardly extending therefrom.

23. The space access device of claim 19, wherein said pull tab comprises at least two legs, each said leg being integrally attached to said distal guard to provide redundant features for more reliability against failure.

24. The space access device of claim 19, wherein said space access device comprises an in-the-ear hearing aid.

25. The space access device of claim 19, wherein said space access device comprises an earpiece speaker.

26. A space access device comprising:
a shell having a proximal end portion and a distal end portion; and
a distal guard comprising: a base comprising a base proximal end portion; a base distal end portion; an outer surface; a connector at said base proximal end portion attachable to said distal end portion of said shell; a first filter in said base distal end portion; a second filter in said base proximal end portion, within a first opening defined by said connector; and at least one convoluted pathway within said base, for allowing air to pass through to said first and second filters;
wherein said distal guard is configured to be attached to and removed from said shell by hand, without the need for any tool;
a proximal guard attachable to said proximal end portion of said shell, said proximal guard comprising:
a second base comprising a proximal end, a distal surface and a second connector located distally of said distal surface; and
at least one second opening extending through said second base and connecting with at least one second convoluted pathway configured to be connected said proximal end portion of said space access device when said second base is attached to said proximal end portion of said shell;
wherein said proximal guard is configured to be attached to and removed from said proximal end portion of said shell by hand, without the need for any tool.

27. The space access device of claim 26, wherein said proximal end portion of said shell comprises a cap;
wherein said cap comprises a central opening that overlies a microphone port contained in said shell; and
wherein a proximal surface of said cap and said distal surface of said second base are configured to form said at least one second convoluted pathway between said at least one second opening and said central opening when said proximal guard is connected to said cap.

28. The space access device of claim 26, wherein said cap further comprises a mating connector configured and dimensioned to mate with said second connector.

29. The space access device of claim 28, wherein said second connector forms a snap fit with said mating connector.

30. The space access device of claim 28, wherein said cap tapers down from a distal end of said cap to said mating connector thereby forming a tapered surface;

wherein a gap is formed between a distal end of said second connector and said tapered surface when said second connector and said mating connector are mated, such that an edge of said distal end is exposed, wherein said edge can be readily engaged by fingers of a user to apply force thereto so as to disconnect the proximal guard from the cap without the use of any tools.

31. The space access device of claim 26, wherein said space access device comprises an in-the-ear hearing aid.

* * * * *